United States Patent
Lai et al.

(10) Patent No.: US 9,663,804 B2
(45) Date of Patent: May 30, 2017

(54) METHOD OF TREATING POLYESTER TEXTILE

(71) Applicant: Novozymes A/S, Bagsvaerd (DK)

(72) Inventors: Weijian Lai, Beijing (CN); Ting Sun, Beijing (CN); Leonardo De Maria, Frederiksberg (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 14/412,803

(22) PCT Filed: Jul. 18, 2013

(86) PCT No.: PCT/CN2013/079609
§ 371 (c)(1),
(2) Date: Jan. 5, 2015

(87) PCT Pub. No.: WO2014/012506
PCT Pub. Date: Jan. 23, 2014

(65) Prior Publication Data
US 2015/0191755 A1    Jul. 9, 2015

Related U.S. Application Data

(60) Provisional application No. 61/682,403, filed on Aug. 13, 2012.

(30) Foreign Application Priority Data

Jul. 18, 2012  (WO) ................ PCT/CN2012/078833

(51) Int. Cl.
| | | |
|---|---|---|
| *D06M 16/00* | (2006.01) | |
| *D06M 101/32* | (2006.01) | |
| *C12P 7/62* | (2006.01) | |
| *C12N 9/24* | (2006.01) | |

(52) U.S. Cl.
CPC .................. *C12P 7/62* (2013.01); *C12N 9/24* (2013.01); *C12Y 301/01074* (2013.01); *D06M 16/003* (2013.01); *D06M 2101/32* (2013.01)

(58) Field of Classification Search
CPC .......... C12N 9/24; C12P 7/72; D06M 16/003; D06M 2101/23; C09D 133/14; C08L 33/04; B29C 45/14786; B29K 2629/14; B29K 2713/00
See application file for complete search history.

(56) References Cited

U.S. PATENT DOCUMENTS

| | | | | |
|---|---|---|---|---|
| 6,815,180 | B1 * | 11/2004 | Kim ...................... | C07K 14/82 435/243 |
| 2012/0220513 | A1 * | 8/2012 | Allesen-Holm ....... | C12N 9/242 510/300 |

FOREIGN PATENT DOCUMENTS

| | | |
|---|---|---|
| JP | 6-136674 | 5/1999 |
| WO | 97/27237 A1 | 7/1997 |
| WO | 99/01604 A1 | 1/1999 |
| WO | 00/34450 A1 | 6/2000 |
| WO | 01/34899 A1 | 5/2001 |
| WO | 01/92502 A1 | 12/2001 |
| WO | 2009/087525 A1 | 7/2009 |
| WO | 2010/065830 A1 | 6/2010 |
| WO | 2011/080267 A2 | 7/2011 |
| WO | 2012/061517 A1 | 5/2012 |
| WO | 2012/089023 A1 | 7/2012 |

* cited by examiner

*Primary Examiner* — Kagnew H Gebreyesus
(74) *Attorney, Agent, or Firm* — Elias Lambiris

(57) ABSTRACT

The present invention relates to the use of glycosyl hydrolase family 61 polypeptides in the presence of cutinases for polyester textile manufacture as well as a textile composition comprising glycosyl hydrolase family 61 polypeptides and cutinases.

20 Claims, No Drawings

METHOD OF TREATING POLYESTER TEXTILE

CROSS-REFERENCE TO RELATED APPLICATIONS

This application is a 35 U.S.C. 371 national application of international application no. PCT/CN2013/079609 filed Jul. 18, 2013, which claims priority or the benefit under 35 U.S.C. 119 of international application no. PCT/CN2012/078833 filed Jul. 18, 2012 and U.S. provisional application No. 61/682,403 filed Aug. 13, 2012. The content of each application is fully incorporated herein by reference.

REFERENCE TO SEQUENCE LISTING

This application contains a Sequence Listing in computer readable form. The computer readable form is incorporated herein by reference.

FIELD OF THE INVENTION

The present invention relates to the use of glycosyl hydrolase family 61 polypeptides and cutinase in the treatment of polyester textile, as well as a textile composition comprising glycosyl hydrolase family 61 polypeptides and cutinase.

BACKGROUND OF THE INVENTION

Polyethylene terephthalate (abbreviated as PET) fibers accounts for the main part of the polyester applied by the textile industry. The fibers are produced by e.g. polycondensation of terephthalic acid and ethylene glycol, and drawing of fibers from a melt.

Polyester has certain key advantages including high strength, soft hand, stretch resistance, stain resistance, machine washability, wrinkle resistance and abrasion resistance. However, polyester is not so optimal in terms of its hydrophobicity, pilling, static, dyeability, inactive surface as a medium for adhering, i.e., softening or wettability enhancing compounds, lack of breathability and undesirable high shine or luster appearance.

Because of its strength, polyester fabrics and/or garments are subject to pill formation, and possibly the most important of the cloth finishing processes applied to polyester staple-fibre materials are those designed for control of pilling. All staple-fibre materials tend to form small balls or "pills" of entangled fibres at the cloth surface, when subjected to mild abrasion during wash and wear. If the fabric contains a substantial proportion of fibres having high resistance to flexural abrasion, the pills may be retained on the surface of the cloth in sufficient numbers to produce an unpleasant handle and appearance.

Another problem with polyester is that during synthesis of PET, cyclic or linear oligomers of poly (ethylene terephthalate), such as terephthalic acid-bis-2-benzoyloxy-ethylesther (abbreviated as BETEB) and/or cyclic tri(ethylene terephthalate) are formed. These oligomers are partly deposited on machinery and partly staying on and/or in the fibers. Oligomers tend to give fabrics a grayish appearance. This is due to deposits of oligomers on the surface of the fabric, which is particularly outspoken after high temperature wet processes like high temperature dyeing. The oligomers can be removed by severe alkaline treatment, which results in a significant loss of fiber material. Organic extraction of the oligomers is a technical possibility, but not industrially feasible.

The industry has made great efforts to improve the characteristics of polyester, in particular the reduction of pill formation.

WO 99/001604 discloses a method of reducing the pilling propensity of polyester fabrics and/or garments with a terephthalic acid diethyl ester hydrolytic enzyme (ETE hydrolytic enzyme) and/or an ethyleneglycol dibenzyl ester hydrolytic enzyme (BEB hydrolytic enzyme).

WO 2001/34899 discloses a method for modifying polyester comprising treating said polyester with a polyesterase enzyme.

WO 97/27237 discloses the enzymatic hydrolysis of cyclic oligomers of poly (ethylene terephthalate), which comprises subjecting the cyclic oligomer to the action of one or more carboxylic ester hydrolases.

WO 2001/092502 discloses the treatment of polyester textile with *Humicola insolens* cutinase variants.

However, there is still a need for improved benefit of enzymatic polyester fabric and/or garment treatment, including enhancing the efficiency of the enzymes to their substrates. In particular, there is a continuous need for more efficient enzyme composition to improve the economics of the process. The present invention aims to meet these needs.

SUMMARY OF THE INVENTION

The present invention relates to a method for treating polyester textile with a glycosyl hydrolase family 61 (GH61) polypeptide in the presence of a cutinase in an aqueous solution.

The present invention also relates to a textile composition comprising a glycosyl hydrolase family 61 polypeptide and a cutinase.

In some embodiments, the polyester textile treatment process may further comprise one or more enzymes selected from the group consisting of lipases, esterases, laccases, peroxidases and peroxygenase and transferases.

In preferred embodiment, the polyester textile is a PET textile.

In the present invention, GH61 polypeptides can enhance the efficiency of the cutinase to its substrate with at least one of the following benefits: reduction of oligomer in the polyester textile, reduction of pill formation, and without substantial weight loss of fabric in a biopolishing process, improvement on the wettability/hydrophilicity and antistatic properties of polyester fabric.

In one embodiment, a number of enzymes can be used together with cutinase and GH61 for polyester treatment process, which comprises one or more enzymes selected from the group consisting of lipases, esterases, laccase, peroxidase, peroxygenase and transferases.

In one embodiment, the method and composition of the present invention may further comprise a co-substance, such as cysteine and ascorbate.

In some embodiments, the method for manufacturing polyester textile is provided. In some embodiments, the textile is manufactured from fabric to garment.

In some embodiments, the cutinase used in the present invention is a cutinase having BETEB hydrolysis activity.

DETAILED DESCRIPTION OF THE INVENTION

The invention will now be described in detail by way of reference using the following definitions and examples. All patents and publications, including all sequences disclosed within such patents and publications, referred to herein are expressly incorporated by reference.

As used herein, the singular terms "a", "an," and "the" include the plural reference unless the context clearly indicates otherwise.

Polyester Textile

"Polyester" as used herein means a linear polymeric molecule containing in-chain ester groups which are derived from condensation of a diacid with a diol or from the polymerization of hydroxy acids. The present invention applies to both aliphatic and aromatic polyesters. Particularly preferred polyesters are aromatic polyester articles which are used to produce fiber and resin and that comprise a synthetically produced long chain polymer comprising at least 85%, preferably at least 90% and most preferably at least 95%, by weight of an ester of a substituted aromatic carboxylic acid, such as substituted terephthalic acid or parasubstituted hydroxybenzoate or a mixture thereof. Other useful polyester articles include those made of bulk polymer, yarns, fabrics, films, resins and powders. The principal polyesters in industrial usage include polyethylene terephthalate (PET), tetramethylene terephthalate (PTMT), polybutylene teraphthalate (PBT), polytrimethylene terephthalate (PTT) and polyethylenenaphthalate (PEN), polycyclohexanedimethylene terephthalate (CHDMT), polyethylene-4-oxybenzoate, A-Tell, polyglycolide, PHBA and 2GN. However, PET is the most common linear polymer produced and accounts for a majority of the polyester applied in industry today.

The polyester textile used herein is meant to include fibers, yarns, fabrics and garments comprising polyester. The polyester yarn or fabric or garment may be any yarn or fabric or garment that is made from pure poly (ethylene terephthalate), or that is made from blends of poly (ethylene terephthalate) fibers and any other materials conventionally used for making textile such as wool, cotton, viscose and silk.

In a preferred embodiment the polyester fabric is a fabric blend comprising more than 35% (w/w) of polyester, in particular more than 50%, more than 65%, more than 90%, or more than 95% of polyester. In a most preferred embodiment, the process of the invention is applied to fabrics or garments consisting essentially of poly (ethylene terephthalate) polyester material, i.e. pure poly (ethylene terephthalate) polyester material.

Cutinase

Cutinases are lipolytic enzymes classified as EC 3.1.1.74 according to Enzyme Nomenclature. Reference is made to the Recommendations of the Nomenclature Committee of the International Union of Biochemistry and Molecular Biology, Academic Press Inc., 1992

For purposes of the present invention, cutinase activity is determined using oligomer Terephthalic acid-bis-2-benzoyloxy-ethylesther (BETEB) as substrate according to Example 1 of the present invention. BETEB is a by-product during the PET synthesis and is generally remained in the fabric or garment during textile manufacturing. BETEB is produced by e.g. condensation of terephthalic acid, benzoic acid and ethylene glycol, which has the same unit of benzoyloxy-ethylester as PET.

The enzyme in question qualifies as a cutinase for use according to the present invention if transparent zones are shown after testing in Example 1.

Cutinases are known from various fungi, such as a filamentous fungal cutinase, e.g. native to a strain of *Humicola* or *Fusarium* or *Magnaporthe* or *Pseudomonas*, specifically *H. insolens* or *F. solani pisi* or *Magnaporthe grisea* or *Pseudomonas mendocina*, more specifically *H. insolens* strain DSM 1800 (U.S. Pat. No. 5,827,719), or *F. solani pisi* (WO 90/09446 FIG. 1; WO 94/14964 FIG. 1D, WO 94/03578 FIG. 1D, all hereby incorporated by reference) or *Magnaporthe grisea* (WO10/107560 SEQ ID NO: 1, hereby incorporated by reference) or *Pseudomonas mendocina* ATCC 53552 (U.S. Pat. No. 5,389,536, claim 1, hereby incorporated by reference).

SEQ ID NO: 1 is the amino acid sequence of the *Humicola insolens* cutinase (corresponding to the mature part of SEQ ID NO: 2 of U.S. Pat. No. 5,827,719).

In one embodiment, the cutinase of the present invention has at least 70%, or 75%, or 85%, or 90%, or 95%, or 96%, or 97%, or 98%, or 99%, or 100% identity to SEQ ID NO: 1.

In some embodiments, the cutinase can be variants comprising a substitution, deletion, and/or insertion of one or more (or several) amino acids of SEQ ID NO: 1. Preferably, the total number of amino acid substitutions, deletions and/or insertions of the SEQ ID NO: 1 is not more than 10, e.g., 1, 2, 3, 4, 5, 6, 7, 8 or 9. The *Humicola insolens* cutinase variants described in WO 2001/092502 are hereby incorporated by reference. The cutinase enzyme may also be a variant of a parent cutinase such as those described in WO 00/34450, hereby incorporated by reference.

The fungal cutinase may also be derived from other fungal strains such as a strain of *Rhizoctonia*, e.g. *R. solani*, or a strain of *Alternaria*, e.g. *A. brassicicola* (WO 94/03578).

Preferably the cutinase has a pH optimum within 1 pH unit of the pH of the process, e.g. if the process is run at pH 8, the cutinase preferably has a pH optimum between 7 and 9.

Sequence Identity

The relatedness between two amino acid sequences or between two nucleotide sequences is described by the parameter "sequence identity".

For purposes of the present invention, the degree of sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the –nobrief option) is used as the percent identity and is calculated as follows:

(Identical Residues×100)/(Length of Alignment–
Total Number of Gaps in Alignment)

For purposes of the present invention, the degree of sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the –nobrief option) is used as the percent identity and is calculated as follows:

(Identical Deoxyribonucleotides×100)/(Length of Alignment−Total Number of Gaps in Alignment)

Glycoside Hydrolase Family 61 (GH61) Polypeptides

The term "glycoside hydrolase family 61" or "GH61" is defined herein as a polypeptide falling into the glycoside hydrolase family 61 according to Henrissat B., 1991, Biochem. J. 280: 309-316, and Henrissat B., and Bairoch A., 1996, Biochem. J. 316: 695-696.

The present invention relates to the use of isolated GH61 polypeptides in general. A GH61 polypeptide useful in the present invention may be obtained from microorganisms of any genus. For purposes of the present invention, the term "obtained from" as used herein in connection with a given source shall mean that the polypeptide encoded by a nucleotide sequence is produced by the source in which it is naturally present or by a strain in which the nucleotide sequence from the source has been inserted. In a preferred aspect, the polypeptide obtained from a given source is secreted extracellularly.

A GH61 polypeptide of the present invention may be a bacterial polypeptide. For example, the polypeptide may be a gram positive bacterial polypeptide such as a *Bacillus* polypeptide, e.g., a *Bacillus alkalophilus, Bacillus amyloliquefaciens, Bacillus brevis, Bacillus circulans, Bacillus coagulans, Bacillus lautus, Bacillus lentus, Bacillus licheniformis, Bacillus megaterium, Bacillus stearothermophilus, Bacillus subtilis,* or *Bacillus thuringiensis* polypeptide; or a *Streptomyces* polypeptide, e.g., a *Streptomyces lividans* or *Streptomyces murinus* polypeptide; or a gram negative bacterial polypeptide, e.g., an *E. coli* or a *Pseudomonas* sp. polypeptide.

A GH61 polypeptide of the present invention may also be a fungal polypeptide, and more preferably a yeast polypeptide such as a *Candida, Kluyveromyces, Pichia, Saccharomyces, Schizosaccharomyces,* or *Yarrowia* polypeptide; or more preferably a filamentous fungal polypeptide such as an *Acremonium, Aspergillus, Aureobasidium, Chaetomium, Cryptococcus, Filibasidium, Fusarium, Humicola, Magnaporthe, Mucor, Myceliophthora, Neocallimastix, Neurospora, Paecilomyces, Penicillium, Piromyces, Poronia, Schizophyllum, Talaromyces, Thermoascus, Thielavia, Tolypocladium, Trichoderma* or *Verticillium* polypeptide.

In the present invention, any GH61 polypeptide having cutinase enhancing activity can be used.

In one embodiment, for purposes of the present invention, cutinase enhancing activity is determined by the reduction of oligomer in the PET, i.e. by measuring the increase in OD 254 absorbance under conditions as specified in Example 4, by hydrolyzing BETEB with cutinase and GH61 at a dosage of 0.05 mg protein/ml at 70° C., pH 8.0 for 40 minutes. In a preferred embodiment of the present invention, the OD is increased by at least 0.25, preferably at least 0.28, more preferably at least 0.3, more preferably at least 0.33, more preferably at least 0.35, more preferably at least 0.38, more preferably at least 0.40, even more preferably at least 0.43, and most preferably at least 0.45 as compared to the OD result when the cutinase is used without GH61.

In some embodiments, cutinase enhancing activity is determined by measuring the reduction of pill formation under conditions as specified in Example 6, by treating PET in Launder-O-Meter with cutinase and GH61 at a dosage of 2.8 mg protein/gram of fabric at 70° C., pH 8.0 for 2 hours. In a preferred embodiment of the present invention, it shows the pilling note increased by at least 0.125, more preferably at least 0.250, more preferably at least 0.375, more preferably at least 0.500, more preferably at least 0.625, even more preferably at least 0.750 as compared to the pilling note when the cutinase is used without GH61.

In a first aspect, GH61 polypeptides having cutinase enhancing activity, comprise the following motifs:
[ILMV]-P-X(4,5)-G-X-Y-[ILMV]-X-R-X-[EQ]-X(4)-[HNQ] and [FW]-[TF]-K-[AIV],
wherein X is any amino acid, X(4,5) is any amino acid at 4 or 5 contiguous positions, and X(4) is any amino acid at 4 contiguous positions.

The isolated polypeptide comprising the above-noted motifs may further comprise:
H-X(1,2)-G-P-X(3)-[YW]-[AILMV],
[EQ]-X-Y-X(2)-C-X-[EHQN]-[FILV]-X-[ILV], or
H-X(1,2)-G-P-X(3)-[YW]-[AILMV] and [EQ]-X-Y-X(2)-C-X-[EHQN]-[FILV]-X-[ILV],
wherein X is any amino acid, X(1,2) is any amino acid at 1 position or 2 contiguous positions, X(3) is any amino acid at 3 contiguous positions, and X(2) is any amino acid at 2 contiguous positions. In the above motifs, the accepted IUPAC single letter amino acid abbreviation is employed.

In a preferred embodiment, the isolated GH61 polypeptide having cutinase enhancing activity further comprises H-X(1,2)-G-P-X(3)-[YW]-[AILMV]. In another preferred embodiment, the isolated GH61 polypeptide having cutinase enhancing activity further comprises [EQ]-X-Y-X(2)-C-X-[EHQN]-[FILV]-X-[ILV]. In another preferred embodiment, the isolated GH61 polypeptide having cutinase enhancing activity further comprises H-X(1,2)-G-P-X(3)-[YW]-[AILMV] and [EQ]-X-Y-X(2)-C-X-[EHQN]-[FILV]-X-[ILV].

In a second aspect, isolated polypeptides having cutinase enhancing activity, comprise the following motif:
[ILMV]-P-X(4,5)-G-X-Y-[ILMV]-X-R-X-[EQ]-X(3)-A-[HNQ],
wherein X is any amino acid, X(4,5) is any amino acid at 4 or 5 contiguous positions, and X(3) is any amino acid at 3 contiguous positions. In the above motif, the accepted IUPAC single letter amino acid abbreviation is employed.

In a third aspect, the GH61 polypeptide having cutinase enhancing activity comprises or consists of an amino acid sequence having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, or at least 95%, at least 96%, at least 97%, at least 98%, at least 99%, or at least 100% sequence identity to the mature polypeptide of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46 or SEQ ID NO: 47.

In an embodiment, the mature polypeptide comprises or consists of amino acids 20 to 326 of SEQ ID NO: 2, amino acids 18 to 239 of SEQ ID NO: 3, amino acids 20 to 258 of SEQ ID NO: 4, amino acids 19 to 226 of SEQ ID NO: 5, amino acids 20 to 304 of SEQ ID NO: 6, amino acids 16 to 317 of SEQ ID NO: 7, amino acids 22 to 249 of SEQ ID NO: 8, amino acids 20 to 249 of SEQ ID NO: 9, amino acids 18 to 232 of SEQ ID NO: 10, amino acids 16 to 235 of SEQ ID NO: 11, amino acids 19 to 323 of SEQ ID NO: 12, amino acids 16 to 310 of SEQ ID NO: 13, amino acids 20 to 246 of SEQ ID NO: 14, amino acids 22 to 354 of SEQ ID NO: 15, amino acids 22 to 250 of SEQ ID NO: 16, amino acids 22 to 322 of SEQ ID NO: 17, amino acids 24 to 444 of SEQ ID NO: 18, amino acids 26 to 253 of SEQ ID NO: 19, amino acids 18 to 246 of SEQ ID NO: 20, amino acids 20 to 334 of SEQ ID NO: 21, amino acids 18 to 227 of SEQ ID NO: 22, amino acids 20 to 223 of SEQ ID NO: 23, amino acids 22 to 368 of SEQ ID NO: 24, amino acids 25 to 330 of SEQ ID NO: 25, amino acids 17 to 236 of SEQ ID NO: 26, amino acids 19 to 250 of SEQ ID NO: 27, amino acids 23 to 478 of SEQ ID NO: 28, amino acids 17 to 230 of SEQ ID NO: 29, amino acids 20 to 257 of SEQ ID NO: 30, amino acids 23 to 251 of SEQ ID NO: 31, amino acids 19 to 349 of SEQ ID NO: 32, amino acids 24 to 436 of SEQ ID NO: 33, amino acids 21 to 344 of SEQ ID NO: 34, amino acids 26 to 400 of SEQ ID NO: 35, amino acids 21 to 389 of SEQ ID NO: 36, amino acids 22 to 406 of SEQ ID NO: 37, amino acids 20 to 427 of SEQ ID NO: 38, amino acids 18 to 267 of SEQ ID NO: 39, amino acids 21 to 273 of SEQ ID NO: 40, amino acids 21 to 322 of SEQ ID NO: 41, amino acids 18 to 234 of SEQ ID NO: 42, amino acids 24 to 233 of SEQ ID NO: 43, amino acids 17 to 237 of SEQ ID NO: 44, amino acids 20 to 484 of SEQ ID NO: 45, amino acids 22 to 320 of SEQ ID NO: 46, or amino acids 21 to 330 of SEQ ID NO: 47.

Preferably, the GH61 polypeptide having cutinase enhancing activity comprises or consists of an amino acid sequence having at least 90% identity to the mature polypeptide of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46 or SEQ ID NO: 47. More preferably at least 95% identity to the mature polypeptide of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46 or SEQ ID NO: 47. Most preferably at least 100% identity to the mature polypeptide of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46 or SEQ ID NO: 47

In a sixth aspect, the GH61 polypeptide having cutinase enhancing activity is a variant of the mature polypeptide of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46 or SEQ ID NO: 47 comprising a substitution, deletion, and/or insertion at one or more (e.g., several) positions.

Preferably, amino acid changes are of a minor nature, that is conservative amino acid substitutions or insertions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, *The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a parent polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for cutinase enhancing activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992,

*J. Mol. Biol.* 224: 899-904; Wlodaver et al., 1992, *FEBS Lett.* 309: 59-64. The identities of essential amino acids can also be inferred from analysis of identities with polypeptides that are related to the parent polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The total number of amino acid substitutions, deletions and/or insertions of the mature polypeptide of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46 or SEQ ID NO: 47, is up to 10, e.g., 1, 2, 3, 4, 5, 6, 7, 8, 9, or 10.

In an embodiment, the mature polypeptide comprises or consists of amino acids 20 to 326 of SEQ ID NO: 2, amino acids 18 to 239 of SEQ ID NO: 3, amino acids 20 to 258 of SEQ ID NO: 4, amino acids 19 to 226 of SEQ ID NO: 5, amino acids 20 to 304 of SEQ ID NO: 6, amino acids 16 to 317 of SEQ ID NO: 7, amino acids 22 to 249 of SEQ ID NO: 8, amino acids 20 to 249 of SEQ ID NO: 9, amino acids 18 to 232 of SEQ ID NO: 10, amino acids 16 to 235 of SEQ ID NO: 11, amino acids 19 to 323 of SEQ ID NO: 12, amino acids 16 to 310 of SEQ ID NO: 13, amino acids 20 to 246 of SEQ ID NO: 14, amino acids 22 to 354 of SEQ ID NO: 15, amino acids 22 to 250 of SEQ ID NO: 16, amino acids 22 to 322 of SEQ ID NO: 17, amino acids 24 to 444 of SEQ ID NO: 18, amino acids 26 to 253 of SEQ ID NO: 19, amino acids 18 to 246 of SEQ ID NO: 20, amino acids 20 to 334 of SEQ ID NO: 21, amino acids 18 to 227 of SEQ ID NO: 22, amino acids 20 to 223 of SEQ ID NO: 23, amino acids 22 to 368 of SEQ ID NO: 24, amino acids 25 to 330 of SEQ ID NO: 25, amino acids 17 to 236 of SEQ ID NO: 26, amino acids 19 to 250 of SEQ ID NO: 27, amino acids 23 to 478 of SEQ ID NO: 28, amino acids 17 to 230 of SEQ ID NO: 29, amino acids 20 to 257 of SEQ ID NO: 30, amino acids 23 to 251 of SEQ ID NO: 31, amino acids 19 to 349 of SEQ ID NO: 32, amino acids 24 to 436 of SEQ ID NO: 33, amino acids 21 to 344 of SEQ ID NO: 34, amino acids 26 to 400 of SEQ ID NO: 35, amino acids 21 to 389 of SEQ ID NO: 36, amino acids 22 to 406 of SEQ ID NO: 37, amino acids 20 to 427 of SEQ ID NO: 38, amino acids 18 to 267 of SEQ ID NO: 39, amino acids 21 to 273 of SEQ ID NO: 40, amino acids 21 to 322 of SEQ ID NO: 41, amino acids 18 to 234 of SEQ ID NO: 42, amino acids 24 to 233 of SEQ ID NO: 43, amino acids 17 to 237 of SEQ ID NO: 44, amino acids 20 to 484 of SEQ ID NO: 45, amino acids 22 to 320 of SEQ ID NO: 46 or amino acids 1 to 20 of SEQ ID NO: 47.

Co-Substance

The addition of a co-substance together with GH61 polypeptides can enhance the enzymatic efficiency even further.

In one aspect, the GH61 polypeptide having cutinase enhancing activity is used in the presence of a soluble activating divalent metal cation according to WO 2008/151043. In a preferred aspect, the soluble activating divalent metal cation is selected from the alkali metals or transition metals in the periodic table. In a more preferred aspect, the soluble activating divalent metal cation is selected from the group consisting of Mn++, Co++, Mg++, Ca++, and a combination thereof. In a more preferred aspect, the soluble activating divalent metal cation is Mn++. In another more preferred aspect, the soluble activating divalent metal cation is Co++. In another more preferred aspect, the soluble activating divalent metal cation is Mg++. In another more preferred aspect, the soluble activating divalent metal cation is Ca++. In another more preferred aspect, the soluble activating divalent metal cation is two or more (several) cations selected from the group consisting of Mn++, Co++, Mg++, and Ca++. In a most preferred aspect the soluble activating divalent metal cation is in the form of manganese sulfate.

In one aspect, the GH61 polypeptide having cutinase enhancing activity is used in the presence of a dioxy compound, a bicyclic compound, a heterocyclic compound, a nitrogen-containing compound, or a sulfur-containing compound.

The dioxy compound may include any suitable compound containing two or more oxygen atoms. In some aspects, the dioxy compounds contain a substituted aryl moiety as described herein. The dioxy compounds may comprise one or more (e.g., several) hydroxyl and/or hydroxyl derivatives, but also include substituted aryl moieties lacking hydroxyl and hydroxyl derivatives. Non-limiting examples of the dioxy compounds include pyrocatechol or catechol; caffeic acid; 3,4-dihydroxybenzoic acid; 4-tert-butyl-5-methoxy-1,2-benzenediol; pyrogallol; gallic acid; methyl-3,4,5-trihydroxybenzoate; 2,3,4-trihydroxybenzophenone; 2,6-dimethoxyphenol; sinapinic acid; 3,5-dihydroxybenzoic acid; 4-chloro-1,2-benzenediol; 4-nitro-1,2-benzenediol; tannic acid; ethyl gallate; methyl glycolate; dihydroxyfumaric acid; 2-butyne-1,4-diol; (croconic acid; 1,3-propanediol; tartaric acid; 2,4-pentanediol; 3-ethyoxy-1,2-propanediol; 2,4,4'-trihydroxybenzophenone; cis-2-butene-1,4-diol; 3,4-dihydroxy-3-cyclobutene-1,2-dione; dihydroxyacetone; acrolein acetal; methyl-4-hydroxybenzoate; 4-hydroxybenzoic acid; and methyl-3,5-dimethoxy-4-hydroxybenzoate; or a salt or solvate thereof.

The bicyclic compound may include any suitable substituted fused ring system as described herein. The compounds may comprise one or more (e.g., several) additional rings, and are not limited to a specific number of rings unless otherwise stated. In one aspect, the bicyclic compound is a flavonoid. In another aspect, the bicyclic compound is an optionally substituted isoflavonoid. In another aspect, the bicyclic compound is an optionally substituted flavylium ion, such as an optionally substituted anthocyanidin or optionally substituted anthocyanin, or derivative thereof.

Non-limiting examples of the bicyclic compounds include epicatechin; quercetin; myricetin; taxifolin; kaempferol; morin; acacetin; naringenin; isorhamnetin; apigenin; cyanidin; cyanin; kuromanin; keracyanin; or a salt or solvate thereof.

The heterocyclic compound may be any suitable compound, such as an optionally substituted aromatic or nonaromatic ring comprising a heteroatom, as described herein. In one aspect, the heterocyclic is a compound comprising an optionally substituted heterocycloalkyl moiety or an optionally substituted heteroaryl moiety. In another aspect, the optionally substituted heterocycloalkyl moiety or optionally substituted heteroaryl moiety is an optionally substituted 5-membered heterocycloalkyl or an optionally substituted 5-membered heteroaryl moiety. In another aspect, the optionally substituted heterocycloalkyl or optionally substituted heteroaryl moiety is an optionally substituted moiety selected from pyrazolyl, furanyl, imidazolyl, isoxazolyl, oxadiazolyl, oxazolyl, pyrrolyl, pyridyl, pyrimidyl, pyridazinyl, thiazolyl, triazolyl, thienyl, dihydrothienopyrazolyl, thianaphthenyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, isoindolyl, acridinyl, benzoisazolyl, dimethylhydantoin, pyrazinyl, tetrahydrofuranyl, pyrrolinyl, pyrrolidinyl, morpholinyl, indolyl, diazepinyl, azepinyl, thiepinyl, piperidinyl, and oxepinyl. In another aspect, the optionally substituted heterocycloalkyl moiety or optionally substituted heteroaryl moiety is an optionally substituted furanyl. Non-limiting examples of the heterocyclic compounds include (1,2-dihydroxyethyl)-3,4-dihydroxyfuran-2(5H)-one; 4-hydroxy-5-methyl-3-furanone; 5-hydroxy-2(5H)-furanone; [1,2-dihydroxyethyl]furan-2,3,4(5H)-trione; α-hydroxy-γ-butyrolactone; ribonic γ-lactone; aldohexuronicaldohexuronic acid γ-lactone; gluconic acid δ-lactone; 4-hydroxycoumarin; dihydrobenzofuran; 5-(hydroxymethyl) furfural; furoin; 2(5H)furanone; 5,6-dihydro-2H-pyran-2-one; and 5,6-dihydro-4-hydroxy-6-methyl-2H-pyran-2-one; or a salt or solvate thereof.

The nitrogen-containing compound may be any suitable compound with one or more (e.g., several) nitrogen atoms. In one aspect, the nitrogen-containing compound comprises an amine, imine, hydroxylamine, or nitroxide moiety. Non-limiting examples of the nitrogen-containing compounds include acetone oxime; violuric acid; pyridine-2-aldoxime; 2-aminophenol; 1,2-benzenediamine; 2,2,6,6-tetramethyl-1-piperidinyloxy; 5,6,7,8-tetrahydrobiopterin; 6,7-dimethyl-5,6,7,8-tetrahydropterine; and maleamic acid; or a salt or solvate thereof.

The quinone compound may be any suitable compound comprising a quinone moiety as described herein. Non-limiting examples of the quinone compounds include 1,4-benzoquinone; 1,4-naphthoquinone; 2-hydroxy-1,4-naphthoquinone; 2,3-dimethoxy-5-methyl-1,4-benzoquinone or coenzyme $Q_0$; 2,3,5,6-tetramethyl-1,4-benzoquinone or duroquinone; 1,4-dihydroxyanthraquinone; 3-hydroxy-1-methyl-5,6-indolinedione or adrenochrome; 4-tert-butyl-5-methoxy-1,2-benzoquinone; pyrroloquinoline quinone; or a salt or solvate thereof.

The sulfur-containing compound may be any suitable compound comprising one or more (e.g., several) sulfur atoms. In one aspect, the sulfur-containing comprises a moiety selected from thionyl, thioether, sulfinyl, sulfonyl, sulfamide, sulfonamide, sulfonic acid, and sulfonic ester. Non-limiting examples of the sulfur-containing compounds include ethanethiol; 2-propanethiol; 2-propene-1-thiol; 2-mercaptoethanesulfonic acid; benzenethiol; benzene-1,2-dithiol; cysteine; methionine; glutathione; cysteine; or a salt or solvate thereof.

In one aspect, the amount of such a compound described above to polyester textile material as a molar ratio to glucosyl units of cellulose is about $10^{-6}$ to about 10, e.g., about $10^{-6}$ to about 7.5, about $10^{-6}$ to about 5, about $10^{-6}$ to about 2.5, about $10^{-6}$ to about 1, about $10^{-5}$ to about 1, about $10^{-5}$ to about $10^{-1}$, about $10^{-4}$ to about $10^{-1}$, about $10^{-3}$ to about $10^{-1}$, or about $10^{-3}$ to about $10^{-2}$. In another aspect, the amount of such a compound described above is about 0.1 µM to about 1 M, e.g., about 0.5 µM to about 0.75 M, about 0.75 µM to about 0.5 M, about 1 µM to about 0.25 M, about 1 µM to about 0.1 M, about 5 µM to about 50 mM, about 10 µM to about 25 mM, about 50 µM to about 25 mM, about 10 µM to about 10 mM, about 5 µM to about 5 mM, or about 0.1 mM to about 1 mM.

The term "liquor" means the solution phase, either aqueous, organic, or a combination thereof.

Polyester Fabric Manufacturing Process

Polyester such as poly (ethylene terephthalate) is synthesized by condensation, drawn into fibers from a melt, possibly cut to stables, possibly mixed with other fiber types, and spun to yarn.

After yarn is knitted or woven into fabric, the fabric is normally treated to remove spin finish oil, for example in a process where the fabric will first be heat setted at 180° C. and then be pretreated with surfactants (sometimes also with addition of alkali) at 80-100° C. and then optionally followed by the weight reduction process by using severe alkali at up to 130° C. to hydrolyze polyester fabric to make it more soft and luster appearance. Then the polyester fabric will be heat setted and dyed with disperse dyestuffs at pH 4.5-6 at up to 130° C., followed by reduction clearing with sodium hyposulphite at 60-80° C., pH 10. If necessary, these processes can be followed by finishing (post treatment) steps to further improve the textile properties, such as anti-pilling, wettability improvement or anti-static treatment.

During synthesis and drawing, cyclic or linear oligomers of polyethylene terephthalate are formed on and in the fibers. Removal of cyclic and/or linear oligomers can be accomplished by hydrolysis with one or more cutinase enzymes. The cutinase breaks the ring structure of the cyclic oligomer and break the BETEB chain to produce benzonic acid, terephthalate acid and ethelene glycol by hydrolyzing an ester bond. The resulting product can be removed under gentle conditions.

The method of the present invention of treating polyester textile with a GH61 polypeptide and a cutinase takes place during one or more of the subsequent steps of pretreatment, weight reduction, disperse dyeing or post finishing to endow the polyester fabric with at least one of the following effects: reduction of oligomer in the polyester textile, reduction of pill formation, improvement of hydrophilicity and antistatic properties etc. The method of the present invention may take place either as a separate step or in combination with any of the existing polyester processing steps.

The process of the invention is readily applicable in the textile industry as it can be carried out using existing wet processing apparatus, such as in a beam dyer, a Pad-Roll, a Jigger/Winch, a J-Box, or Pad-Steam types of apparatus. The process preferably takes place during the finishing (post treatment) step.

As used herein, the term "biopolishing", "depilling", "reduction of pill formation" and "anti-pilling" are interchangeable.

Polyester fabrics have a handle appearance that is rather hard and stiff without the application of finishing components. Some fabric surface is not smooth because small fuzzy micro-fibrils protrude from it. In addition, after a relatively short period of wear, pilling appears on the fabric surface thereby giving it an unappealing, worn look.

Biopolishing is a method to treat polyester fabrics during their manufacturing, which improves fabric quality with respect to "reduction of pill formation". The most important effects of biopolishing can be characterised by less fuzz and pilling, increased gloss/luster, improved fabric handle, increased durable softness, anti-static property and/or improved water absorbency. In the present context, the term "reduction of pill formation" is intended to mean a resistance to formation of pills on the surface of the treated fabric surface according to the method of the present invention.

For the purpose of the present invention, the pill formation may be tested according to the description of "pilling notes test" in the material and method section. The results of the test is expressed in terms of "pilling notes" which is a rating on a scale from pilling note 1 (heavy pill formation) to pilling note 5 (no pill formation), allowing ¼ pilling notes.

Since the method of biopolishing catalyze hydrolysis of the polyester fibre surface, the enzymatic action will eventually result in a weight loss of fibre or fabric. In a preferred embodiment, the biopolishing is carried out in such a way so as to obtain a controlled, partial hydrolysis of the fibre surface, i.e. a proper polishing effect without excessive loss of fabric strength.

For the purpose of the present invention, the biopolishing effect is measured under conditions as specified in Example 6, by treating PET in Launder-O-Meter with cutinase of 2.8 mg protein/gram and GH61 of 2.8 mg protein/gram of fabric at 70° C., pH 8.0 for 2 hours. In a preferred embodiment of the present invention, the treatment with cutinase and GH61 results in a pilling note of at least 2.00, preferably at least 2.25, and even more preferably at least 2.5, while preferably at the same time shows weight loss of less than 5%, preferably less than 4%, more preferably less than 3%, more preferably less than 2% and most preferably less than 1%. In preferred embodiment, compared with the treatment by cutinase of 2.8 mg protein/gram of fabric without GH61, PET treatment in Launder-O-Meter with cutinase of 2.8 mg protein/gram and GH61 of 2.8 mg protein/gram under conditions as specified in Example 6 results in increase of pilling note of 0.25.

Process Condition

GH61 polypeptides in combination with cutinase can be used during polyester textile manufacturing process, either as a separate step after any of the existing polyester manufacturing steps, or in combination with any of the existing polyester manufacturing steps like pretreatment, weight reduction, disperse dyeing or post finishing.

It is advised that a suitable liquor/textile ratio to be used in the present method may be in the range of from about 20:1 to about 1:1, preferably in the range of from about 15:1 to about 3:1, more preferably in the range of from 15:1 to 5:1 (Volume/weight, ml/mg).

The reaction time for the present invention is usually in the range of from about 10 minutes to about 8 hours. Preferably the reaction time is within the range of from about 20 minutes to about 180 minutes, more preferably the reaction time is within the range of from about 30 minutes to about 150 minutes, most preferably the reaction time is within the range of from about 45 minutes to about 120 minutes.

The pH of the reaction medium greatly depends on the enzyme(s) in question. Preferably the process of the invention is carried out at +/−1 pH unit from the pH optimum of the cutinase. Preferably, the process of the invention is carried out at a pH in the range of from about pH 3 to about pH 11, preferably in the range of from about pH 4 to about pH 10, or within the range of from about pH 6 to about pH 9.

The process temperature of the present invention is preferably selected according to the optimal temperature of the cutinase +/−10° C. Preferably the process is able to function at a temperature below 100° C., preferably below 90° C., more preferably below 80° C., and even more preferably below 75° C.

In some embodiments, the process of the present invention is conducted at the temperature range of 40-100° C., preferably 50-90° C., preferably 60-85° C., more preferably 65-80° C., and even more preferably 70-80° C.

Enzyme dosage greatly depends on the enzyme reaction time, i.e. a relatively short enzymatic reaction time necessitates a relatively increased enzyme dosage, and vice versa. In general, enzyme dosage may be stipulated in accordance with the reaction time available.

The amount of GH61 polypeptide to be used according to the method of the present invention depends on many factors and should preferably be optimized by the skilled person. According to the present invention the preferred concentration of the of GH61 polypeptide in the aqueous medium is from about 0.01 to about 50 milligram protein per gram of polyester textile, preferably 0.05-20 milligram (mg) of protein per gram (g) of polyester textile, preferably 0.1-15 milligram of protein per gram of polyester textile, more preferably 0.2-8 milligram of protein per gram of polyester textile, and even more preferably 0.2-5 milligram of protein per gram of polyester textile.

The amount of cutinase to be used according to the method of the present invention depends on many factors and should preferably be optimized by the skilled person. According to the present invention the preferred concentration of the cutinase enzyme in the aqueous medium is from about 0.01 to about 50 milligram enzyme protein per gram of polyester textile, preferably 0.05-20 milligram of enzyme protein per gram of polyester textile, more preferably 0.1-15 milligram of enzyme protein per gram of polyester textile, and even more preferably 0.2-5 milligram of enzyme protein per gram of polyester textile. Preferably, the dosage ratio between cutinase and GH61 is 1:1 to 1:0.5.

The process of the invention may further comprise the addition of one or more chemicals capable of improving the enzyme-substrate interaction (in order to improve the substrate's accessibility and/or dissolve reaction products), which chemicals may be added prior to, or simultaneously with the enzymatic treatment. Such chemicals may in particular be co-substance as described above, surfactants, wetting agents, anti-pilling agents and dispersing agents, or mixtures hereof.

The process of the invention may optionally comprise a rinsing step during which the hydrolyzed oligomers are subjected to rinsing, in particular to rinse with alkali solution. Alkal solution dissolves linear fragments of the oligomers, and may to some extent further hydrolyze these linear fragments.

The aqueous composition used in the method of the invention may further comprise one or more enzymes selected from the group consisting of lipases, esterases, laccases, peroxidase and etc.

Composition for Treating Textile

The present invention also encompasses a composition suitable for treating textile where the composition comprises a GH61 polypeptide and a cutinase.

The use of the composition of the present invention can provide the polyester fabric with at least one of the following effects: reduction of oligomer in the polyester textile, reduction of pill formation, improvement of hydrophilicity and antistatic properties etc.

The textile composition of the present invention is adapted for one or more of the polyester manufacturing processes such as pretreatment, weight reduction, disperse dyeing and post finishing, either in a separate step or in combination with any of those steps.

In the present invention, GH61 polypeptide enhances the cutinase activity by reducing the amount of cutinase required to reach the same degree of depilling.

In some embodiments of the invention, the composition containing a GH61 polypeptide and a cutinase further comprises other components, including without limitation other enzymes, as well as one or more of surfactants, bleaching agents, antifoaming agents, builder systems, and the like.

Enzymes suitable for use in the present invention include without limitation lipases, esterases, laccases, peroxidases, peroxygenase and transferases.

In one embodiment, the textile composition comprises one or more of the GH 61 polypeptides selected from the group consisting of an amino acid sequence that has a degree of identity to the mature polypeptide of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46 or SEQ ID NO: 47 of at least 60%, e.g., at least 65%, at least 70%, at least 75%, at least 80%, at least 85%, at least 90%, at least 91%, at least 92%, at least 93%, at least 94%, or at least 95%, at least 96%, at least 97%, at least 98%, at least 99%, or at least 100%.

In an even more preferred aspect, the textile composition further comprises a co-substance as described in the "Co-substance" section above. In a preferred embodiment, the co-substance is cysteine.

The textile composition can be in any form, such as a solid, liquid, paste, gel or any combination thereof.

Surfactant

In the treatment of polyester textile, a conventional surfactant may be used to improve the contact with the enzyme. The textile composition of the present invention may comprise one or more surfactants, which may be anionic and/or cationic and/or non-ionic and/or semi-polar and/or zwitterionic, or a mixture thereof. The surfactant(s) is typically present at a level of from about 0.001% to 20% by weight of composition, such as about 0.005% to about 10%, or about 0.01% to about 5%, or about 0.02% to about 1%.

More specifically, the surfactant used in the process or the composition of the present invention comprises a non-ionic surfactant. Non-limiting examples of non-ionic surfactants include alcohol ethoxylates (AE or AEO), alcohol propoxylates, propoxylated fatty alcohols (PFA), alkoxylated fatty acid alkyl esters, such as ethoxylated and/or propoxylated fatty acid alkyl esters, alkylphenol ethoxylates (APE), Triton, nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamide (PFAM), polyhydroxy alkyl fatty acid amides, or N-acyl N-alkyl derivatives of glucosamine (glucamides, GA, or fatty acid glucamide, FAGA), as well as products available under the trade names SPAN and TWEEN, and combinations thereof.

Other Enzymes

The enzymatic polyester manufacturing process as well as the textile composition may comprise one or more additional enzymes such as a lipase, esterase, laccase, peroxidase, peroxygenase and transferases.

Lipases:

Suitable lipases include those of bacterial or fungal origin. Chemically modified or protein engineered mutants are included. The lipase may for example be triacylglycerol lipase (EC3.1.1.3), phospholipase A2 (EC 3.1.1.4), Lysophospholipase (EC 3.1.1.5), Monoglyceride lipase (EC 3.1.1.23), galactolipase (EC 3.1.1.26), phospholipase A1 (EC 3.1.1.32), Lipoprotein lipase (EC 3.1.1.34). Examples include lipase from *Thermomyces*, e.g., from *T. lanuginosus* (previously named *Humicola lanuginosa*) as described in EP 258 068 and EP 305 216, a *Pseudomonas* lipase, e.g., from *P. alcaligenes* or *P. pseudoalcaligenes* (EP 218 272), *P. cepacia* (EP 331 376), *P. stutzeri* (GB 1,372,034), *P. fluorescens, Pseudomonas* sp. strain SD 705 (WO 95/06720 and WO 96/27002), *P. wisconsinensis* (WO 96/12012), a *Bacillus* lipase, e.g., from *B. subtilis* (Dartois et al., 1993, *Biochemica et Biophysica Acta*, 1131: 253-360), *B. stearothermophilus* (JP 64/744992) or *B. pumilus* (WO 91/16422).

Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079, WO 97/07202, WO 00/060063, WO2007/087508 and WO 2009/109500.

Preferred commercially available lipase enzymes include Lipolase™, Lipolase Ultra™ and Lipex™; Lecitase™, Lipolex™; Lipoclean™, Lipoprime™ (Novozymes A/S). Other commercially available lipases include Lumafast (Genencor Int Inc); Lipomax (Gist-Brocades/Genencor Int Inc) and *Bacillus* sp lipase from Solvay.

Peroxidases/Oxidases:

Suitable peroxidases/oxidases include those of plant, bacterial or fungal origin. Chemically modified or protein engineered mutants are included. Examples of useful peroxidases include peroxidases from *Coprinus*, e.g., from *C. cinereus*, and variants thereof as those described in WO 93/24618, WO 95/10602, and WO 98/15257.

Commercially available peroxidases include Guardzyme™ (Novozymes A/S).

Peroxygenase:

The term "peroxygenase" means an "unspecific peroxygenase" activity according to EC 1.11.2.1, that catalyzes insertion of an oxygen atom from $H_2O_2$ into a variety of substrates, such as nitrobenzodioxole. Examples of useful peroxygenase include peroxygenase described in WO 2008/119780.

The present methods and compositions are further described in the following numbered paragraphs.

1. A method for treating polyester textile with a glycosyl hydrolase family 61 polypeptide in the presence of a cutinase in an aqueous solution.

2. In some embodiments of the method of paragraph 1, wherein the textile is yarn, fabric or garment.

3. In some embodiments of the method of paragraph 1 or 2, wherein the polyester is PET.

4. In some embodiments of the method of paragraph 1, wherein the aqueous solution further comprises one or more enzymes selected from the group consisting of lipases, esterases, laccases, peroxidases, peroxygenase and transferases.

5. In some embodiments of the method of any of the preceding paragraphs, wherein a co-substance is used together with a glycosyl hydrolase family 61; preferably the co-substance is cysteine.

6. In some embodiments of the method of any of the preceding paragraphs, wherein the glycosyl hydrolase family 61 polypeptide is applied in the range of from 0.01 to about 50 milligram protein per gram of polyester textile, preferably 0.05-20 milligram of protein per gram of polyester textile, preferably 0.1-15 milligram of protein per gram of polyester textile, more preferably 0.2-8 milligram of protein per gram of polyester textile, and even more preferably 0.25-5 milligram of protein per gram of polyester textile.

7. In some embodiments of the method of any of the preceding paragraphs, wherein the cutinase is applied in the range of from about 0.01 to about 50 milligram enzyme protein per gram of polyester textile, preferably 0.05-20 milligram of enzyme protein per gram of polyester textile, more preferably 0.1-15 milligram of enzyme protein per gram of polyester textile, and even more preferably 0.2-5 milligram of enzyme protein per gram of polyester textile.

8. In some embodiments of the method of any of the preceding paragraphs, wherein the method is conducted in the pH range of from about pH 3 to about pH 11, preferably in the range of from about pH 4 to about pH 10, or within the range of from about pH 6 to about pH 9.

9. In some embodiments of the method of any of the preceding paragraphs, wherein the method is conducted in the temperature range of 40-100° C., preferably 50-90° C., preferably 60-85° C., more preferably 65-80° C., and even more preferably 70-80° C.

10. In some embodiments of the method of any of the preceding paragraphs, wherein the method is conducted for about 10 minutes to about 8 hours, preferably about 20 minutes to about 180 minutes, more preferably about 30 minutes to about 150 minutes, more preferably about 45 minutes to about 120 minutes.

11. In some embodiments of the method of any of the preceding paragraphs, wherein the method for treating polyester textile is the manufacture of a polyester textile, especially manufacture of a polyester fabric.

12. In some embodiments of the method of paragraph 11, wherein the method is combined with any of the existing polyester fabric manufacturing steps.

13. In some embodiments of the method of any of the preceding paragraphs, wherein the cutinase has BETEB hydrolysis activity.

14. In some embodiments of the method of any of the preceding paragraphs, wherein the cutinase is at least 90% sequence identity to SEQ ID NO:1, or comprising a substitution, deletion, and/or insertion of one or more (or several) amino acids of SEQ ID NO: 1.

15. In some embodiments of the method of any of the preceding paragraphs, wherein the glycosyl hydrolase family 61 polypeptide has having cutinase enhancing activity when measured according to the conditions of Example 4.

16. In some embodiments of the method of any of the preceding paragraphs, wherein the glycosyl hydrolase family 61 polypeptide is at least 90% sequence identity to the mature polypeptide of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46 or SEQ ID NO: 47.

17. A composition for treating a textile comprising a glycosyl hydrolase family 61 polypeptide and a cutinase.

18. In some embodiments of the composition of paragraph 17, wherein the composition further comprises one or more enzymes selected from the group consisting of lipases, esterases, laccases, peroxidases, peroxygenase and transferases.

19. In some embodiments of the composition of paragraph 17 or 18, wherein the composition further comprises a co-substance; preferably the co-substance is cysteine.

20. In some embodiments of the composition of any of the paragraph 17-19, wherein the composition further comprises a surfactant, preferably a non-ionic surfactant.

21. Use of a glycosyl hydrolase family 61 polypeptide to boost the effect of a cutinase on a polyester textile.

22. In some embodiments of the use of paragraph 21, wherein the effect is to reduce pill formation on a polyester textile.

23. In some embodiments of the use of paragraph 21 or 22, wherein the pilling note increase by at least 0.125, more preferably at least 0.250, more preferably at least 0.375, more preferably at least 0.500, more preferably at least 0.625, even more preferably at least 0.750 as compared to the pilling note when the cutinase is used without GH61 under conditions as specified in Example 6.

24. In some embodiments of the use of paragraph 21, wherein the effect is to reduce depositing of cyclic or linear oligomers of polyethylene terephthalate on machinery and/or textile when compared to the same process run under the same conditions without GH61.

25. In some embodiments of the use of paragraph 24, wherein the oligomers are acid-bis-2-benzoyloxy-ethylesther and/or triethylene terephthalate.

EXAMPLES

Materials & Methods

Proteins

Cutinase A: variant of cutinase from *Humicola. Insolens*, with substitutions E6Q+A14P+E47K+R51P+E179Q+G8D+N15D+S48E+A88H+N91H+A130V+R189V on the parent *H. insolens* cutinase of SEQ ID NO: 1 (cutinase A described in WO 2001/092502)

Cutinase B: variant of cutinase from *Humicola. Insolens*, with substitutions E6Q+A14P+E47K+R51P+E179Q+G8D+N15D+T29M+S48E+A88H+N91H+A130V+T166I+L167P+R189V on the parent *H. insolens* cutinase of SEQ ID NO: 1 (cutinase B described in WO 2001/092502)

Mature polypeptide of Af GH61: *Aspergillus fumigatus* GH61B polypeptide shown as amino acids of 22 to 250 of SEQ ID NO: 16 (described in US 2010124769)

Mature polypeptide of Ta GH61: *Thermoascus aurantiacus* GH61A polypeptide shown as amino acids 22 to 249 of SEQ ID NO: 8 (described in WO 2005/074656)

Mature polypeptide of Nc GH61: *Neurospora crassa* GH61 polypeptide shown as amino acid 21-330 of SEQ ID NO: 47 (described in WO2011080267)

Mature polypeptide of Ts GH61: *Talaromyces stipitatus* GH61 polypeptide shown as amino acids of 22 to 320 SEQ ID NO: 46 (UNIPROT: B8M2G3)

Chemicals

Triton X-100 (Beijing Kehaoze Biotechnology Co., Ltd. China)

BETEB (Terephthalic acid-bis-2-benzoyloxy-ethylesther)

PET (polyethylene terephthalate, 100% Dacron® Type 64 style, Staple woven PET fabric, commercially available from SDL.)

Reagents/Substrates

Britton-Robinson Buffer: Titrate the acidic mixture of 0.04 M $H_3BO_3$, 0.04 M $H_3PO_4$ and 0.04 M $CH_3COOH$ to the desired pH with 0.2 M NaOH.

4 mM Britton-Robinson buffer is obtained by 10-time dilution of the Britton-Robinson buffer above and then titrate the solution with NaOH to desired pH.

2.5% BETEB substrate: 2.5 g BETEB+100 ml deionized water+0.5 ml 1% Triton-X 100

OD Absorbance and pH Measurement

Cutinases A and B were used to hydrolyze PET or BETEB in eppendorf tubes. The hydrolysis products were terephthalate and its esters which had characteristic absorbance peaks around 254 nm (UV). Therefore the OD absorbance at 254 nm reflects the hydrolytic activity of enzymes towards polyesters. The higher the OD absorbance at 254 nm is, the stronger is the enzyme activity towards PET or BETEB. OD at 254 nm is read in SpectraMax M2 Microplate Reader (Molecular Devices, LLC.). If the absorbance is beyond the effective range of the Reader of 1.5, the solution will be diluted. Dilution ×15 means the solution has been diluted by 15 times.

The hydrolysis product terephthalate is acidic and will thus decrease the pH of solution, therefore the pH change before and after the reaction is a parameter for testing the activity of enzymes.

Weight Loss Determination

The swatches were placed in the conditioned room (65%+/−5% humidity, 20+/−1° C.) for 24 hours before they were numbered, weighed by the analytical balance (for samples below 100 g) or a precision balance (for samples over 100 g) and recorded. After treatment, all samples were tumbled dried (AEG, LAVATHERM 37700, Germany) for 1 hour and conditioned for 24 hours in the same conditioned room as above. For each sample, the weight loss was defined as below:

Weight loss=(weight before treatment−weight after treatment)/weight before treatment×(100%)

Pilling Notes Test

Fabrics including treated and untreated which had been pre-conditioned in norm climate (65% humidity, 20° C.) for at least 24 hours were tested for the pilling notes with Nu-Martindale Tester (James H. Heal Co. Ltd, England), with untreated fabrics of the same type as the abraded fabrics. A standard pilling test (Swiss Norm (SN) 198525) was carried out after 2000 Revolutions by marking from 1-5, with the meaning defined as below, where 1 shows poor anti-pilling and 5 shows excellent anti-pilling property. Thus the higher the Martindale pilling notes score the more effective the biopolishing treatment.

| Note 5: | No pilling |
| Note 4: | Slight Pilling |
| Note 3: | Moderate Pilling |
| Note 2: | Distinct Pilling |
| Note 1: | Heavy Pilling |

½, ¼ notes are allowed

To make the test result more reliable, 3 separate readings were carried out by different persons for each sample, and the average of the 3 readings was adopted as the final result of pilling notes.

Protein Content

The protein concentration in an enzyme product or polypeptide product used in the present examples can be measured with BCA™ Protein Assay Kit (product number 23225, commercial available from Thermo Fisher Scientific Inc.) according to the product manual.

Example 1

BETEB-Agar Plate for Evaluation of the Cutinase Activity

BETEB was hydrolyzed by cutinase into more soluble agents. Thus, after hydrolysis by enzyme, there were transparent zones on the plates poured with the mixture of Agar and BETEB.

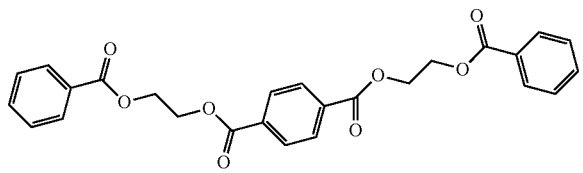 [SMILES: O=C(OCCOC(=O)c1ccc(C(=O)OCCOC(=O)c2ccccc2)cc1)c1ccccc1]

BETEB Molecule Structure

Hydrolysis of BETEB will produce

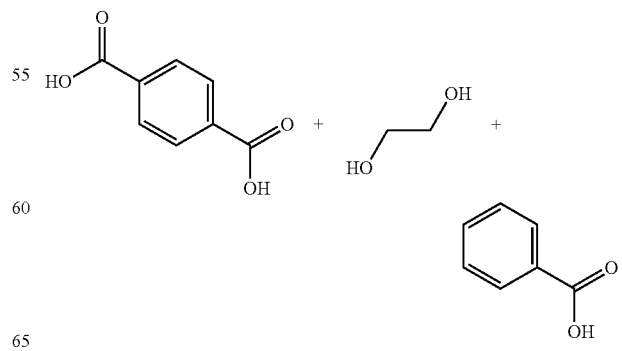

Cutinase activity was measured by the below process:

a) BETEB solution preparation: 5 ml 100% ethanol was added into a glass bottle with a plug, 20 mg BETEB was added into the ethanol and then the bottle was placed in a 60° C. water bath to dissolve the BETEB.

b) 1.5% agar solution was prepared by adding 0.75 g agar into 45 ml Tris-HCl buffer (25 mM, pH 7.0), and then placing the baker in a Microwave oven heating twice for 30 seconds to dissolve the Agar.

c) The agar solution was cooled down to 60° C. and mixed with the BETEB solution prepared in step a. The mixture was poured into a petri dish.

d) Small holes were dug in the petri dish with a tip of 6 mm diameter or puncher.

e) Enzyme sample of 30 microgram/ml was added into the petri dish by a tip with 75 microliter (ul) enzyme sample for each hole. The petri dish was placed at 37° C. overnight.

Both cutinase A and cutinase B showed transparent zones in the area around the holes, as BETEB was hydrolyzed by the cutinase.

Example 2

Cutinase a with GH61s for PET Treatment

In this example, two GH61s of Af GH61 and Ta GH61 were used respectively in combination with cutinase A to hydrolyze PET dots in 1.5 ml Eppendorf tubes.

PET fabric was cut into small pieces of 0.5 cm diameter with 0.005 g per piece, and two pieces were added into each Eppendorf tube. Britton-Robinson buffer (4 mM, pH 8) and 1% Triton X100 were placed in a thermomixer at 70° C. for 5 minutes to warm-up. After warm-up, cutinase and GH61 were added into the tube to make a total volume of 1 ml, wherein the final concentration of Triton X100 was 0.2 g/l, and the final concentration of cutinase and GH61 in the solution was as shown in Table 1. OD254 absorbance and pH were tested, as described in the Materials & Methods section, immediately shown as data for 0 hour in Table 1. The tubes were placed in a thermomixer to start the reaction at 1000 rpm and at 70° C. After reaction for a certain period of time as indicated in Table 1, the reaction was stopped by transferring the eppendorf tubes to an ice bath for 10 minutes. Then the eppendorf tubes were centrifuged at 13000 g/min for 10 seconds to get the supernatant for OD and pH determination. The supernatants were diluted 5 times for OD testing.

As can be seen from Table 1, after 2 hours reaction the absorbance at 254 nm is 0.629 for cutinase A alone and 0.716 for cutinase A combined with Af GH61. The pH change ("pH change" means the difference between the initial pH at 0 hour and the final pH after reaction), after 2 hours, when using cutinase A alone is 0.03 (i.e, 6.91 minus 6.88); while cutinase A and Af GH61 when used together, result in a pH change of 0.07 (i.e, 6.91 minus 6.84). The addition of the same dosage of Ta GH61 increases the absorbance at 254 nm from 0.629 to 0.774 and slightly increases the pH change from 0.03 to 0.06 (i.e, 6.85 minus 6.79).

When the reaction time was extended to 4 hour, the combination of Af GH61 and cutinase A increases the absorbance at 254 nm from 0.806 to 0.899 and increases the pH change from 0.08 to 0.11. After 4 hours with cutinase A and Ta GH61 the absorbance increases from 0.806 to 0.909 and the pH change from 0.08 to 0.10.

It is also found that with GH61 alone the absorbance at 254 nm would vary slightly. However the absorbance change from GH61s alone are less than the values when combining GH61s with cutinase A. For example, after 4 hours reaction with Af GH61 alone slightly increases the absorbance at 254 nm by 0.01 (i.e, 0.384 minus 0.374), and Cutinase A increases the absorbance by 0.388 (i.e, 0.806 minus 0.418) and the combination of Af GH61 and cutinase A lead to a significant absorbance increase of 0.505 (i.e, 0.899 minus 0.394). Therefore, the addition of GH61 to cutinase results in a synergistic effect on the increase of PET hydrolysis during PET treatment.

Example 3

Cutinase B with GH61s for PET Treatment

In this example, two GH61s were used in combination with Cutinase B respectively to hydrolyze PET fabric in Eppendorf tubes. The treatment protocol was the same as that described in example 2.

TABLE 1

Results of Cutinase A with two GH61s for PET treatment (70° C., pH 8.0, 1000 rpm, 0-4 hours)

| Enzyme | Cutinase (mg protein/ml solution) | GH61 (mg protein/ml solution) | OD 254 Absorbance (dilution × 5) | | | pH | | |
|---|---|---|---|---|---|---|---|---|
| | | | 0 h | 2 h | 4 h | 0 h | 2 h | 4 h |
| Cutinase A | 0.1 | 0 | 0.418 | 0.629 | 0.806 | 6.91 | 6.88 | 6.83 |
| Cutinase A + Af GH61 | 0.1 | 0.1 | 0.394 | 0.716 | 0.899 | 6.91 | 6.84 | 6.80 |
| Af GH61 | 0 | 0.1 | 0.374 | 0.386 | 0.384 | 7.83 | 7.81 | 7.80 |
| Cutinase A + Ta GH61 | 0.1 | 0.1 | 0.424 | 0.774 | 0.909 | 6.85 | 6.79 | 6.75 |
| TaGH61 | 0 | 0.1 | 0.334 | 0.350 | 0.376 | 7.81 | 7.78 | 7.69 |

Note:
average of triple samples for each enzyme combination in Table 1.

TABLE 2

Results of Cutinase B with GH61s for PET treatment (70° C., pH 7.0, 1000 rpm, 0-4 hours)

| Enzyme used | Cutinase (mg protein/ml solution) | GH61 (mg protein/ml solution) | OD 254 Absorbance (dilution × 5) | | | pH | | |
|---|---|---|---|---|---|---|---|---|
| | | | 0 h | 2 h | 4 h | 0 h | 2 h | 4 h |
| Cutinase B | 0.1 | 0 | 0.398 | 0.847 | 1.197 | 6.51 | 6.43 | 6.35 |
| Cutinase B + Af GH61 | 0.1 | 0.1 | 0.392 | 0.904 | 1.279 | 6.62 | 6.47 | 6.4 |
| Cutinase B + Ta GH61 | 0.1 | 0.1 | 0.396 | 0.875 | 1.255 | 6.5 | 6.38 | 6.3 |

Note:
average of triple samples for each enzyme combination in Table 2.

As can been seen from Table 2, at 2 hours, the addition of Af GH61 or Ta GH61 to Cutinase B increases the absorbance at 254 nm by 0.057 and 0.028, respectively and at 4 hours the absorbance increases by 0.082 and 0.058, respectively. Over the 2 to 4 hours there is also a slightly increase in the pH change before and after reaction. In conclusion, GH61s show a boosting effect on Cutinase B.

Example 4

Cutinase a with Two GH61s for Oligomer Treatment

BETEB is produced during PET synthesis and the treatment of PET as a kind of oligomer, which might remain in the textile fabric.

GH61 s (AfGH61 or TaGH61) were used in combination with cutinase A in 1.5 ml eppendorf tube. 40 mM Britton-Robinson buffer (pH 8) was added to make the enzyme and GH61 at a concentration of 0.05 mg enzyme protein/ml solution as shown in Table 3. The tubes were placed in a thermomixer at 70° C. for 5 minutes for warm-up. After warm-up, 100 ul 2.5% BETEB substrate was added into the enzyme solution to start the reaction. Eppendorf tubes were placed in the thermomixer at 70° C., 1000 rpm, for the time indicated in Table 3. The reaction was stopped by transferring the eppendorf tubes to ice bath for 10 minutes. The eppendorf tubes were centrifuged at 13000 g/min for 10 seconds to get the supernatant for OD and pH determination. The supernatants derived from 10 h, 20 minutes and 40 minutes reaction were diluted 5 times, while the supernatant derived from 1 hour reaction was diluted 75 times for OD testing. The data for sampling time at 0 hour in Table 3 means data tested before BETEB addition.

TABLE 3

Results of Cutinase A with two GH61s for BETEB treatment (70° C., pH 8.0, 1000 rpm, 0-1 hour)

| Enzyme used | Cutinase (mg protein/ml) | GH61 (mg protein/ml) | OD 254 Absorbance | | | | pH | | | |
|---|---|---|---|---|---|---|---|---|---|---|
| | | | 0 h (dilution × 5) | 20 min (dilution × 5) | 40 min (dilution × 5) | 1 h (dilution × 75) | 0 h | 20 min | 40 min | 1 h |
| Cutinase A | 0.05 | 0 | 0.121 | 1.126 | 2.293 | 0.892 | 7.51 | 7.35 | 7.17 | 5.94 |
| Cutinase A + Af GH61 | 0.05 | 0.05 | 0.124 | 1.200 | 2.760 | 0.977 | 7.52 | 7.35 | 7.15 | 5.94 |
| Af GH61 | 0 | 0.05 | 0.108 | 0.301 | 0.355 | 0.112 | 7.83 | 7.81 | 7.80 | 7.75 |
| Cutinase A + Ta GH61 | 0.05 | 0.05 | 0.136 | 1.312 | 2.840 | 1.011 | 7.5 | 7.31 | 6.83 | 5.86 |
| Ta GH61 | 0 | 0.05 | 0.109 | 0.316 | 0.379 | 0.090 | 7.97 | 7.87 | 7.87 | 7.87 |

Note:
average of triple samples for each enzyme combination.

As shown in Table 3, after 20 min reaction the absorbance at 254 nm is 1.126 for cutinase A alone and 1.200 for cutinase A combined with Af GH61. The pH change after 20 min when using cutinase A alone is 0.16 (i.e, 7.51 minus 7.35); while cutinase A and Af GH61 used together results in a pH change of 0.17 (i.e, 7.52 minus 7.35). The addition of the same dosage of Ta GH61 increase the absorbance at 254 nm from 1.126 to 1.312, and slightly increases the pH change from 0.16 to 0.19 (i.e, 7.5 minus 7.31).

After 40 min reaction, the absorbance at 254 nm is 2.293 for cutinase A alone and 2.760 for cutinase A combined with Af GH61. The pH change after 40 min when using cutinase A alone is 0.34 (i.e, 7.51 minus 7.17); while cutinase A and Af GH61 used together results in a pH change of 0.37 (i.e, 7.52 minus 7.15). The addition of the same dosage of Ta GH61 increases the absorbance at 254 nm from 2.293 to 2.840 and the pH change from 0.34 to 0.67 (i.e, 7.5 minus 6.83). Significant boosting effect of GH61s could be detected with BETEB as substrate when combined with cutinase A.

Example 5

Cutinase B with Four GH61s for Oligomer Treatment

Four GH61s were combined with cutinase B to hydrolyze oligomer BETEB at the dosage of 0.01 mg enzyme protein/ml solution and 0.01 mg GH61/ml solution. The treatment protocol was the same as described in example 4. The supernatants derived from 0 h and 20 minutes were diluted 5 times, while the supernatant derived from 40 minutes and 1 hour reaction was diluted 75 times for OD testing.

TABLE 4

Results of cutinase B with four GH61s for BETEB treatment (70° C., pH 8.0, 1000 rpm, 0-1 hour)

| Enzyme used | Cutinase (mg protein/ml) | GH61 (mg protein/ml) | OD 254 Absorbance | | | | pH | | | |
|---|---|---|---|---|---|---|---|---|---|---|
| | | | 0 h (dilution × 5) | 20 min (dilution × 5) | 40 min (dilution × 5) | 1 h (dilution × 75) | 0 h | 20 min | 40 min | 1 h |
| Cutinase B | 0.01 | 0 | 0.133 | 1.713 | 0.507 | 0.748 | 7.93 | 7.99 | 7.65 | 7.58 |
| Cutinase B + Af GH61 | 0.01 | 0.01 | 0.130 | 1.787 | 0.559 | 0.832 | 7.93 | 7.99 | 7.58 | 7.46 |
| Cutinase B + Ta GH61 | 0.01 | 0.01 | 0.120 | 1.755 | 0.565 | 0.790 | 7.92 | 7.95 | 7.55 | 7.47 |
| Cutinase B + Nc GH61 | 0.01 | 0.01 | 0.127 | 1.764 | 0.570 | 0.751 | 7.95 | 7.96 | 7.55 | 7.48 |
| Cutinase B + Ts GH61 | 0.01 | 0.01 | 0.124 | 1.710 | 0.551 | 0.770 | 7.95 | 7.97 | 7.55 | 7.48 |

Note:
average of triple samples for each enzyme combination.

As can be seen from Table 4, after 20 minutes reaction, the absorbance at 254 nm is 1.713 for cutinase B alone and 1.787 for cutinase B combined with Af GH61.

After 40 minutes reaction, the absorbance at 254 nm is 0.507 for cutinase B alone and 0.559 for cutinase B combined with Af GH61. The pH change after 40 minutes, when using cutinase B alone is 0.28 (i.e, 7.93 minus 7.65); while cutinase B and Af GH61 when used together results in a pH change of 0.35 (i.e, 7.93 minus 7.58). Similar results are obtained after 1 hour reaction, with OD absorbance increased from 0.748 to 0.832, pH change from 0.35 to 0.47 (i.e, 7.93 minus 7.46).

In conclusion, 4 different GH61s show boosting effect for hydrolyzing BETEB when used together with cutinase B.

Example 6

Cutinase a with Two GH61s for PET Biopolishing in LOM

PET biopolishing was carried out in a Launder-O-Meter (LOM, SDL-Atlas LP2) with cutinase and GH61s.

PET fabric was cut into rectangular pieces 5 cm wide and 10 cm long and a weight of about 1 g. The fabric was side-locked by sewing. The pieces were placed in a conditioned room (65% relative humidity, 20° C.) for 24 hours before they were numbered, weighed by the analytical balance and recorded. One conditioned piece was placed in each beaker. For each beaker, 10 small steel balls (M6M-SR-A4-80, acid proof) were used to supply the mechanical aids. Then the buffer (Britton-Robinson Buffer, pH=8) and the enzyme solutions were added according to Table 5, based on the calculation of actual fabric weights, with a liquid to fabric ratio of 10:1(v/w). OD absorbance at 254 nm and the initial pH of solution were measured, data indicated for sampling time at 0 hour.

The LOM machine was started after the temperature was chosen. The machine was set to pause when the temperature reached 70° C. Each beaker was fitted with a lid lined with 2 neoprin gaskets and close tightly with the metal clamping device. The beakers were loaded into the preheated LOM. Metal racks were used to accommodate and secure 5 beakers, in the vertical position, in each of the 4 drum positions. The LOM lid was closed and the washing program was continued and the timing was initiated. 2 hours later, all beakers were removed and the PET samples were transferred to the inactivation solution (2 g/L sodium carbonate) at 95° C. for 10 minutes. Then the fabrics were rinsed 2 times in hot water and 2 times in cold water. The PET samples were tumble-dried (AEG, LAVATHERM 37700, Germany) for 1 hour, and then the samples were conditioned for 24 hours at 20° C., 65% relative humidity prior to evaluation.

The solution from the treatment bath from each beaker was also collected and centrifuged at 13000 rpm for 1 minute, to further collect the supernatant for pH measurement and absorbance assay at 254 nm. The fabric evaluation includes weight loss and pilling note.

TABLE 5

Results of cutinase A with two GH61s for PET treatment in LOM

| Cutinase A (mg protein/g fabric) | Ta GH61 (mg protein/g fabric) | Af GH61 (mg protein/g fabric) | Average | | | |
|---|---|---|---|---|---|---|
| | | | Weight loss | pilling note | pH change | OD 254 change (dilution × 15) |
| 0 | — | — | 0 | 2.750 | 0.04 | 0.08 |
| 2.8 | — | — | 0.29% | 3.000 | — | 0.73 |
| 5.6 | — | — | 0.41% | 3.250 | 0.26 | 0.79 |
| — | 5.6 | — | 0 | 2.750 | 0.06 | 0.10 |
| 5.6 | 5.6 | — | 0.80% | 3.500 | 0.32 | 0.82 |
| — | — | 2.8 | 0 | 2.500 | 0.04 | 0.04 |
| 2.8 | — | 2.8 | 0.56% | 3.625 | 0.28 | 0.83 |

From the table above, it is apparent that when using cutinase in combination with TaGH61 or AfGH61, the application performance in LOM in terms of pilling note has been improved significantly, compared with using cutinase alone. Meanwhile, the weight loss is still in a low level of 0.8% or 0.56% when compared to fabric treated without cutinase and GH61. Consequently, there is synergy between Cutinase A and TaGH61 or AfGH61 for PET biopolishing.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

The invention claimed is:

1. A method, comprising treating a polyester textile with a glycosyl hydrolase family 61 polypeptide in the presence of a cutinase in an aqueous solution, wherein the glycosyl hydrolase family 61 polypeptide is applied in the range of from 0.01 to about 50 milligrams protein per gram of polyester textile, the cutinase is applied in the range of from about 0.01 to about 50 milligrams enzyme protein per gram of polyester textile, and the method is conducted for about 10 minutes to about 8 hours.

2. The method of claim 1, wherein the textile is yarn, fabric or garment.

3. The method of claim 1, wherein the polyester is polyethylene terephthalate.

4. The method of claim 1, wherein the aqueous solution further comprises one or more enzymes selected from the group consisting of esterases, laccases, lipases, peroxidases, peroxygenases, and transferases.

5. The method of claim 1, wherein a soluble and activating co-substance that catalyzes enzyme efficiency is used together with the glycosyl hydrolase family 61 and the co-substance is:

(i) a divalent ion selected from the group consisting of $Mn^{++}$, $Co^{++}$, $Mg^{++}$, and $Ca^{++}$, or (ii) a dioxy compound selected from the group consisting of pyrocatechol, catechol, caffeic acid, 3,4-dihydroxybenzoic acid, 4-tert-butyl-5-methoxy-1,2-benzenediol, pyrogallol, gallic acid, methyl-3,4,5-trihydroxybenzoate, 2,3,4-trihydroxybenzophenone, 2,6-dimethoxyphenol, sinapinic acid, 3,5-dihydroxybenzoic acid, 4-chloro-1,2-benzenediol, 4-nitro-1,2-benzenediol, tannic acid, ethyl gallate, methyl glycolate, dihydroxyfumaric acid, 2-butyne-1,4-diol, croconic acid, 1,3-propanediol, tartaric acid, 2,4-pentanediol, 3-ethyoxy-1,2-propanediol, 2,4,4'-trihydroxybenzophenone, cis-2-butene-1,4-diol, 3,4-dihydroxy-3-cyclobutene-1,2-dione, dihydroxyacetone, acrolein acetal, methyl-4-hydroxybenzoate, 4-hydroxybenzoic acid, and methyl-3,5-dimethoxy-4-hydroxybenzoate, or (iii) a bicyclic compound selected from the group consisting of epicatechin, quercetin, myricetin, taxifolin, kaempferol, morin, acacetin, naringenin, isorhamnetin, apigenin, cyanidin, cyanin, kuromanin, and keracyanin, or (iv) a heterocyclic compound selected from the group consisting of pyrazolyl, furanyl, imidazolyl, isoxazolyl, oxadiazolyl, oxazolyl, pyrrolyl, pyridyl, pyrimidyl, pyridazinyl, thiazolyl, triazolyl, thienyl, dihydrothienopyrazolyl, thianaphthenyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, isoindolyl, acridinyl, benzoisazolyl, dimethylhydantoin, pyrazinyl, tetrahydrofuranyl, pyrrolinyl, pyrrolidinyl, morpholinyl, indolyl, diazepinyl, azepinyl, thiepinyl, piperidinyl, oxepinyl, (1,2-dihydroxyethyl)-3,4-dihydroxyfuran-2(5H)-one, 4-hydroxy-5-methyl-3-furanone, 5-hydroxy-2(5H)-furanone, [1,2-dihydroxyethyl]furan-2,3,4(5H)-trione, α-hydroxy-γ-butyrolactone, ribonic γ-lactone, aldohexuronicaldohexuronic acid γ-lactone, gluconic acid 6-lactone, 4-hydroxycoumarin, dihydrobenzofuran, 5-(hydroxymethyl)furfural, furoin, 2(5H)-furanone, 5,6-dihydro-2H-pyran-2-one, and 5,6-dihydro-4-hydroxy-6-methyl-2H-pyran-2-one, or (v) a nitrogen-containing compound selected from the group consisting of acetone oxime, violuric acid, pyridine-2-aldoxime, 2-aminophenol, 1,2-benzenediamine, 2,2,6,6-tetramethyl-1-piperidinyloxy, 5,6,7,8-tetrahydrobiopterin, 6,7-dimethyl-5,6,7,8-tetrahydropterine, and maleamic acid, or (vi) a quinone compound selected from the group consisting of 4-benzoquinone, 1,4-naphthoquinone, 2-hydroxy-1,4-naphthoquinone, 2,3-dimethoxy-5-methyl-1,4-benzoquinone, coenzyme Q, 2,3,5,6-tetramethyl-1,4-benzoquinonem, duroquinone, 1,4- dihydroxyanthraquinone, 3-hydroxy-1-methyl-5,6-indolinedione, adrenochrome, 4-tert-butyl-5-methoxy-1,2-benzoquinone, and pyrroloquinoline quinone, or (vii) a sulfur-containing compound selected from the group consisting of ethanethiol, 2-propanethiol, 2-propene-1-thiol, 2-mercaptoethanesulfonic acid, benzenethiol, benzene-1,2-dithiol, cysteine, methionine, glutathione, and cystine.

6. The method of claim 5, wherein the co-substance is cysteine.

7. The method of claim 1, wherein the glycosyl hydrolase family 61 polypeptide is applied in the range of from 0.05-20 milligrams of protein per gram of polyester textile.

8. The method of claim 1, wherein the glycosyl hydrolase family 61 polypeptide is applied in the range of 0.2-5 milligrams of protein per gram of polyester textile.

9. The method of claim 1, wherein the cutinase is applied in the range of 0.05-20 milligrams of enzyme protein per gram of polyester textile.

10. The method of claim 1, wherein the cutinase is applied in the range of 0.2-5 milligrams of enzyme protein per gram of polyester textile.

11. The method of claim 1, wherein the method is conducted at a pH in the range of from about pH 3 to about pH 11, preferably in the range of from about pH 4 to about pH 10, or within the range of from about pH 6 to about pH 9.

12. The method of claim 1, wherein the method is conducted at a pH in the range of 3 to 11.

13. The method of claim 1, wherein the method is conducted at a pH in the range of 6 to 9.

14. The method of claim 1, wherein the method is conducted at a temperature in the range of 40-100° C.

15. The method of claim 1, wherein the method is conducted at a temperature in the range of 65-80° C.

16. The method of claim 1, wherein the method is conducted for about 20 minutes to about 180 minutes.

17. The method of claim 1, wherein the method is conducted for about 45 minutes to about 120 minutes.

18. The method of claim 1, which is carried out in a beam dyer, a Pad-Roll, a Jigger/Winch, a J-Box, or Pad-Steam types of apparatus.

19. The method of claim 1, which occurs during finishing in a process for manufacturing the polyester textile.

20. A process for manufacturing a polyester textile, comprising
 (a) knitting or weaving yarn into a fabric
 (b) treating the fabric to remove spin finish oil,
 (c) heat setting the fabric
 (d) dyeing with disperse dyestuffs,
 (e) reduction clearing with sodium hyposulphite,
 (f) a method of claim 1,
 wherein the method of claim 1 is conducted as a separate step or during any of steps (a)-(e).

* * * * *

SEQUENCE LISTING

```
<160> NUMBER OF SEQ ID NOS: 47

<210> SEQ ID NO 1
<211> LENGTH: 194
<212> TYPE: PRT
<213> ORGANISM: Humicola insolens

<400> SEQUENCE: 1

Gln Leu Gly Ala Ile Glu Asn Gly Leu Glu Ser Gly Ser Ala Asn Ala
1               5                   10                  15

Cys Pro Asp Ala Ile Leu Ile Phe Ala Arg Gly Ser Thr Glu Pro Gly
            20                  25                  30

Asn Met Gly Ile Thr Val Gly Pro Ala Leu Ala Asn Gly Leu Glu Ser
        35                  40                  45

His Ile Arg Asn Ile Trp Ile Gln Gly Val Gly Pro Tyr Asp Ala
    50                  55                  60

Ala Leu Ala Thr Asn Phe Leu Pro Arg Gly Thr Ser Gln Ala Asn Ile
65                  70                  75                  80

Asp Glu Gly Lys Arg Leu Phe Ala Leu Ala Asn Gln Lys Cys Pro Asn
                85                  90                  95

Thr Pro Val Val Ala Gly Gly Tyr Ser Gln Gly Ala Ala Leu Ile Ala
            100                 105                 110

Ala Ala Val Ser Glu Leu Ser Gly Ala Val Lys Glu Gln Val Lys Gly
        115                 120                 125

Val Ala Leu Phe Gly Tyr Thr Gln Asn Leu Gln Asn Arg Gly Gly Ile
    130                 135                 140

Pro Asn Tyr Pro Arg Glu Arg Thr Lys Val Phe Cys Asn Val Gly Asp
145                 150                 155                 160

Ala Val Cys Thr Gly Thr Leu Ile Ile Thr Pro Ala His Leu Ser Tyr
                165                 170                 175

Thr Ile Glu Ala Arg Gly Glu Ala Ala Arg Phe Leu Arg Asp Arg Ile
            180                 185                 190

Arg Ala

<210> SEQ ID NO 2
<211> LENGTH: 326
<212> TYPE: PRT
<213> ORGANISM: Thielavia terrestris

<400> SEQUENCE: 2

Met Lys Ser Phe Thr Ile Ala Ala Leu Ala Ala Leu Trp Ala Gln Glu
1               5                   10                  15

Ala Ala Ala His Ala Thr Phe Gln Asp Leu Trp Ile Asp Gly Val Asp
            20                  25                  30

Tyr Gly Ser Gln Cys Val Arg Leu Pro Ala Ser Asn Ser Pro Val Thr
        35                  40                  45

Asn Val Ala Ser Asp Asp Ile Arg Cys Asn Val Gly Thr Ser Arg Pro
```

```
            50                  55                  60
Thr Val Lys Cys Pro Val Lys Ala Gly Ser Thr Val Thr Ile Glu Met
 65                  70                  75                  80

His Gln Gln Pro Gly Asp Arg Ser Cys Ala Asn Glu Ala Ile Gly Gly
                 85                  90                  95

Asp His Tyr Gly Pro Val Met Val Tyr Met Ser Lys Val Asp Asp Ala
            100                 105                 110

Val Thr Ala Asp Gly Ser Ser Gly Trp Phe Lys Val Phe Gln Asp Ser
            115                 120                 125

Trp Ala Lys Asn Pro Ser Gly Ser Thr Gly Asp Asp Asp Tyr Trp Gly
        130                 135                 140

Thr Lys Asp Leu Asn Ser Cys Cys Gly Lys Met Asn Val Lys Ile Pro
145                 150                 155                 160

Glu Asp Ile Glu Pro Gly Asp Tyr Leu Leu Arg Ala Glu Val Ile Ala
                165                 170                 175

Leu His Val Ala Ala Ser Ser Gly Gly Ala Gln Phe Tyr Met Ser Cys
            180                 185                 190

Tyr Gln Leu Thr Val Thr Gly Ser Gly Ser Ala Thr Pro Ser Thr Val
        195                 200                 205

Asn Phe Pro Gly Ala Tyr Ser Ala Ser Asp Pro Gly Ile Leu Ile Asn
210                 215                 220

Ile His Ala Pro Met Ser Thr Tyr Val Val Pro Gly Pro Thr Val Tyr
225                 230                 235                 240

Ala Gly Gly Ser Thr Lys Ser Ala Gly Ser Ser Cys Ser Gly Cys Glu
                245                 250                 255

Ala Thr Cys Thr Val Gly Ser Gly Pro Ser Ala Thr Leu Thr Gln Pro
            260                 265                 270

Thr Ser Thr Ala Thr Ala Thr Ser Ala Pro Gly Gly Gly Gly Ser Gly
        275                 280                 285

Cys Thr Ala Ala Lys Tyr Gln Gln Cys Gly Gly Thr Gly Tyr Thr Gly
        290                 295                 300

Cys Thr Thr Cys Ala Ser Gly Ser Thr Cys Ser Ala Val Ser Pro Pro
305                 310                 315                 320

Tyr Tyr Ser Gln Cys Leu
                325

<210> SEQ ID NO 3
<211> LENGTH: 239
<212> TYPE: PRT
<213> ORGANISM: Thielavia terrestris

<400> SEQUENCE: 3

Met Arg Phe Asp Ala Leu Ser Ala Leu Ala Leu Ala Pro Leu Val Ala
 1               5                  10                  15

Gly His Gly Ala Val Thr Ser Tyr Ile Ile Gly Gly Lys Thr Tyr Pro
                20                  25                  30

Gly Tyr Glu Gly Phe Ser Pro Ala Ser Ser Pro Pro Thr Ile Gln Tyr
            35                  40                  45

Gln Trp Pro Asp Tyr Asn Pro Thr Leu Ser Val Thr Asp Pro Lys Met
        50                  55                  60

Arg Cys Asn Gly Gly Thr Ser Ala Glu Leu Ser Ala Pro Val Gln Ala
 65                  70                  75                  80

Gly Glu Asn Val Thr Ala Val Trp Lys Gln Trp Thr His Gln Gln Gly
                85                  90                  95
```

```
Pro Val Met Val Trp Met Phe Lys Cys Pro Gly Asp Phe Ser Ser
            100                 105                 110
His Gly Asp Gly Lys Gly Trp Phe Lys Ile Asp Gln Leu Gly Leu Trp
        115                 120                 125
Gly Asn Asn Leu Asn Ser Asn Asn Trp Gly Thr Ala Ile Val Tyr Lys
    130                 135                 140
Thr Leu Gln Trp Ser Asn Pro Ile Pro Lys Asn Leu Ala Pro Gly Asn
145                 150                 155                 160
Tyr Leu Ile Arg His Glu Leu Leu Ala Leu His Gln Ala Asn Thr Pro
                165                 170                 175
Gln Phe Tyr Ala Glu Cys Ala Gln Leu Val Val Ser Gly Ser Gly Ser
            180                 185                 190
Ala Leu Pro Pro Ser Asp Tyr Leu Tyr Ser Ile Pro Val Tyr Ala Pro
        195                 200                 205
Gln Asn Asp Pro Gly Ile Thr Val Asp Ile Tyr Asn Gly Gly Leu Thr
    210                 215                 220
Ser Tyr Thr Pro Pro Gly Gly Pro Val Trp Ser Gly Phe Glu Phe
225                 230                 235

<210> SEQ ID NO 4
<211> LENGTH: 258
<212> TYPE: PRT
<213> ORGANISM: Thielavia terrestris

<400> SEQUENCE: 4

Met Leu Leu Thr Ser Val Leu Gly Ser Ala Ala Leu Leu Ala Ser Gly
1               5                   10                  15
Ala Ala Ala His Gly Ala Val Thr Ser Tyr Ile Ile Ala Gly Lys Asn
            20                  25                  30
Tyr Pro Gly Tyr Gln Gly Phe Ser Pro Ala Asn Ser Pro Asn Val Ile
        35                  40                  45
Gln Trp Gln Trp His Asp Tyr Asn Pro Val Leu Ser Cys Ser Asp Ser
    50                  55                  60
Lys Leu Arg Cys Asn Gly Gly Thr Ser Ala Thr Leu Asn Ala Thr Ala
65                  70                  75                  80
Ala Pro Gly Asp Thr Ile Thr Ala Ile Trp Ala Gln Trp Thr His Ser
                85                  90                  95
Gln Gly Pro Ile Leu Val Trp Met Tyr Lys Cys Pro Gly Ser Phe Ser
            100                 105                 110
Ser Cys Asp Gly Ser Gly Ala Gly Trp Phe Lys Ile Asp Glu Ala Gly
        115                 120                 125
Phe His Gly Asp Gly Val Lys Val Phe Leu Asp Thr Glu Asn Pro Ser
    130                 135                 140
Gly Trp Asp Ile Ala Lys Leu Val Gly Gly Asn Lys Gln Trp Ser Ser
145                 150                 155                 160
Lys Val Pro Glu Gly Leu Ala Pro Gly Asn Tyr Leu Val Arg His Glu
                165                 170                 175
Leu Ile Ala Leu His Gln Ala Asn Asn Pro Gln Phe Tyr Pro Glu Cys
            180                 185                 190
Ala Gln Val Val Ile Thr Gly Ser Gly Thr Ala Gln Pro Asp Ala Ser
        195                 200                 205
Tyr Lys Ala Ala Ile Pro Gly Tyr Cys Asn Gln Asn Asp Pro Asn Ile
    210                 215                 220
Lys Val Pro Ile Asn Asp His Ser Ile Pro Gln Thr Tyr Lys Ile Pro
225                 230                 235                 240
```

```
Gly Pro Pro Val Phe Lys Gly Thr Ala Ser Lys Lys Ala Arg Asp Phe
                245                 250                 255

Thr Ala

<210> SEQ ID NO 5
<211> LENGTH: 226
<212> TYPE: PRT
<213> ORGANISM: Thielavia terrestris

<400> SEQUENCE: 5

Met Leu Ala Asn Gly Ala Ile Val Phe Leu Ala Ala Ala Leu Gly Val
1               5                   10                  15

Ser Gly His Tyr Thr Trp Pro Arg Val Asn Asp Gly Ala Asp Trp Gln
            20                  25                  30

Gln Val Arg Lys Ala Asp Asn Trp Gln Asp Asn Gly Tyr Val Gly Asp
        35                  40                  45

Val Thr Ser Pro Gln Ile Arg Cys Phe Gln Ala Thr Pro Ser Pro Ala
    50                  55                  60

Pro Ser Val Leu Asn Thr Thr Ala Gly Ser Thr Val Thr Tyr Trp Ala
65                  70                  75                  80

Asn Pro Asp Val Tyr His Pro Gly Pro Val Gln Phe Tyr Met Ala Arg
                85                  90                  95

Val Pro Asp Gly Glu Asp Ile Asn Ser Trp Asn Gly Asp Gly Ala Val
            100                 105                 110

Trp Phe Lys Val Tyr Glu Asp His Pro Thr Phe Gly Ala Gln Leu Thr
        115                 120                 125

Trp Pro Ser Thr Gly Lys Ser Ser Phe Ala Val Pro Ile Pro Pro Cys
    130                 135                 140

Ile Lys Ser Gly Tyr Tyr Leu Leu Arg Ala Glu Gln Ile Gly Leu His
145                 150                 155                 160

Val Ala Gln Ser Val Gly Gly Ala Gln Phe Tyr Ile Ser Cys Ala Gln
                165                 170                 175

Leu Ser Val Thr Gly Gly Gly Ser Thr Glu Pro Pro Asn Lys Val Ala
            180                 185                 190

Phe Pro Gly Ala Tyr Ser Ala Thr Asp Pro Gly Ile Leu Ile Asn Ile
        195                 200                 205

Tyr Tyr Pro Val Pro Thr Ser Tyr Gln Asn Pro Gly Pro Ala Val Phe
    210                 215                 220

Ser Cys
225

<210> SEQ ID NO 6
<211> LENGTH: 304
<212> TYPE: PRT
<213> ORGANISM: Thielavia terrestris

<400> SEQUENCE: 6

Met Lys Gly Leu Phe Ser Ala Ala Ala Leu Ser Leu Ala Val Gly Gln
1               5                   10                  15

Ala Ser Ala His Tyr Ile Phe Gln Gln Leu Ser Ile Asn Gly Asn Gln
            20                  25                  30

Phe Pro Val Tyr Gln Tyr Ile Arg Lys Asn Thr Asn Tyr Asn Ser Pro
        35                  40                  45

Val Thr Asp Leu Thr Ser Asp Asp Leu Arg Cys Asn Val Gly Ala Gln
    50                  55                  60
```

```
Gly Ala Gly Thr Asp Thr Val Thr Val Lys Ala Gly Asp Gln Phe Thr
 65                  70                  75                  80

Phe Thr Leu Asp Thr Pro Val Tyr His Gln Gly Pro Ile Ser Ile Tyr
                 85                  90                  95

Met Ser Lys Ala Pro Gly Ala Ala Ser Asp Tyr Asp Gly Ser Gly Gly
            100                 105                 110

Trp Phe Lys Ile Lys Asp Trp Gly Pro Thr Phe Asn Ala Asp Gly Thr
        115                 120                 125

Ala Thr Trp Asp Met Ala Gly Ser Tyr Thr Tyr Asn Ile Pro Thr Cys
    130                 135                 140

Ile Pro Asp Gly Asp Tyr Leu Leu Arg Ile Gln Ser Leu Ala Ile His
145                 150                 155                 160

Asn Pro Trp Pro Ala Gly Ile Pro Gln Phe Tyr Ile Ser Cys Ala Gln
                165                 170                 175

Ile Thr Val Thr Gly Gly Asn Gly Asn Pro Gly Pro Thr Ala Leu
            180                 185                 190

Ile Pro Gly Ala Phe Lys Asp Thr Asp Pro Gly Tyr Thr Val Asn Ile
        195                 200                 205

Tyr Thr Asn Phe His Asn Tyr Thr Val Pro Gly Pro Glu Val Phe Ser
    210                 215                 220

Cys Asn Gly Gly Gly Ser Asn Pro Pro Pro Val Ser Ser Ser Thr
225                 230                 235                 240

Pro Ala Thr Thr Thr Leu Val Thr Ser Thr Arg Thr Thr Ser Ser Thr
                245                 250                 255

Ser Ser Ala Ser Thr Pro Ala Ser Thr Gly Gly Cys Thr Val Ala Lys
            260                 265                 270

Trp Gly Gln Cys Gly Gly Asn Gly Tyr Thr Gly Cys Thr Thr Cys Ala
        275                 280                 285

Ala Gly Ser Thr Cys Ser Lys Gln Asn Asp Tyr Tyr Ser Gln Cys Leu
    290                 295                 300

<210> SEQ ID NO 7
<211> LENGTH: 317
<212> TYPE: PRT
<213> ORGANISM: Thielavia terrestris

<400> SEQUENCE: 7

Met Lys Gly Leu Ser Leu Leu Ala Ala Ala Ser Ala Ala Thr Ala His
  1               5                  10                  15

Thr Ile Phe Val Gln Leu Glu Ser Gly Gly Thr Thr Tyr Pro Val Ser
                 20                  25                  30

Tyr Gly Ile Arg Asp Pro Ser Tyr Asp Gly Pro Ile Thr Asp Val Thr
            35                  40                  45

Ser Asp Ser Leu Ala Cys Asn Gly Pro Pro Asn Pro Thr Thr Pro Ser
        50                  55                  60

Pro Tyr Ile Ile Asn Val Thr Ala Gly Thr Thr Val Ala Ala Ile Trp
 65                  70                  75                  80

Arg His Thr Leu Thr Ser Gly Pro Asp Asp Val Met Asp Ala Ser His
                 85                  90                  95

Lys Gly Pro Thr Leu Ala Tyr Leu Lys Lys Val Asp Asp Ala Leu Thr
            100                 105                 110

Asp Thr Gly Ile Gly Gly Gly Trp Phe Lys Ile Gln Glu Ala Gly Tyr
        115                 120                 125

Asp Asn Gly Asn Trp Ala Thr Ser Thr Val Ile Thr Asn Gly Gly Phe
    130                 135                 140
```

```
Gln Tyr Ile Asp Ile Pro Ala Cys Ile Pro Asn Gly Gln Tyr Leu Leu
145                 150                 155                 160

Arg Ala Glu Met Ile Ala Leu His Ala Ala Ser Thr Gln Gly Gly Ala
                165                 170                 175

Gln Leu Tyr Met Glu Cys Ala Gln Ile Asn Val Val Gly Gly Ser Gly
            180                 185                 190

Ser Ala Ser Pro Gln Thr Tyr Ser Ile Pro Gly Ile Tyr Gln Ala Thr
        195                 200                 205

Asp Pro Gly Leu Leu Ile Asn Ile Tyr Ser Met Thr Pro Ser Ser Gln
    210                 215                 220

Tyr Thr Ile Pro Gly Pro Leu Phe Thr Cys Ser Gly Ser Gly Asn
225                 230                 235                 240

Asn Gly Gly Gly Ser Asn Pro Ser Gly Gly Gln Thr Thr Ala Lys
                245                 250                 255

Pro Thr Thr Thr Thr Ala Ala Thr Thr Thr Ser Ser Ala Ala Pro Thr
                260                 265                 270

Ser Ser Gln Gly Gly Ser Ser Gly Cys Thr Val Pro Gln Trp Gln Gln
            275                 280                 285

Cys Gly Gly Ile Ser Phe Thr Gly Cys Thr Thr Cys Ala Ala Gly Tyr
            290                 295                 300

Thr Cys Lys Tyr Leu Asn Asp Tyr Tyr Ser Gln Cys Gln
305                 310                 315

<210> SEQ ID NO 8
<211> LENGTH: 249
<212> TYPE: PRT
<213> ORGANISM: Thermoascus aurantiacus

<400> SEQUENCE: 8

Met Ser Phe Ser Lys Ile Ile Ala Thr Ala Gly Val Leu Ala Ser Ala
1               5                   10                  15

Ser Leu Val Ala Gly His Gly Phe Val Gln Asn Ile Val Ile Asp Gly
                20                  25                  30

Lys Tyr Tyr Gly Gly Tyr Leu Val Asn Gln Tyr Pro Tyr Met Ser Asn
            35                  40                  45

Pro Pro Glu Val Ile Ala Trp Ser Thr Thr Ala Thr Asp Leu Gly Phe
    50                  55                  60

Val Asp Gly Thr Gly Tyr Gln Thr Pro Asp Ile Ile Cys His Arg Gly
65                  70                  75                  80

Ala Lys Pro Gly Ala Leu Thr Ala Pro Val Ser Pro Gly Gly Thr Val
                85                  90                  95

Glu Leu Gln Trp Thr Pro Trp Pro Asp Ser His His Gly Pro Val Ile
            100                 105                 110

Asn Tyr Leu Ala Pro Cys Asn Gly Asp Cys Ser Thr Val Asp Lys Thr
        115                 120                 125

Gln Leu Glu Phe Phe Lys Ile Ala Glu Ser Gly Leu Ile Asn Asp Asp
    130                 135                 140

Asn Pro Pro Gly Ile Trp Ala Ser Asp Asn Leu Ile Ala Ala Asn Asn
145                 150                 155                 160

Ser Trp Thr Val Thr Ile Pro Thr Thr Ile Ala Pro Gly Asn Tyr Val
                165                 170                 175

Leu Arg His Glu Ile Ile Ala Leu His Ser Ala Gln Asn Gln Asp Gly
            180                 185                 190

Ala Gln Asn Tyr Pro Gln Cys Ile Asn Leu Gln Val Thr Gly Gly Gly
```

```
                195                 200                 205
Ser Asp Asn Pro Ala Gly Thr Leu Gly Thr Ala Leu Tyr His Asp Thr
210                 215                 220

Asp Pro Gly Ile Leu Ile Asn Ile Tyr Gln Lys Leu Ser Ser Tyr Ile
225                 230                 235                 240

Ile Pro Gly Pro Pro Leu Tyr Thr Gly
                245

<210> SEQ ID NO 9
<211> LENGTH: 249
<212> TYPE: PRT
<213> ORGANISM: Trichoderma reesei

<400> SEQUENCE: 9

Met Lys Ser Cys Ala Ile Leu Ala Ala Leu Gly Cys Leu Ala Gly Ser
1               5                   10                  15

Val Leu Gly His Gly Gln Val Gln Asn Phe Thr Ile Asn Gly Gln Tyr
                20                  25                  30

Asn Gln Gly Phe Ile Leu Asp Tyr Tyr Tyr Gln Lys Gln Asn Thr Gly
            35                  40                  45

His Phe Pro Asn Val Ala Gly Trp Tyr Ala Glu Asp Leu Asp Leu Gly
        50                  55                  60

Phe Ile Ser Pro Asp Gln Tyr Thr Thr Pro Asp Ile Val Cys His Lys
65                  70                  75                  80

Asn Ala Ala Pro Gly Ala Ile Ser Ala Thr Ala Ala Gly Ser Asn
                85                  90                  95

Ile Val Phe Gln Trp Gly Pro Gly Val Trp Pro His Pro Tyr Gly Pro
                100                 105                 110

Ile Val Thr Tyr Val Val Glu Cys Ser Gly Ser Cys Thr Thr Val Asn
                115                 120                 125

Lys Asn Asn Leu Arg Trp Val Lys Ile Gln Glu Ala Gly Ile Asn Tyr
130                 135                 140

Asn Thr Gln Val Trp Ala Gln Gln Asp Leu Ile Asn Gln Gly Asn Lys
145                 150                 155                 160

Trp Thr Val Lys Ile Pro Ser Ser Leu Arg Pro Gly Asn Tyr Val Phe
                165                 170                 175

Arg His Glu Leu Leu Ala Ala His Gly Ala Ser Ser Ala Asn Gly Met
                180                 185                 190

Gln Asn Tyr Pro Gln Cys Val Asn Ile Ala Val Thr Gly Ser Gly Thr
            195                 200                 205

Lys Ala Leu Pro Ala Gly Thr Pro Ala Thr Gln Leu Tyr Lys Pro Thr
210                 215                 220

Asp Pro Gly Ile Leu Phe Asn Pro Tyr Thr Thr Ile Thr Ser Tyr Thr
225                 230                 235                 240

Ile Pro Gly Pro Ala Leu Trp Gln Gly
                245

<210> SEQ ID NO 10
<211> LENGTH: 232
<212> TYPE: PRT
<213> ORGANISM: Myceliophthora thermophila

<400> SEQUENCE: 10

Met Lys Phe Thr Ser Ser Leu Ala Val Leu Ala Ala Gly Ala Gln
1               5                   10                  15

Ala His Tyr Thr Phe Pro Arg Ala Gly Thr Gly Gly Ser Leu Ser Gly
```

```
                    20                  25                  30
Glu Trp Glu Val Val Arg Met Thr Glu Asn His Tyr Ser His Gly Pro
             35                  40                  45
Val Thr Asp Val Thr Ser Pro Glu Met Thr Cys Tyr Gln Ser Gly Val
 50                  55                  60
Gln Gly Ala Pro Gln Thr Val Gln Val Lys Ala Gly Ser Gln Phe Thr
 65                  70                  75                  80
Phe Ser Val Asp Pro Ser Ile Gly His Pro Gly Pro Leu Gln Phe Tyr
                 85                  90                  95
Met Ala Lys Val Pro Ser Gly Gln Thr Ala Ala Thr Phe Asp Gly Thr
            100                 105                 110
Gly Ala Val Trp Phe Lys Ile Tyr Gln Asp Gly Pro Asn Gly Leu Gly
            115                 120                 125
Thr Asp Ser Ile Thr Trp Pro Ser Ala Gly Lys Thr Glu Val Ser Val
            130                 135                 140
Thr Ile Pro Ser Cys Ile Asp Asp Gly Glu Tyr Leu Leu Arg Val Glu
145                 150                 155                 160
His Ile Ala Leu His Ser Ala Ser Ser Val Gly Gly Ala Gln Phe Tyr
                165                 170                 175
Ile Ala Cys Ala Gln Leu Ser Val Thr Gly Gly Ser Gly Thr Leu Asn
            180                 185                 190
Thr Gly Ser Leu Val Ser Leu Pro Gly Ala Tyr Lys Ala Thr Asp Pro
            195                 200                 205
Gly Ile Leu Phe Gln Leu Tyr Trp Pro Ile Pro Thr Glu Tyr Ile Asn
            210                 215                 220
Pro Gly Pro Ala Pro Val Ser Cys
225                 230

<210> SEQ ID NO 11
<211> LENGTH: 235
<212> TYPE: PRT
<213> ORGANISM: Myceliophthora thermophila

<400> SEQUENCE: 11

Met Lys Ala Leu Ser Leu Leu Ala Ala Ala Ser Ala Val Ser Ala His
 1               5                  10                  15
Thr Ile Phe Val Gln Leu Glu Ala Asp Gly Thr Arg Tyr Pro Val Ser
             20                  25                  30
Tyr Gly Ile Arg Asp Pro Ser Tyr Asp Gly Pro Ile Thr Asp Val Thr
             35                  40                  45
Ser Asn Asp Val Ala Cys Asn Gly Gly Pro Asn Pro Thr Thr Pro Ser
 50                  55                  60
Ser Asp Val Ile Thr Val Thr Ala Gly Thr Thr Val Lys Ala Ile Trp
 65                  70                  75                  80
Arg His Thr Leu Gln Ser Gly Pro Asp Asp Val Met Asp Ala Ser His
                 85                  90                  95
Lys Gly Pro Thr Leu Ala Tyr Leu Lys Lys Val Gly Asp Ala Thr Lys
            100                 105                 110
Asp Ser Gly Val Gly Gly Gly Trp Phe Lys Ile Gln Glu Asp Gly Tyr
            115                 120                 125
Asn Asn Gly Gln Trp Gly Thr Ser Thr Val Ile Ser Asn Gly Gly Glu
            130                 135                 140
His Tyr Ile Asp Ile Pro Ala Cys Ile Pro Glu Gly Gln Tyr Leu Leu
145                 150                 155                 160
```

```
Arg Ala Glu Met Ile Ala Leu His Ala Ala Gly Ser Pro Gly Gly Ala
                165                 170                 175

Gln Leu Tyr Met Glu Cys Ala Gln Ile Asn Ile Val Gly Gly Ser Gly
            180                 185                 190

Ser Val Pro Ser Ser Thr Val Ser Phe Pro Gly Ala Tyr Ser Pro Asn
        195                 200                 205

Asp Pro Gly Leu Leu Ile Asn Ile Tyr Ser Met Ser Pro Ser Ser Ser
    210                 215                 220

Tyr Thr Ile Pro Gly Pro Pro Val Phe Lys Cys
225                 230                 235

<210> SEQ ID NO 12
<211> LENGTH: 323
<212> TYPE: PRT
<213> ORGANISM: Myceliophthora thermophila

<400> SEQUENCE: 12

Met Lys Ser Phe Ala Leu Thr Thr Leu Ala Leu Ala Gly Asn Ala
1               5                   10                  15

Ala Ala His Ala Thr Phe Gln Ala Leu Trp Val Asp Gly Val Asp Tyr
                20                  25                  30

Gly Ala Gln Cys Ala Arg Leu Pro Ala Ser Asn Ser Pro Val Thr Asp
            35                  40                  45

Val Thr Ser Asn Ala Ile Arg Cys Asn Ala Asn Pro Ser Pro Ala Arg
    50                  55                  60

Gly Lys Cys Pro Val Lys Ala Gly Ser Thr Val Thr Val Glu Met His
65                  70                  75                  80

Gln Gln Pro Gly Asp Arg Ser Cys Ser Ser Glu Ala Ile Gly Ala
                85                  90                  95

His Tyr Gly Pro Val Met Val Tyr Met Ser Lys Val Ser Asp Ala Ala
            100                 105                 110

Ser Ala Asp Gly Ser Ser Gly Trp Phe Lys Val Phe Glu Asp Gly Trp
        115                 120                 125

Ala Lys Asn Pro Ser Gly Gly Ser Gly Asp Asp Tyr Trp Gly Thr
    130                 135                 140

Lys Asp Leu Asn Ser Cys Cys Gly Lys Met Asn Val Lys Ile Pro Ala
145                 150                 155                 160

Asp Leu Pro Ser Gly Asp Tyr Leu Leu Arg Ala Glu Ala Leu Ala Leu
                165                 170                 175

His Thr Ala Gly Ser Ala Gly Gly Ala Gln Phe Tyr Met Thr Cys Tyr
            180                 185                 190

Gln Leu Thr Val Thr Gly Ser Gly Ser Ala Ser Pro Pro Thr Val Ser
        195                 200                 205

Phe Pro Gly Ala Tyr Lys Ala Thr Asp Pro Gly Ile Leu Val Asn Ile
    210                 215                 220

His Ala Pro Leu Ser Gly Tyr Thr Val Pro Gly Pro Ala Val Tyr Ser
225                 230                 235                 240

Gly Gly Ser Thr Lys Lys Ala Gly Ser Ala Cys Thr Gly Cys Glu Ser
                245                 250                 255

Thr Cys Ala Val Gly Ser Gly Pro Thr Ala Thr Val Ser Gln Ser Pro
            260                 265                 270

Gly Ser Thr Ala Thr Ser Ala Pro Gly Gly Gly Gly Cys Thr Val
        275                 280                 285

Gln Lys Tyr Gln Gln Cys Gly Gly Glu Gly Tyr Thr Gly Cys Thr Asn
    290                 295                 300
```

```
Cys Ala Ser Gly Ser Thr Cys Ser Ala Val Ser Pro Pro Tyr Tyr Ser
305                 310                 315                 320

Gln Cys Val
```

<210> SEQ ID NO 13
<211> LENGTH: 310
<212> TYPE: PRT
<213> ORGANISM: Myceliophthora thermophila

<400> SEQUENCE: 13

```
Met Lys Pro Phe Ser Leu Val Ala Leu Ala Thr Ala Val Ser Gly His
1               5                   10                  15

Ala Ile Phe Gln Arg Val Ser Val Asn Gly Gln Asp Gln Gly Gln Leu
            20                  25                  30

Lys Gly Val Arg Ala Pro Ser Ser Asn Ser Pro Ile Gln Asn Val Asn
        35                  40                  45

Asp Ala Asn Met Ala Cys Asn Ala Asn Ile Val Tyr His Asp Ser Thr
50                  55                  60

Ile Ile Lys Val Pro Ala Gly Ala Arg Val Gly Ala Trp Trp Gln His
65                  70                  75                  80

Val Ile Gly Gly Pro Gln Gly Ala Asn Asp Pro Asp Asn Pro Ile Ala
                85                  90                  95

Ala Ser His Lys Gly Pro Ile Gln Val Tyr Leu Ala Lys Val Asp Asn
            100                 105                 110

Ala Ala Thr Ala Ser Pro Ser Gly Leu Arg Trp Phe Lys Val Ala Glu
        115                 120                 125

Arg Gly Leu Asn Asn Gly Val Trp Ala Val Asp Glu Leu Ile Ala Asn
130                 135                 140

Asn Gly Trp His Tyr Phe Asp Leu Pro Ser Cys Val Ala Pro Gly Gln
145                 150                 155                 160

Tyr Leu Met Arg Val Glu Leu Leu Ala Leu His Ser Ala Ser Ser Pro
                165                 170                 175

Gly Gly Ala Gln Phe Tyr Met Gly Cys Ala Gln Ile Glu Val Thr Gly
            180                 185                 190

Ser Gly Thr Asn Ser Gly Ser Asp Phe Val Ser Phe Pro Gly Ala Tyr
        195                 200                 205

Ser Ala Asn Asp Pro Gly Ile Leu Leu Ser Ile Tyr Asp Ser Ser Gly
210                 215                 220

Lys Pro Thr Asn Gly Gly Arg Ser Tyr Pro Ile Pro Gly Pro Arg Pro
225                 230                 235                 240

Ile Ser Cys Ser Gly Ser Gly Asp Gly Gly Asn Gly Gly Gly Gly
                245                 250                 255

Asp Asp Asn Asn Asn Asn Gly Gly Asn Gly Gly Gly
            260                 265                 270

Gly Gly Ser Val Pro Leu Tyr Gly Gln Cys Gly Gly Ile Gly Tyr Thr
        275                 280                 285

Gly Pro Thr Thr Cys Ala Gln Gly Thr Cys Lys Val Ser Asn Glu Tyr
290                 295                 300

Tyr Ser Gln Cys Leu Pro
305                 310
```

<210> SEQ ID NO 14
<211> LENGTH: 246
<212> TYPE: PRT
<213> ORGANISM: Myceliophthora thermophila -continued

<400> SEQUENCE: 14

Met Lys Leu Ser Leu Phe Ser Val Leu Ala Thr Ala Leu Thr Val Glu
1               5                   10                  15

Gly His Ala Ile Phe Gln Lys Val Ser Val Asn Gly Ala Asp Gln Gly
            20                  25                  30

Ser Leu Thr Gly Leu Arg Ala Pro Asn Asn Asn Pro Val Gln Asp
        35                  40                  45

Val Asn Ser Gln Asp Met Ile Cys Gly Gln Ser Gly Thr Ser Asn
50                  55                  60

Thr Ile Ile Glu Val Lys Ala Gly Asp Arg Ile Gly Ala Trp Tyr Gln
65                  70                  75                  80

His Val Ile Gly Gly Ala Gln Phe Pro Asn Asp Pro Asp Asn Pro Ile
                85                  90                  95

Ala Lys Ser His Lys Gly Pro Val Met Ala Tyr Leu Ala Lys Val Asp
            100                 105                 110

Asn Ala Ala Thr Ala Ser Lys Thr Gly Leu Lys Trp Phe Lys Ile Trp
        115                 120                 125

Glu Asp Thr Phe Asn Pro Ser Thr Lys Thr Trp Gly Val Asp Asn Leu
130                 135                 140

Ile Asn Asn Asn Gly Trp Val Tyr Phe Asn Leu Pro Gln Cys Ile Ala
145                 150                 155                 160

Asp Gly Asn Tyr Leu Leu Arg Val Glu Val Leu Ala Leu His Ser Ala
                165                 170                 175

Tyr Ser Gln Gly Gln Ala Gln Phe Tyr Gln Ser Cys Ala Gln Ile Asn
            180                 185                 190

Val Ser Gly Gly Gly Ser Phe Thr Pro Pro Ser Thr Val Ser Phe Pro
        195                 200                 205

Gly Ala Tyr Ser Ala Ser Asp Pro Gly Ile Leu Ile Asn Ile Tyr Gly
210                 215                 220

Ala Thr Gly Gln Pro Asp Asn Asn Gly Gln Pro Tyr Thr Ala Pro Gly
225                 230                 235                 240

Pro Ala Pro Ile Ser Cys
            245

<210> SEQ ID NO 15
<211> LENGTH: 354
<212> TYPE: PRT
<213> ORGANISM: Thermoascus aurantiacus

<400> SEQUENCE: 15

Met Ser Phe Ser Lys Ile Ala Ala Ile Thr Gly Ala Ile Thr Tyr Ala
1               5                   10                  15

Ser Leu Ala Ala Ala His Gly Tyr Val Thr Gly Ile Val Ala Asp Gly
            20                  25                  30

Thr Tyr Tyr Gly Gly Tyr Ile Val Thr Gln Tyr Pro Tyr Met Ser Thr
        35                  40                  45

Pro Pro Asp Val Ile Ala Trp Ser Thr Lys Ala Thr Asp Leu Gly Phe
50                  55                  60

Val Asp Pro Ser Ser Tyr Ala Ser Asp Ile Ile Cys His Lys Gly
65                  70                  75                  80

Ala Glu Pro Gly Ala Leu Ser Ala Lys Val Ala Ala Gly Gly Thr Val
                85                  90                  95

Glu Leu Gln Trp Thr Asp Trp Pro Glu Ser His Lys Gly Pro Val Ile
            100                 105                 110

Asp Tyr Leu Ala Ala Cys Asn Gly Asp Cys Ser Thr Val Asp Lys Thr
            115                 120                 125

Lys Leu Glu Phe Phe Lys Ile Asp Glu Ser Gly Leu Ile Asp Gly Ser
        130                 135                 140

Ser Ala Pro Gly Thr Trp Ala Ser Asp Asn Leu Ile Ala Asn Asn Asn
145                 150                 155                 160

Ser Trp Thr Val Thr Ile Pro Ser Thr Ile Ala Pro Gly Asn Tyr Val
                165                 170                 175

Leu Arg His Glu Ile Ile Ala Leu His Ser Ala Gly Asn Thr Asn Gly
            180                 185                 190

Ala Gln Asn Tyr Pro Gln Cys Ile Asn Leu Glu Val Thr Gly Ser Gly
        195                 200                 205

Thr Asp Thr Pro Ala Gly Thr Leu Gly Thr Glu Leu Tyr Lys Ala Thr
210                 215                 220

Asp Pro Gly Ile Leu Val Asn Ile Tyr Gln Thr Leu Thr Ser Tyr Asp
225                 230                 235                 240

Ile Pro Gly Pro Ala Leu Tyr Thr Gly Gly Ser Gly Ser Ser Ser Gly
                245                 250                 255

Ser Ser Asn Thr Ala Lys Ala Thr Thr Ser Thr Ala Ser Ser Ser Ile
            260                 265                 270

Val Thr Pro Thr Pro Val Asn Asn Pro Thr Val Thr Gln Thr Ala Val
        275                 280                 285

Val Asp Val Thr Gln Thr Val Ser Gln Asn Ala Ala Val Ala Thr Thr
290                 295                 300

Thr Pro Ala Ser Thr Ala Val Ala Thr Ala Val Pro Thr Gly Thr Thr
305                 310                 315                 320

Phe Ser Phe Asp Ser Met Thr Ser Asp Glu Phe Val Ser Leu Met Arg
                325                 330                 335

Ala Thr Val Asn Trp Leu Leu Ser Asn Lys Lys His Ala Arg Asp Leu
            340                 345                 350

Ser Tyr

<210> SEQ ID NO 16
<211> LENGTH: 250
<212> TYPE: PRT
<213> ORGANISM: Aspergillus fumigatus

<400> SEQUENCE: 16

Met Thr Leu Ser Lys Ile Thr Ser Ile Ala Gly Leu Leu Ala Ser Ala
1               5                   10                  15

Ser Leu Val Ala Gly His Gly Phe Val Ser Gly Ile Val Ala Asp Gly
            20                  25                  30

Lys Tyr Tyr Gly Gly Tyr Leu Val Asn Gln Tyr Pro Tyr Met Ser Asn
        35                  40                  45

Pro Pro Asp Thr Ile Ala Trp Ser Thr Thr Ala Thr Asp Leu Gly Phe
    50                  55                  60

Val Asp Gly Thr Gly Tyr Gln Ser Pro Asp Ile Ile Cys His Arg Asp
65                  70                  75                  80

Ala Lys Asn Gly Lys Leu Thr Ala Thr Val Ala Ala Gly Ser Gln Ile
                85                  90                  95

Glu Phe Gln Trp Thr Thr Trp Pro Glu Ser His His Gly Pro Leu Ile
            100                 105                 110

Thr Tyr Leu Ala Pro Cys Asn Gly Asp Cys Ala Thr Val Asp Lys Thr
        115                 120                 125

-continued

Thr Leu Lys Phe Val Lys Ile Ala Ala Gln Gly Leu Ile Asp Gly Ser
    130                 135                 140

Asn Pro Pro Gly Val Trp Ala Asp Asp Glu Met Ile Ala Asn Asn Asn
145                 150                 155                 160

Thr Ala Thr Val Thr Ile Pro Ala Ser Tyr Ala Pro Gly Asn Tyr Val
                165                 170                 175

Leu Arg His Glu Ile Ile Ala Leu His Ser Ala Gly Asn Leu Asn Gly
            180                 185                 190

Ala Gln Asn Tyr Pro Gln Cys Phe Asn Ile Gln Ile Thr Gly Gly Gly
        195                 200                 205

Ser Ala Gln Gly Ser Gly Thr Ala Gly Thr Ser Leu Tyr Lys Asn Thr
    210                 215                 220

Asp Pro Gly Ile Lys Phe Asp Ile Tyr Ser Asp Leu Ser Gly Gly Tyr
225                 230                 235                 240

Pro Ile Pro Gly Pro Ala Leu Phe Asn Ala
                245                 250

<210> SEQ ID NO 17
<211> LENGTH: 322
<212> TYPE: PRT
<213> ORGANISM: Penicillium pinophilum

<400> SEQUENCE: 17

Met Pro Ser Thr Lys Val Ala Ala Leu Ser Ala Val Leu Ala Leu Ala
1               5                   10                  15

Ser Thr Val Ala Gly His Gly Phe Val Gln Asn Ile Val Ile Asp Gly
            20                  25                  30

Lys Ser Tyr Ser Gly Tyr Leu Val Asn Gln Phe Pro Tyr Glu Ser Asn
        35                  40                  45

Pro Pro Ala Val Ile Gly Trp Ala Thr Thr Ala Thr Asp Leu Gly Phe
    50                  55                  60

Val Ala Pro Ser Glu Tyr Thr Asn Ala Asp Ile Ile Cys His Lys Asn
65                  70                  75                  80

Ala Thr Pro Gly Ala Leu Ser Ala Pro Val Ala Gly Gly Thr Val
            85                  90                  95

Glu Leu Gln Trp Thr Thr Trp Pro Asp Ser His His Gly Pro Val Ile
            100                 105                 110

Ser Tyr Leu Ala Asn Cys Asn Gly Asn Cys Ser Thr Val Asp Lys Thr
        115                 120                 125

Lys Leu Asp Phe Val Lys Ile Asp Gln Gly Gly Leu Ile Asp Asp Thr
    130                 135                 140

Thr Pro Pro Gly Thr Trp Ala Ser Asp Lys Leu Ile Ala Ala Asn Asn
145                 150                 155                 160

Ser Trp Thr Val Thr Ile Pro Ser Thr Ile Ala Pro Gly Asn Tyr Val
                165                 170                 175

Leu Arg His Glu Ile Ile Ala Leu His Ser Ala Gly Asn Ala Asp Gly
            180                 185                 190

Ala Gln Asn Tyr Pro Gln Cys Ile Asn Leu Glu Ile Thr Gly Ser Gly
        195                 200                 205

Thr Ala Ala Pro Ser Gly Thr Ala Gly Glu Lys Leu Tyr Thr Ser Thr
    210                 215                 220

Asp Pro Gly Ile Leu Val Asn Ile Tyr Gln Ser Leu Ser Thr Tyr Val
225                 230                 235                 240

Ile Pro Gly Pro Thr Leu Trp Ser Gly Ala Ala Asn Gly Ala Val Ala

```
                        245                 250                 255
Thr Gly Ser Ala Thr Ala Val Ala Thr Thr Ala Thr Ala Ser Ala Thr
                260                 265                 270

Ala Thr Pro Thr Thr Leu Val Thr Ser Val Ala Pro Ala Ser Ser Thr
            275                 280                 285

Phe Ala Thr Ala Val Val Thr Thr Val Ala Pro Ala Val Thr Asp Val
        290                 295                 300

Val Thr Val Thr Asp Val Val Thr Val Thr Thr Val Ile Thr Thr Thr
305                 310                 315                 320

Val Leu

<210> SEQ ID NO 18
<211> LENGTH: 444
<212> TYPE: PRT
<213> ORGANISM: Thermoascus sp.

<400> SEQUENCE: 18

Met Leu Ser Phe Ala Ser Ala Lys Ser Ala Val Leu Thr Thr Leu Leu
1               5                   10                  15

Leu Leu Gly Ser Ala Gln Ala His Thr Leu Met Thr Thr Leu Phe Val
            20                  25                  30

Asp Gly Val Asn Gln Gly Asp Gly Val Cys Ile Arg Met Asn Asn Asn
        35                  40                  45

Gly Ser Thr Ala Asn Thr Tyr Ile Gln Pro Val Thr Ser Lys Asp Ile
    50                  55                  60

Ala Cys Gly Ile Gln Gly Glu Ile Gly Ala Ala Arg Val Cys Pro Ala
65                  70                  75                  80

Lys Ala Ser Ser Thr Leu Thr Phe Gln Phe Arg Glu Gln Pro Ser Asn
                85                  90                  95

Pro Asn Ser Ala Pro Leu Asp Pro Ser His Lys Gly Pro Ala Ala Val
            100                 105                 110

Tyr Leu Lys Lys Val Asp Ser Ala Ile Ala Ser Asn Asn Ala Ala Gly
        115                 120                 125

Asp Gly Trp Phe Lys Ile Trp Glu Ser Val Tyr Asp Glu Ser Thr Gly
    130                 135                 140

Lys Trp Gly Thr Thr Lys Met Ile Glu Asn Asn Gly His Ile Ser Val
145                 150                 155                 160

Lys Val Pro Asp Asp Ile Glu Gly Gly Tyr Tyr Leu Ala Arg Thr Glu
                165                 170                 175

Leu Leu Ala Leu His Ala Ala Asn Glu Gly Asp Pro Gln Phe Tyr Val
            180                 185                 190

Gly Cys Ala Gln Leu Phe Ile Asp Ser Ala Gly Thr Ala Lys Pro Pro
        195                 200                 205

Thr Val Ser Ile Gly Glu Gly Thr Tyr Asp Leu Ser Met Pro Ala Met
    210                 215                 220

Thr Tyr Asn Ile Tyr Gln Thr Pro Leu Ala Leu Pro Tyr Pro Met Tyr
225                 230                 235                 240

Gly Pro Pro Val Tyr Thr Pro Gly Ser Gly Ser Gly Ser Gly Ser Gly
                245                 250                 255

Ser Gly Ser Ala Ser Ala Thr Arg Ser Ser Ala Ile Pro Thr Ala Thr
            260                 265                 270

Ala Val Thr Asp Cys Ser Ser Glu Glu Asp Arg Glu Asp Ser Val Met
        275                 280                 285

Ala Thr Gly Val Pro Val Ala Arg Ser Thr Leu Arg Thr Trp Val Asp
```

```
            290                 295                 300
Arg Leu Ser Trp His Gly Lys Ala Arg Glu Asn Val Lys Pro Ala Ala
305                 310                 315                 320

Arg Arg Ser Ala Leu Val Gln Thr Glu Gly Leu Lys Pro Glu Gly Cys
                325                 330                 335

Ile Phe Val Asn Gly Asn Trp Cys Gly Phe Glu Val Pro Asp Tyr Asn
                340                 345                 350

Asp Ala Glu Ser Cys Trp Ala Ala Ser Asp Asn Cys Trp Lys Gln Ser
                355                 360                 365

Asp Ser Cys Trp Asn Gln Thr Gln Pro Thr Gly Tyr Asn Asn Cys Gln
        370                 375                 380

Ile Trp Gln Asp Gln Lys Cys Lys Pro Ile Gln Asp Ser Cys Ser Gln
385                 390                 395                 400

Ser Asn Pro Thr Gly Pro Pro Asn Lys Gly Lys Asp Ile Thr Pro Thr
                405                 410                 415

Trp Pro Pro Leu Glu Gly Ser Met Lys Thr Phe Thr Lys Arg Thr Val
                420                 425                 430

Ser Tyr Arg Asp Trp Ile Met Lys Arg Lys Gly Ala
                435                 440

<210> SEQ ID NO 19
<211> LENGTH: 253
<212> TYPE: PRT
<213> ORGANISM: Penicillium sp.

<400> SEQUENCE: 19

Met Leu Ser Ser Thr Thr Arg Thr Leu Ala Phe Thr Gly Leu Ala Gly
1               5                   10                  15

Leu Leu Ser Ala Pro Leu Val Lys Ala His Gly Phe Val Gln Gly Ile
                20                  25                  30

Val Ile Gly Asp Gln Phe Tyr Ser Gly Tyr Ile Val Asn Ser Phe Pro
            35                  40                  45

Tyr Glu Ser Asn Pro Pro Val Ile Gly Trp Ala Thr Thr Ala Thr
    50                  55                  60

Asp Leu Gly Phe Val Asp Gly Thr Gly Tyr Gln Gly Pro Asp Ile Ile
65                  70                  75                  80

Cys His Arg Asn Ala Thr Pro Ala Pro Leu Thr Ala Pro Val Ala Ala
                85                  90                  95

Gly Gly Thr Val Glu Leu Gln Trp Thr Pro Trp Pro Asp Ser His His
            100                 105                 110

Gly Pro Val Ile Thr Tyr Leu Ala Pro Cys Asn Gly Asn Cys Ser Thr
        115                 120                 125

Val Asp Lys Thr Thr Leu Glu Phe Phe Lys Ile Asp Gln Gln Gly Leu
    130                 135                 140

Ile Asp Asp Thr Ser Pro Pro Gly Thr Trp Ala Ser Asp Asn Leu Ile
145                 150                 155                 160

Ala Asn Asn Asn Ser Trp Thr Val Thr Ile Pro Asn Ser Val Ala Pro
                165                 170                 175

Gly Asn Tyr Val Leu Arg His Glu Ile Ile Ala Leu His Ser Ala Asn
            180                 185                 190

Asn Lys Asp Gly Ala Gln Asn Tyr Pro Gln Cys Ile Asn Ile Glu Val
        195                 200                 205

Thr Gly Gly Gly Ser Asp Ala Pro Glu Gly Thr Leu Gly Glu Asp Leu
    210                 215                 220
```

```
Tyr His Asp Thr Asp Pro Gly Ile Leu Val Asp Ile Tyr Glu Pro Ile
225                 230                 235                 240

Ala Thr Tyr Thr Ile Pro Gly Pro Pro Glu Pro Thr Phe
                245                 250
```

<210> SEQ ID NO 20
<211> LENGTH: 246
<212> TYPE: PRT
<213> ORGANISM: Thielavia terrestris

<400> SEQUENCE: 20

```
Met Lys Phe Ser Leu Val Ser Leu Leu Ala Tyr Gly Leu Ser Val Glu
1               5                   10                  15

Ala His Ser Ile Phe Gln Arg Val Ser Val Asn Gly Gln Asp Gln Gly
                20                  25                  30

Leu Leu Thr Gly Leu Arg Ala Pro Ser Asn Asn Pro Val Gln Asp
            35                  40                  45

Val Asn Ser Gln Asn Met Ile Cys Gly Gln Ser Gly Ser Lys Ser Gln
50                  55                  60

Thr Val Ile Asn Val Lys Ala Gly Asp Arg Ile Gly Ser Leu Trp Gln
65                  70                  75                  80

His Val Ile Gly Gly Ala Gln Phe Ser Gly Asp Pro Asp Asn Pro Ile
                85                  90                  95

Ala His Ser His Lys Gly Pro Val Met Ala Tyr Leu Ala Lys Val Asp
                100                 105                 110

Asn Ala Ala Ser Ala Ser Gln Thr Gly Leu Lys Trp Phe Lys Ile Trp
            115                 120                 125

Gln Asp Gly Phe Asp Thr Ser Ser Lys Thr Trp Gly Val Asp Asn Leu
130                 135                 140

Ile Lys Asn Asn Gly Trp Val Tyr Phe His Leu Pro Gln Cys Leu Ala
145                 150                 155                 160

Pro Gly Gln Tyr Leu Leu Arg Val Glu Val Leu Ala Leu His Ser Ala
                165                 170                 175

Tyr Gln Gln Gly Gln Ala Gln Phe Tyr Gln Ser Cys Ala Gln Ile Asn
            180                 185                 190

Val Ser Gly Ser Gly Ser Phe Ser Pro Ser Gln Thr Val Ser Ile Pro
        195                 200                 205

Gly Val Tyr Ser Ala Thr Asp Pro Ser Ile Leu Ile Asn Ile Tyr Gly
        210                 215                 220

Ser Thr Gly Gln Pro Asp Asn Gly Gly Lys Ala Tyr Asn Pro Pro Gly
225                 230                 235                 240

Pro Ala Pro Ile Ser Cys
                245
```

<210> SEQ ID NO 21
<211> LENGTH: 334
<212> TYPE: PRT
<213> ORGANISM: Thielavia terrestris

<400> SEQUENCE: 21

```
Met Arg Thr Thr Phe Ala Ala Ala Leu Ala Ala Phe Ala Ala Gln Glu
1               5                   10                  15

Val Ala Gly His Ala Ile Phe Gln Gln Leu Trp His Gly Ser Ser Cys
                20                  25                  30

Val Arg Met Pro Leu Ser Asn Ser Pro Val Thr Asn Val Gly Ser Arg
            35                  40                  45
```

-continued

Asp Met Ile Cys Asn Ala Gly Thr Arg Pro Val Ser Gly Lys Cys Pro
    50                  55                  60

Val Lys Ala Gly Gly Thr Val Thr Val Glu Met His Gln Gln Pro Gly
65                  70                  75                  80

Asp Arg Ser Cys Asn Asn Glu Ala Ile Gly Ala His Trp Gly Pro
                85                  90                  95

Val Gln Val Tyr Leu Ser Lys Val Glu Asp Ala Ser Thr Ala Asp Gly
            100                 105                 110

Ser Thr Gly Trp Phe Lys Ile Phe Ala Asp Thr Trp Ser Lys Lys Ala
            115                 120                 125

Gly Ser Ser Val Gly Asp Asp Asp Asn Trp Gly Thr Arg Asp Leu Asn
130                 135                 140

Ala Cys Cys Gly Lys Met Gln Val Lys Ile Pro Ala Asp Ile Pro Ser
145                 150                 155                 160

Gly Asp Tyr Leu Leu Arg Ala Glu Ala Leu Ala Leu His Thr Ala Gly
                165                 170                 175

Gln Val Gly Gly Ala Gln Phe Tyr Met Ser Cys Tyr Gln Ile Thr Val
            180                 185                 190

Ser Gly Gly Gly Ser Ala Ser Pro Ala Thr Val Lys Phe Pro Gly Ala
            195                 200                 205

Tyr Ser Ala Asn Asp Pro Gly Ile His Ile Asn Ile His Ala Ala Val
210                 215                 220

Ser Asn Tyr Val Ala Pro Gly Pro Ala Val Tyr Ser Gly Gly Thr Thr
225                 230                 235                 240

Lys Val Ala Gly Ser Gly Cys Gln Gly Cys Glu Asn Thr Cys Lys Val
                245                 250                 255

Gly Ser Ser Pro Thr Ala Thr Ala Pro Ser Gly Lys Ser Gly Ala Gly
            260                 265                 270

Ser Asp Gly Gly Ala Gly Thr Asp Gly Gly Ser Ser Ser Ser Ser Pro
            275                 280                 285

Asp Thr Gly Ser Ala Cys Ser Val Gln Ala Tyr Gln Cys Gly Gly
            290                 295                 300

Asn Gly Tyr Ser Gly Cys Thr Gln Cys Ala Pro Gly Tyr Thr Cys Lys
305                 310                 315                 320

Ala Val Ser Pro Pro Tyr Tyr Ser Gln Cys Ala Pro Ser Ser
                325                 330

<210> SEQ ID NO 22
<211> LENGTH: 227
<212> TYPE: PRT
<213> ORGANISM: Thielavia terrestris

<400> SEQUENCE: 22

Met Lys Leu Ser Val Ala Ile Ala Val Leu Ala Ser Ala Leu Ala Glu
1               5                   10                  15

Ala His Tyr Thr Phe Pro Ser Ile Gly Asn Thr Ala Asp Trp Gln Tyr
                20                  25                  30

Val Arg Ile Thr Thr Asn Tyr Gln Ser Asn Gly Pro Val Thr Asp Val
            35                  40                  45

Thr Ser Asp Gln Ile Arg Cys Tyr Glu Arg Asn Pro Gly Thr Gly Ala
        50                  55                  60

Gln Gly Ile Tyr Asn Val Thr Ala Gly Gln Thr Ile Asn Tyr Asn Ala
65                  70                  75                  80

Lys Ala Ser Ile Ser His Pro Gly Pro Met Ser Phe Tyr Ile Ala Lys
                85                  90                  95

```
Val Pro Ala Gly Gln Thr Ala Ala Thr Trp Asp Gly Lys Gly Ala Val
            100                 105                 110

Trp Thr Lys Ile Tyr Gln Asp Met Pro Lys Phe Gly Ser Ser Leu Thr
            115                 120                 125

Trp Pro Thr Met Gly Ala Lys Ser Val Pro Val Thr Ile Pro Arg Cys
            130                 135                 140

Leu Gln Asn Gly Asp Tyr Leu Leu Arg Ala Glu His Ile Ala Leu His
145                 150                 155                 160

Ser Ala Ser Ser Val Gly Gly Ala Gln Phe Tyr Leu Ser Cys Ala Gln
            165                 170                 175

Leu Thr Val Ser Gly Gly Ser Gly Thr Trp Asn Pro Lys Asn Arg Val
            180                 185                 190

Ser Phe Pro Gly Ala Tyr Lys Ala Thr Asp Pro Gly Ile Leu Ile Asn
            195                 200                 205

Ile Tyr Tyr Pro Val Pro Thr Ser Tyr Ser Pro Gly Pro Pro Ala
            210                 215                 220

Glu Thr Cys
225

<210> SEQ ID NO 23
<211> LENGTH: 223
<212> TYPE: PRT
<213> ORGANISM: Thielavia terrestris

<400> SEQUENCE: 23

Met Lys Leu Ser Ser Gln Leu Ala Ala Leu Thr Leu Ala Ala Ala Ser
1               5                   10                  15

Val Ser Gly His Tyr Ile Phe Glu Gln Ile Ala His Gly Gly Thr Lys
            20                  25                  30

Phe Pro Pro Tyr Glu Tyr Ile Arg Arg Asn Thr Asn Tyr Asn Ser Pro
            35                  40                  45

Val Thr Ser Leu Ser Ser Asn Asp Leu Arg Cys Asn Val Gly Gly Glu
        50                  55                  60

Thr Ala Gly Asn Thr Thr Val Leu Asp Val Lys Ala Gly Asp Ser Phe
65                  70                  75                  80

Thr Phe Tyr Ser Asp Val Ala Val Tyr His Gln Gly Pro Ile Ser Leu
                85                  90                  95

Tyr Met Ser Lys Ala Pro Gly Ser Val Val Asp Tyr Asp Gly Ser Gly
            100                 105                 110

Asp Trp Phe Lys Ile His Asp Trp Gly Pro Thr Phe Ser Asn Gly Gln
            115                 120                 125

Ala Ser Trp Pro Leu Arg Asp Asn Tyr Gln Tyr Asn Ile Pro Thr Cys
            130                 135                 140

Ile Pro Asn Gly Glu Tyr Leu Leu Arg Ile Gln Ser Leu Ala Ile His
145                 150                 155                 160

Asn Pro Gly Ala Thr Pro Gln Phe Tyr Ile Ser Cys Ala Gln Val Arg
            165                 170                 175

Val Ser Gly Gly Gly Ser Ala Ser Pro Ser Pro Thr Ala Lys Ile Pro
            180                 185                 190

Gly Ala Phe Lys Ala Thr Asp Pro Gly Tyr Thr Ala Asn Ile Tyr Asn
            195                 200                 205

Asn Phe His Ser Tyr Thr Val Pro Gly Pro Ala Val Phe Gln Cys
            210                 215                 220
```

<210> SEQ ID NO 24
<211> LENGTH: 368
<212> TYPE: PRT
<213> ORGANISM: Thielavia terrestris

<400> SEQUENCE: 24

| | | | | | | | | | | | | | | |
|---|---|---|---|---|---|---|---|---|---|---|---|---|---|---|
| Met | Pro | Ser | Phe | Ala | Ser | Lys | Thr | Leu | Leu | Ser | Thr | Leu | Ala | Gly | Ala |
| 1 | | | | 5 | | | | | 10 | | | | | 15 | |
| Ala | Ser | Val | Ala | Ala | His | Gly | His | Val | Ser | Asn | Ile | Val | Ile | Asn | Gly |
| | | | 20 | | | | | 25 | | | | | 30 | | |
| Val | Ser | Tyr | Gln | Gly | Tyr | Asp | Pro | Thr | Ser | Phe | Pro | Tyr | Met | Gln | Asn |
| | | | 35 | | | | 40 | | | | | 45 | | | |
| Pro | Pro | Ile | Val | Val | Gly | Trp | Thr | Ala | Ala | Asp | Thr | Asp | Asn | Gly | Phe |
| | 50 | | | | | 55 | | | | | 60 | | | | |
| Val | Ala | Pro | Asp | Ala | Phe | Ala | Ser | Gly | Asp | Ile | Ile | Cys | His | Lys | Asn |
| 65 | | | | | 70 | | | | | 75 | | | | | 80 |
| Ala | Thr | Asn | Ala | Lys | Gly | His | Ala | Val | Val | Ala | Ala | Gly | Asp | Lys | Ile |
| | | | | 85 | | | | | 90 | | | | | 95 | |
| Phe | Ile | Gln | Trp | Asn | Thr | Trp | Pro | Glu | Ser | His | His | Gly | Pro | Val | Ile |
| | | | 100 | | | | | 105 | | | | | 110 | | |
| Asp | Tyr | Leu | Ala | Ser | Cys | Gly | Ser | Ala | Ser | Cys | Glu | Thr | Val | Asp | Lys |
| | | | 115 | | | | 120 | | | | | 125 | | | |
| Thr | Lys | Leu | Glu | Phe | Phe | Lys | Ile | Asp | Glu | Val | Gly | Leu | Val | Asp | Gly |
| | 130 | | | | | 135 | | | | | 140 | | | | |
| Ser | Ser | Ala | Pro | Gly | Val | Trp | Gly | Ser | Asp | Gln | Leu | Ile | Ala | Asn | Asn |
| 145 | | | | | 150 | | | | | 155 | | | | | 160 |
| Asn | Ser | Trp | Leu | Val | Glu | Ile | Pro | Pro | Thr | Ile | Ala | Pro | Gly | Asn | Tyr |
| | | | | 165 | | | | | 170 | | | | | 175 | |
| Val | Leu | Arg | His | Glu | Ile | Ile | Ala | Leu | His | Ser | Ala | Glu | Asn | Ala | Asp |
| | | | 180 | | | | | 185 | | | | | 190 | | |
| Gly | Ala | Gln | Asn | Tyr | Pro | Gln | Cys | Phe | Asn | Leu | Gln | Ile | Thr | Gly | Thr |
| | | | 195 | | | | 200 | | | | | 205 | | | |
| Gly | Thr | Ala | Thr | Pro | Ser | Gly | Val | Pro | Gly | Thr | Ser | Leu | Tyr | Thr | Pro |
| | 210 | | | | | 215 | | | | | 220 | | | | |
| Thr | Asp | Pro | Gly | Ile | Leu | Val | Asn | Ile | Tyr | Ser | Ala | Pro | Ile | Thr | Tyr |
| 225 | | | | | 230 | | | | | 235 | | | | | 240 |
| Thr | Val | Pro | Gly | Pro | Ala | Leu | Ile | Ser | Gly | Ala | Val | Ser | Ile | Ala | Gln |
| | | | | 245 | | | | | 250 | | | | | 255 | |
| Ser | Ser | Ser | Ala | Ile | Thr | Ala | Ser | Gly | Thr | Ala | Leu | Thr | Gly | Ser | Ala |
| | | | 260 | | | | | 265 | | | | | 270 | | |
| Thr | Ala | Pro | Ala | Ala | Ala | Ala | Thr | Thr | Ser | Thr | Thr | Asn | Ala |
| | | | 275 | | | | | 280 | | | | | 285 | | |
| Ala | Ala | Ala | Ala | Thr | Ser | Ala | Ala | Ala | Ala | Gly | Thr | Ser | Thr | Thr |
| | 290 | | | | | 295 | | | | | 300 | | | | |
| Thr | Thr | Ser | Ala | Ala | Val | Val | Gln | Thr | Ser | Ser | Ser | Ser | Ser |
| 305 | | | | | 310 | | | | | 315 | | | | | 320 |
| Ala | Pro | Ser | Ser | Ala | Ala | Ala | Ala | Thr | Thr | Ala | Ala | Ala | Ser |
| | | | | 325 | | | | | 330 | | | | | 335 | |
| Ala | Arg | Pro | Thr | Gly | Cys | Ser | Ser | Gly | Arg | Ser | Arg | Lys | Gln | Pro | Arg |
| | | | 340 | | | | | 345 | | | | | 350 | | |
| Arg | His | Ala | Arg | Asp | Met | Val | Val | Ala | Arg | Gly | Ala | Glu | Glu | Ala | Asn |
| | | | 355 | | | | | 360 | | | | | 365 | | |

<210> SEQ ID NO 25
<211> LENGTH: 330

```
<212> TYPE: PRT
<213> ORGANISM: Thielavia terrestris

<400> SEQUENCE: 25

Met Pro Pro Ala Leu Pro Gln Leu Leu Thr Thr Val Leu Thr Ala Leu
1               5                   10                  15

Thr Leu Gly Ser Thr Ala Leu Ala His Ser His Leu Ala Tyr Ile Ile
            20                  25                  30

Val Asn Gly Lys Leu Tyr Gln Gly Phe Asp Pro Arg Pro His Gln Ala
        35                  40                  45

Asn Tyr Pro Ser Arg Val Gly Trp Ser Thr Gly Ala Val Asp Asp Gly
    50                  55                  60

Phe Val Thr Pro Ala Asn Tyr Ser Thr Pro Asp Ile Ile Cys His Ile
65                  70                  75                  80

Ala Gly Thr Ser Pro Ala Gly His Ala Pro Val Arg Pro Gly Asp Arg
                85                  90                  95

Ile His Val Gln Trp Asn Gly Trp Pro Val Gly His Ile Gly Pro Val
            100                 105                 110

Leu Ser Tyr Leu Ala Arg Cys Glu Ser Asp Thr Gly Cys Thr Gly Gln
        115                 120                 125

Asn Lys Thr Ala Leu Arg Trp Thr Lys Ile Asp Asp Ser Ser Pro Thr
    130                 135                 140

Met Gln Asn Val Ala Gly Ala Gly Thr Gln Gly Glu Gly Thr Pro Gly
145                 150                 155                 160

Lys Arg Trp Ala Thr Asp Val Leu Ile Ala Ala Asn Asn Ser Trp Gln
                165                 170                 175

Val Ala Val Pro Ala Gly Leu Pro Thr Gly Ala Tyr Val Leu Arg Asn
            180                 185                 190

Glu Ile Ile Ala Leu His Tyr Ala Ala Arg Lys Asn Gly Ala Gln Asn
        195                 200                 205

Tyr Pro Leu Cys Met Asn Leu Trp Val Asp Ala Ser Gly Asp Asn Ser
    210                 215                 220

Ser Val Ala Ala Thr Thr Ala Ala Val Thr Ala Gly Gly Leu Gln Met
225                 230                 235                 240

Asp Ala Tyr Asp Ala Arg Gly Phe Tyr Lys Glu Asn Asp Pro Gly Val
                245                 250                 255

Leu Val Asn Val Thr Ala Ala Leu Ser Ser Tyr Val Val Pro Gly Pro
            260                 265                 270

Thr Val Ala Ala Gly Ala Thr Pro Val Pro Tyr Ala Gln Gln Ser Pro
        275                 280                 285

Ser Val Ser Thr Ala Ala Gly Thr Pro Val Val Val Thr Arg Thr Ser
    290                 295                 300

Glu Thr Ala Pro Tyr Thr Gly Ala Met Thr Pro Thr Val Ala Ala Arg
305                 310                 315                 320

Met Lys Gly Arg Gly Tyr Asp Arg Arg Gly
                325                 330

<210> SEQ ID NO 26
<211> LENGTH: 236
<212> TYPE: PRT
<213> ORGANISM: Thielavia terrestris

<400> SEQUENCE: 26

Met Lys Thr Phe Thr Ala Leu Leu Ala Ala Ala Gly Leu Val Ala Gly
1               5                   10                  15
```

```
His Gly Tyr Val Asp Asn Ala Thr Ile Gly Gly Gln Phe Tyr Gln Asn
                20                  25                  30

Pro Ala Val Leu Thr Phe Phe Gln Pro Asp Arg Val Ser Arg Ser Ile
         35                  40                  45

Pro Gly Asn Gly Pro Val Thr Asp Val Thr Leu Ile Asp Leu Gln Cys
 50                  55                  60

Asn Ala Asn Ser Thr Pro Ala Lys Leu His Ala Thr Ala Ala Ala Gly
 65                  70                  75                  80

Ser Asp Val Ile Leu Arg Trp Thr Leu Trp Pro Glu Ser His Val Gly
                 85                  90                  95

Pro Val Ile Thr Tyr Met Ala Arg Cys Pro Asp Thr Gly Cys Gln Asp
            100                 105                 110

Trp Met Pro Gly Thr Ser Ala Val Trp Phe Lys Ile Lys Glu Gly Gly
        115                 120                 125

Arg Asp Gly Thr Ser Asn Thr Trp Ala Asp Thr Pro Leu Met Thr Ala
    130                 135                 140

Pro Thr Ser Tyr Thr Tyr Thr Ile Pro Ser Cys Leu Lys Lys Gly Tyr
145                 150                 155                 160

Tyr Leu Val Arg His Glu Ile Ile Ala Leu His Ala Ala Tyr Thr Tyr
                165                 170                 175

Pro Gly Ala Gln Phe Tyr Pro Gly Cys His Gln Leu Asn Val Thr Gly
            180                 185                 190

Gly Gly Ser Thr Val Pro Ser Ser Gly Leu Val Ala Phe Pro Gly Ala
        195                 200                 205

Tyr Lys Gly Ser Asp Pro Gly Ile Thr Tyr Asp Ala Tyr Lys Ala Gln
    210                 215                 220

Thr Tyr Gln Ile Pro Gly Pro Ala Val Phe Thr Cys
225                 230                 235

<210> SEQ ID NO 27
<211> LENGTH: 250
<212> TYPE: PRT
<213> ORGANISM: Thielavia terrestris

<400> SEQUENCE: 27

Met Ala Leu Leu Leu Ala Gly Leu Ala Ile Leu Ala Gly Pro Ala
1               5                   10                  15

His Ala His Gly Gly Leu Ala Asn Tyr Thr Val Gly Asn Thr Trp Tyr
                20                  25                  30

Arg Gly Tyr Asp Pro Phe Thr Pro Ala Ala Asp Gln Ile Gly Gln Pro
         35                  40                  45

Trp Met Ile Gln Arg Ala Trp Asp Ser Ile Asp Pro Ile Phe Ser Val
 50                  55                  60

Asn Asp Lys Ala Leu Ala Cys Asn Thr Pro Thr Ala Pro Thr Ser
 65                  70                  75                  80

Tyr Ile Pro Ile Arg Ala Gly Glu Asn Ile Thr Ala Val Tyr Trp Tyr
                 85                  90                  95

Trp Leu His Pro Val Gly Pro Met Thr Ala Trp Leu Ala Arg Cys Asp
            100                 105                 110

Gly Asp Cys Arg Asp Ala Asp Val Asn Glu Ala Arg Trp Phe Lys Ile
        115                 120                 125

Trp Glu Ala Gly Leu Leu Ser Gly Pro Asn Leu Ala Glu Gly Met Trp
    130                 135                 140

Tyr Gln Lys Ala Phe Gln Asn Trp Asp Gly Ser Pro Asp Leu Trp Pro
145                 150                 155                 160
```

```
Val Thr Ile Pro Ala Gly Leu Lys Ser Gly Leu Tyr Met Ile Arg His
                165                 170                 175

Glu Ile Leu Ser Ile His Val Glu Asp Lys Pro Gln Phe Tyr Pro Glu
            180                 185                 190

Cys Ala His Leu Asn Val Thr Gly Gly Asp Leu Leu Pro Pro Asp
        195                 200                 205

Glu Phe Leu Val Lys Phe Pro Gly Ala Tyr Lys Glu Asp Asn Pro Ser
    210                 215                 220

Ile Lys Ile Asn Ile Tyr Ser Asp Gln Tyr Ala Asn Thr Thr Asn Tyr
225                 230                 235                 240

Thr Ile Pro Gly Gly Pro Ile Trp Asp Gly
                245                 250

<210> SEQ ID NO 28
<211> LENGTH: 478
<212> TYPE: PRT
<213> ORGANISM: Thielavia terrestris

<400> SEQUENCE: 28

Met Met Pro Ser Leu Val Arg Phe Ser Met Gly Leu Ala Thr Ala Phe
1               5                   10                  15

Ala Ser Leu Ser Thr Ala His Thr Val Phe Thr Thr Leu Phe Ile Asn
            20                  25                  30

Gly Val Asp Gln Gly Asp Gly Thr Cys Ile Arg Met Ala Lys Lys Gly
        35                  40                  45

Ser Val Cys Thr His Pro Ile Ala Gly Gly Leu Asp Ser Pro Asp Met
    50                  55                  60

Ala Cys Gly Arg Asp Gly Gln Gln Ala Val Ala Phe Thr Cys Pro Ala
65                  70                  75                  80

Pro Ala Gly Ser Lys Leu Ser Phe Glu Phe Arg Met Trp Ala Asp Ala
                85                  90                  95

Ser Gln Pro Gly Ser Ile Asp Pro Ser His Leu Gly Ser Thr Ala Ile
            100                 105                 110

Tyr Leu Lys Gln Val Ser Asn Ile Ser Ser Asp Ser Ala Ala Gly Pro
        115                 120                 125

Gly Trp Phe Lys Ile Tyr Ala Glu Gly Tyr Asp Thr Ala Ala Lys Lys
    130                 135                 140

Trp Ala Thr Glu Lys Leu Ile Asp Asn Gly Gly Leu Leu Ser Ile Glu
145                 150                 155                 160

Leu Pro Pro Thr Leu Pro Ala Gly Tyr Tyr Leu Ala Arg Ser Glu Ile
                165                 170                 175

Val Thr Ile Gln Asn Val Thr Asn Asp His Val Asp Pro Gln Phe Tyr
            180                 185                 190

Val Gly Cys Ala Gln Leu Phe Val Gln Gly Pro Thr Thr Pro Thr
        195                 200                 205

Val Pro Pro Asp Arg Leu Val Ser Ile Pro Gly His Val His Ala Ser
    210                 215                 220

Asp Pro Gly Leu Thr Phe Asn Ile Trp Arg Asp Asp Pro Ser Lys Thr
225                 230                 235                 240

Ala Tyr Thr Val Val Gly Pro Ala Pro Phe Ser Pro Thr Ala Ala Pro
                245                 250                 255

Thr Pro Thr Ser Thr Asn Thr Asn Gly Gln Gln Gln Gln Gln Gln
            260                 265                 270

Gln Ala Ile Lys Gln Thr Asp Gly Val Ile Pro Ala Asp Cys Gln Leu
```

```
                275                 280                 285
Lys Asn Ala Asn Trp Cys Gly Ala Glu Val Pro Ala Tyr Ala Asp Glu
            290                 295                 300
Ala Gly Cys Trp Ala Ser Ser Ala Asp Cys Phe Ala Gln Leu Asp Ala
305                 310                 315                 320
Cys Tyr Thr Ser Ala Pro Pro Thr Gly Ser Arg Gly Cys Arg Leu Trp
                325                 330                 335
Glu Asp Trp Cys Thr Gly Ile Gln Gln Gly Cys Arg Ala Gly Arg Trp
            340                 345                 350
Arg Gly Pro Pro Pro Phe His Gly Glu Gly Ala Ala Ala Glu Thr Ala
                355                 360                 365
Ser Ala Gly Arg Gly Gly Ala Arg Ile Ala Ala Val Ala Gly Cys Gly
370                 375                 380
Gly Gly Thr Gly Asp Met Val Glu Glu Val Phe Leu Phe Tyr Trp Asp
385                 390                 395                 400
Ala Cys Ser Gly Trp Arg Arg Ser Arg Gly Gly Gly Ser Ile Leu Ala
                405                 410                 415
Arg Leu Ile Leu His Val Leu Leu Pro Leu Leu Arg Pro Arg Arg Ala
            420                 425                 430
Pro Arg Val His Leu Leu Leu Phe His Leu Tyr Leu Asn Phe Cys Tyr
                435                 440                 445
Pro Gly Thr Ser Gly Phe Tyr Asn Arg Leu Ser Ile Lys Leu Gly Ile
            450                 455                 460
Trp Pro Ser Lys Met Ser Pro Asp Val Ala His Tyr Val Lys
465                 470                 475

<210> SEQ ID NO 29
<211> LENGTH: 230
<212> TYPE: PRT
<213> ORGANISM: Thielavia terrestris

<400> SEQUENCE: 29

Met Gln Leu Leu Val Gly Leu Leu Ala Val Ala Ala Arg Ala
1               5                   10                  15
His Tyr Thr Phe Pro Arg Leu Val Val Asn Gly Gln Pro Glu Asp Lys
                20                  25                  30
Asp Trp Ser Val Thr Arg Met Thr Lys Asn Ala Gln Ser Lys Gln Gly
            35                  40                  45
Val Gln Asp Pro Thr Ser Pro Asp Ile Arg Cys Tyr Thr Ser Gln Thr
        50                  55                  60
Ala Pro Asn Val Ala Thr Val Pro Ala Gly Ala Thr Val His Tyr Ile
65                  70                  75                  80
Ser Thr Gln Gln Ile Asn His Pro Gly Pro Thr Gln Tyr Tyr Leu Ala
                85                  90                  95
Lys Val Pro Ala Gly Ser Ser Ala Lys Thr Trp Asp Gly Ser Gly Ala
            100                 105                 110
Val Trp Phe Lys Ile Ser Thr Thr Met Pro Tyr Leu Asp Asn Asn Lys
        115                 120                 125
Gln Leu Val Trp Pro Asn Gln Asn Thr Tyr Thr Thr Val Asn Thr Thr
130                 135                 140
Ile Pro Ala Asp Thr Pro Ser Gly Glu Tyr Leu Leu Arg Val Glu Gln
145                 150                 155                 160
Ile Ala Leu His Leu Ala Ser Gln Pro Asn Gly Ala Gln Phe Tyr Leu
                165                 170                 175
```

```
Ala Cys Ser Gln Ile Gln Ile Thr Gly Gly Asn Gly Thr Pro Gly
            180                 185                 190

Pro Leu Val Ala Leu Pro Gly Ala Tyr Lys Ser Asn Asp Pro Gly Ile
        195                 200                 205

Leu Val Asn Ile Tyr Ser Met Gln Pro Gly Asp Tyr Lys Pro Pro Gly
    210                 215                 220

Pro Pro Val Trp Ser Gly
225             230

<210> SEQ ID NO 30
<211> LENGTH: 257
<212> TYPE: PRT
<213> ORGANISM: Thielavia terrestris

<400> SEQUENCE: 30

Met Lys Leu Tyr Leu Ala Ala Phe Leu Gly Ala Val Ala Thr Pro Gly
1               5                   10                  15

Ala Phe Ala His Gln Ile His Gly Ile Leu Leu Val Asn Gly Thr Glu
            20                  25                  30

Thr Pro Glu Trp Lys Tyr Val Arg Asp Val Ala Trp Glu Gly Ala Tyr
        35                  40                  45

Glu Pro Glu Lys Tyr Pro Asn Thr Glu Phe Phe Lys Thr Pro Pro Gln
    50                  55                  60

Thr Asp Ile Asn Pro Asn Ile Thr Cys Gly Arg Asn Ala Phe Asp
65                  70                  75                  80

Ser Ala Ser Lys Thr Glu Thr Ala Asp Ile Leu Ala Gly Ser Glu Val
                85                  90                  95

Gly Phe Arg Val Ser Trp Asp Gly Asn Gly Lys Tyr Gly Val Phe Trp
            100                 105                 110

His Pro Gly Pro Gly Gln Ile Tyr Leu Ser Arg Ala Pro Asn Asp Asp
        115                 120                 125

Leu Glu Asp Tyr Arg Gly Asp Gly Asp Trp Phe Lys Ile Ala Thr Gly
    130                 135                 140

Ala Ala Val Ser Asn Thr Glu Trp Leu Leu Trp Asn Lys His Asp Phe
145                 150                 155                 160

Asn Phe Thr Ile Pro Lys Thr Thr Pro Gly Lys Tyr Leu Met Arg
                165                 170                 175

Ile Glu Gln Phe Met Pro Ser Thr Val Glu Tyr Ser Gln Trp Tyr Val
            180                 185                 190

Asn Cys Ala His Val Asn Ile Ile Gly Pro Gly Gly Thr Pro Thr
        195                 200                 205

Gly Phe Ala Arg Phe Pro Gly Thr Tyr Thr Val Asp Asp Pro Gly Ile
    210                 215                 220

Lys Val Pro Leu Asn Gln Ile Val Asn Ser Gly Glu Leu Pro Gln Asp
225                 230                 235                 240

Gln Leu Arg Leu Leu Glu Tyr Lys Pro Pro Gly Pro Ala Leu Trp Thr
                245                 250                 255

Gly

<210> SEQ ID NO 31
<211> LENGTH: 251
<212> TYPE: PRT
<213> ORGANISM: Thermoascus crustaceus

<400> SEQUENCE: 31

Met Ala Phe Ser Gln Ile Met Ala Ile Thr Gly Val Phe Leu Ala Ser
```

```
1               5                  10                 15
Ala Ser Leu Val Ala Gly His Gly Phe Val Gln Asn Ile Val Ile Asp
            20                 25                 30
Gly Lys Ser Tyr Gly Gly Tyr Ile Val Asn Gln Tyr Pro Tyr Met Ser
            35                 40                 45
Asp Pro Pro Glu Val Val Gly Trp Ser Thr Thr Thr Asp Leu Gly
    50                 55                 60
Phe Val Asp Gly Thr Gly Tyr Gln Gly Pro Asp Ile Ile Cys His Arg
65                 70                 75                 80
Gly Ala Lys Pro Ala Ala Leu Thr Ala Gln Val Ala Ala Gly Gly Thr
                85                 90                 95
Val Lys Leu Glu Trp Thr Pro Trp Pro Asp Ser His His Gly Pro Val
            100                105                110
Ile Asn Tyr Leu Ala Pro Cys Asn Gly Asp Cys Ser Thr Val Asp Lys
            115                120                125
Thr Gln Leu Lys Phe Phe Lys Ile Ala Gln Ala Gly Leu Ile Asp Asp
130                135                140
Asn Ser Pro Pro Gly Ile Trp Ala Ser Asp Asn Leu Ile Ala Ala Asn
145                150                155                160
Asn Ser Trp Thr Val Thr Ile Pro Thr Thr Thr Ala Pro Gly Asn Tyr
                165                170                175
Val Leu Arg His Glu Ile Ile Ala Leu His Ser Ala Gly Asn Lys Asp
                180                185                190
Gly Ala Gln Asn Tyr Pro Gln Cys Ile Asn Leu Lys Val Thr Gly Asn
                195                200                205
Gly Ser Gly Asn Pro Pro Ala Gly Ala Leu Gly Thr Ala Leu Tyr Lys
    210                215                220
Asp Thr Asp Pro Gly Ile Leu Ile Asn Ile Tyr Gln Lys Leu Ser Ser
225                230                235                240
Tyr Val Ile Pro Gly Pro Ala Leu Tyr Thr Gly
                245                250

<210> SEQ ID NO 32
<211> LENGTH: 349
<212> TYPE: PRT
<213> ORGANISM: Thermoascus crustaceus

<400> SEQUENCE: 32

Met Ser Phe Ser Lys Ile Leu Ala Ile Ala Gly Ala Ile Thr Tyr Ala
1               5                  10                 15
Ser Ser Ala Ala Ala His Gly Tyr Val Gln Gly Ile Val Val Asp Gly
            20                 25                 30
Ser Tyr Tyr Gly Gly Tyr Met Val Thr Gln Tyr Pro Tyr Thr Ala Gln
            35                 40                 45
Pro Pro Glu Leu Ile Ala Trp Ser Thr Lys Ala Thr Asp Leu Gly Phe
    50                 55                 60
Val Asp Gly Ser Gly Tyr Thr Ser Pro Asp Ile Ile Cys His Lys Gly
65                 70                 75                 80
Ala Glu Pro Gly Ala Gln Ser Ala Lys Val Ala Ala Gly Gly Thr Val
                85                 90                 95
Glu Leu Gln Trp Thr Ala Trp Pro Glu Ser His Lys Gly Pro Val Ile
            100                105                110
Asp Tyr Leu Ala Ala Cys Asp Gly Asp Cys Ser Ser Val Asp Lys Thr
            115                120                125
```

```
Ala Leu Lys Phe Phe Lys Ile Asp Glu Ser Gly Leu Ile Asp Gly Asn
    130                 135                 140

Gly Ala Gly Thr Trp Ala Ser Asp Thr Leu Ile Lys Asn Asn Asn Ser
145                 150                 155                 160

Trp Thr Val Thr Ile Pro Ser Thr Ile Ala Ser Gly Asn Tyr Val Leu
                165                 170                 175

Arg His Glu Ile Ile Ala Leu His Ser Ala Gly Asn Lys Asp Gly Ala
            180                 185                 190

Gln Asn Tyr Pro Gln Cys Ile Asn Leu Glu Val Thr Gly Ser Gly Thr
        195                 200                 205

Glu Asn Pro Ala Gly Thr Leu Gly Thr Ala Leu Tyr Thr Asp Thr Asp
    210                 215                 220

Pro Gly Leu Leu Val Asn Ile Tyr Gln Gly Leu Ser Asn Tyr Ser Ile
225                 230                 235                 240

Pro Gly Pro Ala Leu Tyr Ser Gly Asn Ser Asp Asn Ala Gly Ser Leu
                245                 250                 255

Asn Pro Thr Thr Thr Pro Ser Ile Gln Asn Ala Ala Ala Ala Pro Ser
            260                 265                 270

Thr Ser Thr Ala Ser Val Val Thr Asp Ser Ser Ser Ala Thr Gln Thr
        275                 280                 285

Ala Ser Val Ala Ala Thr Thr Pro Ala Ser Thr Ser Ala Val Thr Ala
    290                 295                 300

Ser Pro Ala Pro Asp Thr Gly Ser Asp Val Thr Lys Tyr Leu Asp Ser
305                 310                 315                 320

Met Ser Ser Asp Glu Val Leu Thr Leu Val Arg Gly Thr Leu Ser Trp
                325                 330                 335

Leu Val Ser Asn Lys Lys His Ala Arg Asp Leu Ser His
            340                 345

<210> SEQ ID NO 33
<211> LENGTH: 436
<212> TYPE: PRT
<213> ORGANISM: Thermoascus crustaceus

<400> SEQUENCE: 33

Met Leu Ser Phe Ile Pro Thr Lys Ser Ala Ala Leu Thr Thr Leu Leu
1               5                   10                  15

Leu Leu Gly Thr Ala His Ala His Thr Leu Met Thr Thr Met Phe Val
            20                  25                  30

Asp Gly Val Asn Gln Gly Asp Gly Val Cys Ile Arg Met Asn Asn Asp
        35                  40                  45

Gly Gly Thr Ala Asn Thr Tyr Ile Gln Pro Ile Thr Ser Lys Asp Ile
    50                  55                  60

Ala Cys Gly Ile Gln Gly Glu Ile Gly Ala Ser Arg Val Cys Pro Val
65                  70                  75                  80

Lys Ala Ser Ser Thr Leu Thr Phe Gln Phe Arg Glu Gln Pro Asn Asn
                85                  90                  95

Pro Asn Ser Ser Pro Leu Asp Pro Ser His Lys Gly Pro Ala Ala Val
            100                 105                 110

Tyr Leu Lys Lys Val Asp Ser Ala Ile Ala Ser Asn Asn Ala Ala Gly
        115                 120                 125

Asp Ser Trp Phe Lys Ile Trp Glu Ser Val Tyr Asp Glu Ser Thr Gly
    130                 135                 140

Lys Trp Gly Thr Thr Lys Met Ile Glu Asn Asn Gly His Ile Ser Val
145                 150                 155                 160
```

Lys Val Pro Asp Asp Ile Glu Gly Gly Tyr Tyr Leu Ala Arg Thr Glu
            165                 170                 175

Leu Leu Ala Leu His Ser Ala Asp Gln Gly Asp Pro Gln Phe Tyr Val
            180                 185                 190

Gly Cys Ala Gln Leu Phe Ile Asp Ser Asp Gly Thr Ala Lys Pro Pro
            195                 200                 205

Thr Val Ser Ile Gly Glu Gly Thr Tyr Asp Leu Ser Met Pro Ala Met
210                 215                 220

Thr Tyr Asn Ile Trp Glu Thr Pro Leu Ala Leu Pro Tyr Pro Met Tyr
225                 230                 235                 240

Gly Pro Pro Val Tyr Thr Pro Gly Ser Gly Ser Gly Ser Val Arg Ala
            245                 250                 255

Thr Ser Ser Ser Ala Val Pro Thr Ala Thr Glu Ser Ser Phe Val Glu
            260                 265                 270

Glu Arg Ala Asn Pro Val Thr Ala Asn Ser Val Tyr Ser Ala Arg Gly
            275                 280                 285

Lys Phe Lys Thr Trp Ile Asp Lys Leu Ser Trp Arg Gly Lys Val Arg
            290                 295                 300

Glu Asn Val Arg Gln Ala Ala Gly Arg Arg Ser Thr Leu Val Gln Thr
305                 310                 315                 320

Val Gly Leu Lys Pro Lys Gly Cys Ile Phe Val Asn Gly Asn Trp Cys
            325                 330                 335

Gly Phe Glu Val Pro Asp Tyr Asn Asp Ala Glu Ser Cys Trp Ala Ala
            340                 345                 350

Ser Asp Asn Cys Trp Lys Gln Ser Asp Ala Cys Trp Asn Lys Thr Gln
            355                 360                 365

Pro Thr Gly Tyr Asn Asn Cys Gln Ile Trp Gln Asp Lys Lys Cys Lys
            370                 375                 380

Val Ile Gln Asp Ser Cys Ser Gly Pro Asn Pro His Gly Pro Pro Asn
385                 390                 395                 400

Lys Gly Lys Asp Leu Thr Pro Glu Trp Pro Pro Leu Lys Gly Ser Met
            405                 410                 415

Asp Thr Phe Ser Lys Arg Thr Ile Gly Tyr Arg Asp Trp Ile Val Arg
            420                 425                 430

Arg Arg Gly Ala
        435

<210> SEQ ID NO 34
<211> LENGTH: 344
<212> TYPE: PRT
<213> ORGANISM: Aspergillus aculeatus

<400> SEQUENCE: 34

Met Lys Tyr Ile Pro Leu Val Ile Ala Val Ala Ala Gly Leu Ala Arg
1               5                   10                  15

Pro Ala Thr Ala His Tyr Ile Phe Ser Lys Leu Val Leu Asn Gly Glu
            20                  25                  30

Ala Ser Ala Asp Trp Gln Tyr Ile Arg Glu Thr Thr Arg Ser Ile Val
            35                  40                  45

Tyr Glu Pro Thr Lys Tyr Thr Ser Thr Phe Asp Asn Leu Thr Pro Ser
            50                  55                  60

Asp Ser Asp Phe Arg Cys Asn Leu Gly Ser Phe Ser Asn Ala Ala Lys
65                  70                  75                  80

Thr Glu Val Ala Glu Val Ala Ala Gly Asp Thr Ile Ala Met Lys Leu

```
            85                  90                  95
Phe Tyr Asp Thr Ser Ile Ala His Pro Gly Pro Gly Gln Val Tyr Met
            100                 105                 110

Ser Lys Ala Pro Thr Gly Asn Val Gln Glu Tyr Gln Gly Asp Gly Asp
            115                 120                 125

Trp Phe Lys Ile Trp Glu Lys Thr Leu Cys Asn Thr Asp Gly Asp Leu
130                 135                 140

Thr Thr Glu Ala Trp Cys Thr Trp Gly Met Ser Gln Phe Glu Phe Gln
145                 150                 155                 160

Ile Pro Ala Ala Thr Pro Ala Gly Glu Tyr Leu Val Arg Ala Glu His
                165                 170                 175

Ile Gly Leu His Gly Ala Gln Ala Asn Glu Ala Glu Phe Phe Tyr Ser
            180                 185                 190

Cys Ala Gln Ile Lys Val Thr Gly Ser Gly Thr Gly Ser Pro Ser Leu
            195                 200                 205

Thr Tyr Gln Ile Pro Gly Leu Tyr Asn Asp Thr Met Thr Leu Phe Asn
            210                 215                 220

Gly Leu Asn Leu Trp Thr Asp Ser Ala Glu Lys Val Gln Leu Asp Phe
225                 230                 235                 240

Leu Glu Thr Pro Ile Gly Asp Asp Val Trp Ser Gly Ala Gly Ser Gly
                245                 250                 255

Ser Pro Ser Ala Ala Thr Ser Ser Thr Ser Gly Ala Thr Leu Ala Ala
            260                 265                 270

Gln Gly Thr Thr Thr Ser Ala Ala His Ala Gln Ala Gln Thr Thr Ile
            275                 280                 285

Thr Thr Ser Thr Ser Thr Ile Thr Ser Leu Glu Ser Ala Ser Ser Thr
            290                 295                 300

Asp Leu Val Ala Gln Tyr Gly Gln Cys Gly Gly Leu Asn Trp Ser Gly
305                 310                 315                 320

Pro Thr Glu Cys Glu Thr Pro Tyr Thr Cys Val Gln Gln Asn Pro Tyr
                325                 330                 335

Tyr His Gln Cys Val Asn Ser Cys
            340

<210> SEQ ID NO 35
<211> LENGTH: 400
<212> TYPE: PRT
<213> ORGANISM: Aspergillus aculeatus

<400> SEQUENCE: 35

Met Ser Val Ala Lys Phe Ala Gly Val Ile Leu Gly Ser Ala Ala Leu
1               5                   10                  15

Val Ala Gly His Gly Tyr Val Ser Gly Ala Val Val Asp Gly Thr Tyr
            20                  25                  30

Tyr Gly Gly Tyr Ile Val Thr Ser Tyr Pro Tyr Ser Ser Asp Pro Pro
        35                  40                  45

Glu Thr Ile Gly Trp Ser Thr Glu Ala Thr Asp Leu Gly Phe Val Asp
    50                  55                  60

Gly Ser Glu Tyr Ala Asp Ala Asp Ile Ile Cys His Lys Ser Ala Lys
65                  70                  75                  80

Pro Gly Ala Ile Ser Ala Glu Val Lys Ala Gly Gly Thr Val Glu Leu
                85                  90                  95

Gln Trp Thr Thr Trp Pro Asp Ser His His Gly Pro Val Leu Thr Tyr
            100                 105                 110
```

```
Leu Ala Asn Cys Asn Gly Asp Cys Ser Ser Val Thr Lys Thr Asp Leu
            115                 120                 125

Glu Phe Phe Lys Ile Asp Glu Ser Gly Leu Ile Asn Asp Asp Val
130                 135                 140

Pro Gly Thr Trp Ala Ser Asp Asn Leu Ile Ala Asn Asn Ser Trp
145                 150                 155                 160

Thr Val Thr Ile Pro Ser Asp Ile Ala Ala Gly Asn Tyr Val Leu Arg
                165                 170                 175

His Glu Ile Ile Ala Leu His Ser Ala Gly Asn Lys Asp Gly Ala Gln
            180                 185                 190

Asn Tyr Pro Gln Cys Leu Asn Leu Lys Val Thr Gly Gly Asp Leu
        195                 200                 205

Ala Pro Ser Gly Thr Ala Gly Glu Ser Leu Tyr Lys Asp Thr Asp Ala
210                 215                 220

Gly Ile Leu Val Asn Ile Tyr Gln Ser Leu Ser Ser Tyr Asp Ile Pro
225                 230                 235                 240

Gly Pro Ala Met Tyr Asn Ala Thr Ser Ser Ser Ser Ser Ser Ser
                245                 250                 255

Ser Ser Ser Ser Ser Ser Ser Ser Ser Ser Gly Ser Ser Ser Ser
        260                 265                 270

Ala Ala Ala Ser Ser Ser Ser Ser Ser Ser Thr Thr Ala Ala Ala
        275                 280                 285

Ala Ala Ala Thr Ser Ala Ala Ser Ser Val Thr Ser Ala Ala Gly Ser
        290                 295                 300

Val Val Thr Gln Thr Ala Thr Ala Val Glu Thr Asp Thr Ala Thr Ala
305                 310                 315                 320

Tyr Gln Thr Ser Thr Glu Val Ala Gln Val Thr Val Thr Gly Ser Ala
                325                 330                 335

Pro Gln Gln Thr Tyr Val Ala Thr Pro Ser Ser Ser Ser Ser Ala Ser
                340                 345                 350

Ser Ser Ser Ser Ala Ser Val Ser Thr Ser Thr Ser Leu Thr Ser Tyr
        355                 360                 365

Phe Glu Ser Leu Ser Ala Asp Gln Phe Leu Ser Val Leu Lys Gln Thr
370                 375                 380

Phe Thr Trp Leu Val Ser Glu Lys Lys His Ala Arg Asp Leu Ser Ala
385                 390                 395                 400

<210> SEQ ID NO 36
<211> LENGTH: 389
<212> TYPE: PRT
<213> ORGANISM: Aspergillus aculeatus

<400> SEQUENCE: 36

Met Lys Ser Ser Thr Phe Gly Met Leu Ala Leu Ala Ala Ala Ala Lys
1               5                   10                  15

Met Val Asp Ala His Thr Thr Val Phe Ala Val Trp Ile Asn Gly Glu
                20                  25                  30

Asp Gln Gly Leu Gly Asn Ser Ala Ser Gly Tyr Ile Arg Ser Pro Pro
            35                  40                  45

Ser Asn Ser Pro Val Lys Asp Val Thr Ser Thr Asp Ile Thr Cys Asn
        50                  55                  60

Val Asn Gly Asp Gln Ala Ala Ala Lys Thr Leu Ser Val Lys Gly Gly
65                  70                  75                  80

Asp Val Val Thr Phe Glu Trp His His Asp Ser Arg Asp Ala Ser Asp
                85                  90                  95
```

```
Asp Ile Ile Ala Ser Ser His Lys Gly Pro Val Met Val Tyr Met Ala
            100                 105                 110

Pro Thr Thr Ala Gly Ser Ser Gly Lys Asn Trp Val Lys Ile Ala Glu
        115                 120                 125

Asp Gly Tyr Ser Asp Gly Thr Trp Ala Val Asp Thr Leu Ile Ala Asn
    130                 135                 140

Ser Gly Lys His Asn Ile Thr Val Pro Asp Val Pro Ala Gly Asp Tyr
145                 150                 155                 160

Leu Phe Arg Pro Glu Ile Ile Ala Leu His Glu Ala Glu Asn Glu Gly
                165                 170                 175

Gly Ala Gln Phe Tyr Met Glu Cys Val Gln Phe Lys Val Thr Ser Asp
            180                 185                 190

Gly Ala Asn Thr Leu Pro Asp Gly Val Ser Leu Pro Gly Ala Tyr Ser
        195                 200                 205

Ala Thr Asp Pro Gly Ile Leu Phe Asn Met Tyr Gly Ser Phe Asp Ser
    210                 215                 220

Tyr Pro Ile Pro Gly Pro Ser Val Trp Asp Gly Thr Ser Ser Gly Ser
225                 230                 235                 240

Ser Ser Ser Ser Ser Ser Ser Ser Ser Ser Ala Ala Ala Ala
                245                 250                 255

Val Val Ala Thr Ser Ser Ser Ser Ser Ala Ser Ile Glu Ala Val
            260                 265                 270

Thr Thr Lys Gly Ala Val Ala Ala Val Ser Thr Ala Ala Val Ala
        275                 280                 285

Pro Thr Thr Thr Ala Ala Pro Thr Thr Phe Ala Thr Ala Val Ala
    290                 295                 300

Ser Thr Lys Lys Ala Thr Ala Cys Arg Asn Lys Thr Lys Ser Ser Ser
305                 310                 315                 320

Ala Ala Thr Thr Ala Ala Ala Val Ala Glu Thr Thr Ser Ser Thr Ala
                325                 330                 335

Ala Ala Thr Ala Ala Ala Ser Ser Ala Ser Ser Ala Ser Gly Thr Ala
            340                 345                 350

Gly Lys Tyr Glu Arg Cys Gly Gly Gln Gly Trp Thr Gly Ala Thr Thr
        355                 360                 365

Cys Val Asp Gly Trp Thr Cys Lys Gln Trp Asn Pro Tyr Tyr Tyr Gln
    370                 375                 380

Cys Val Glu Ser Ala
385

<210> SEQ ID NO 37
<211> LENGTH: 406
<212> TYPE: PRT
<213> ORGANISM: Aspergillus aculeatus

<400> SEQUENCE: 37

Met Arg Gln Ala Gln Ser Leu Ser Leu Leu Thr Ala Leu Leu Ser Ala
1               5                   10                  15

Thr Arg Val Ala Gly His Gly His Val Thr Asn Val Val Asn Gly
            20                  25                  30

Val Tyr Tyr Glu Gly Phe Asp Ile Asn Ser Phe Pro Tyr Glu Ser Asp
        35                  40                  45

Pro Pro Lys Val Ala Ala Trp Thr Thr Pro Asn Thr Gly Asn Gly Phe
    50                  55                  60

Ile Ser Pro Ser Asp Tyr Gly Thr Asp Asp Ile Ile Cys His Gln Asn
```

65                  70                  75                  80
Ala Thr Asn Ala Gln Ala His Ile Val Val Ala Ala Gly Asp Lys Ile
                85                  90                  95

Asn Ile Gln Trp Thr Ala Trp Pro Asp Ser His His Gly Pro Val Leu
            100                 105                 110

Asp Tyr Leu Ala Arg Cys Asp Gly Glu Cys Glu Thr Val Asp Lys Thr
        115                 120                 125

Thr Leu Glu Phe Phe Lys Ile Asp Gly Val Gly Leu Ile Ser Asp Thr
    130                 135                 140

Glu Val Pro Gly Thr Trp Gly Asp Asp Gln Leu Ile Ala Asn Asn Asn
145                 150                 155                 160

Ser Trp Leu Val Glu Ile Pro Pro Thr Ile Ala Pro Gly Asn Tyr Val
                165                 170                 175

Leu Arg His Glu Leu Ile Ala Leu His Ser Ala Gly Thr Glu Asp Gly
            180                 185                 190

Ala Gln Asn Tyr Pro Gln Cys Phe Asn Leu Gln Val Thr Gly Ser Gly
        195                 200                 205

Thr Asp Glu Pro Ala Gly Thr Leu Gly Thr Lys Leu Tyr Thr Glu Asp
    210                 215                 220

Glu Ala Gly Ile Val Val Asn Ile Tyr Thr Ser Leu Ser Ser Tyr Ala
225                 230                 235                 240

Val Pro Gly Pro Thr Gln Tyr Ser Gly Ala Val Ser Val Ser Gln Ser
                245                 250                 255

Thr Ser Ala Ile Thr Ser Thr Gly Thr Ala Val Val Gly Ser Gly Ser
            260                 265                 270

Ala Val Ala Thr Ser Ala Ala Ala Thr Thr Ser Ala Ala Ala Ser
        275                 280                 285

Ser Ala Ala Ala Ala Thr Thr Ala Ala Val Thr Ser Ala Asn Ala
    290                 295                 300

Asn Thr Gln Ile Ala Gln Pro Ser Ser Ser Ser Tyr Ser Gln Ile
305                 310                 315                 320

Ala Val Gln Val Pro Ser Ser Trp Thr Thr Leu Val Thr Val Thr Pro
                325                 330                 335

Pro Ala Ala Ala Thr Thr Pro Ala Ala Val Pro Glu Pro Gln Thr
            340                 345                 350

Pro Ser Ala Ser Ser Gly Ala Thr Thr Ser Ser Ser Gly Ala
        355                 360                 365

Ala Gln Ser Leu Tyr Gly Gln Cys Gly Gly Ile Asn Trp Thr Gly Ala
    370                 375                 380

Thr Ser Cys Val Glu Gly Ala Thr Cys Tyr Gln Tyr Asn Pro Tyr Tyr
385                 390                 395                 400

Tyr Gln Cys Ile Ser Ala
                405

<210> SEQ ID NO 38
<211> LENGTH: 427
<212> TYPE: PRT
<213> ORGANISM: Aspergillus aculeatus

<400> SEQUENCE: 38

Met Ser Leu Ser Lys Ile Ala Thr Leu Leu Gly Ser Val Ser Leu
1               5                   10                  15

Val Ala Gly His Gly Tyr Val Ser Ser Ile Glu Val Asp Gly Thr Thr
            20                  25                  30

-continued

Tyr Gly Gly Tyr Leu Val Asp Thr Tyr Tyr Glu Ser Asp Pro Pro
         35                  40                  45

Glu Leu Ile Ala Trp Ser Thr Asn Ala Thr Asp Asp Gly Tyr Val Ser
 50                  55                  60

Pro Ser Asp Tyr Glu Ser Val Asn Ile Ile Cys His Lys Gly Ser Ala
 65                  70                  75                  80

Pro Gly Ala Leu Ser Ala Pro Val Ala Pro Gly Gly Trp Val Gln Met
                 85                  90                  95

Thr Trp Asn Thr Trp Pro Thr Asp His His Gly Pro Val Ile Thr Tyr
            100                 105                 110

Met Ala Asn Cys His Gly Ser Cys Ala Asp Val Asp Lys Thr Thr Leu
            115                 120                 125

Glu Phe Phe Lys Ile Asp Ala Gly Gly Leu Ile Asp Asp Thr Asp Val
        130                 135                 140

Pro Gly Thr Trp Ala Thr Asp Glu Leu Ile Glu Asp Ser Tyr Ser Arg
145                 150                 155                 160

Asn Ile Thr Ile Pro Ser Asp Ile Ala Pro Gly Tyr Tyr Val Leu Arg
                165                 170                 175

His Glu Ile Ile Ala Leu His Ser Ala Glu Asn Leu Asp Gly Ala Gln
            180                 185                 190

Asn Tyr Pro Gln Cys Ile Asn Leu Glu Val Thr Gly Ser Glu Thr Ala
        195                 200                 205

Thr Pro Ser Gly Thr Leu Gly Thr Ala Leu Tyr Lys Glu Thr Asp Pro
210                 215                 220

Gly Ile Tyr Val Asp Ile Trp Asn Thr Leu Ser Thr Tyr Thr Ile Pro
225                 230                 235                 240

Gly Pro Ala Leu Tyr Thr Ala Gly Ser Thr Ala Thr Ala Ala Ala
                245                 250                 255

Ala Asp Thr Thr Thr Thr Ser Ala Gly Thr Thr Ala Glu Ala Thr Thr
            260                 265                 270

Ala Ala Ala Ala Val Ser Thr Thr Ala Asp Ala Val Pro Thr Glu Ser
        275                 280                 285

Ser Ala Pro Ser Glu Thr Ser Ala Thr Thr Ala Asn Pro Ala Arg Pro
290                 295                 300

Thr Ala Gly Ser Asp Ile Arg Phe Gln Pro Gly Gln Val Lys Ala Gly
305                 310                 315                 320

Ala Ser Val Asn Asn Ser Ala Thr Glu Thr Ser Ser Gly Glu Ser Ala
                325                 330                 335

Thr Thr Thr Thr Thr Ser Val Ala Thr Ala Ala Ser Ser Ala Asp Ser
            340                 345                 350

Ser Thr Thr Ser Gly Val Leu Ser Gly Ala Cys Ser Gln Glu Gly Tyr
        355                 360                 365

Trp Tyr Cys Asn Gly Gly Thr Ala Phe Gln Arg Cys Val Asn Gly Glu
370                 375                 380

Trp Asp Ala Ser Gln Ser Val Ala Ala Gly Thr Val Cys Thr Ala Gly
385                 390                 395                 400

Ile Ser Glu Thr Ile Thr Ile Ser Ala Ala Thr Arg Arg Asp Ala
                405                 410                 415

Met Arg Arg His Leu Ala Arg Pro Lys Arg His
            420                 425

<210> SEQ ID NO 39
<211> LENGTH: 267
<212> TYPE: PRT

<213> ORGANISM: Aspergillus aculeatus

<400> SEQUENCE: 39

| Met | Leu | Val | Lys | Leu | Ile | Ser | Phe | Leu | Ser | Ala | Ala | Thr | Ser | Val | Ala |
|---|---|---|---|---|---|---|---|---|---|---|---|---|---|---|---|
| 1 | | | | 5 | | | | | 10 | | | | | 15 | |

| Ala | His | Gly | His | Val | Ser | Asn | Ile | Val | Ile | Asn | Gly | Val | Ser | Tyr | Arg |
|---|---|---|---|---|---|---|---|---|---|---|---|---|---|---|---|
| | | | 20 | | | | | 25 | | | | | 30 | | |

| Gly | Trp | Asp | Ile | Asn | Ser | Asp | Pro | Tyr | Asn | Ser | Asn | Pro | Pro | Val | Val |
|---|---|---|---|---|---|---|---|---|---|---|---|---|---|---|---|
| | | | 35 | | | | | 40 | | | | | 45 | | |

| Val | Ala | Trp | Gln | Thr | Pro | Asn | Thr | Ala | Asn | Gly | Phe | Ile | Ser | Pro | Asp |
|---|---|---|---|---|---|---|---|---|---|---|---|---|---|---|---|
| | 50 | | | | | 55 | | | | | 60 | | | | |

| Ala | Tyr | Asp | Thr | Asp | Asp | Val | Ile | Cys | His | Leu | Ser | Ala | Thr | Asn | Ala |
|---|---|---|---|---|---|---|---|---|---|---|---|---|---|---|---|
| 65 | | | | | 70 | | | | | 75 | | | | | 80 |

| Arg | Gly | His | Ala | Val | Val | Ala | Ala | Gly | Asp | Lys | Ile | Ser | Leu | Gln | Trp |
|---|---|---|---|---|---|---|---|---|---|---|---|---|---|---|---|
| | | | | 85 | | | | | 90 | | | | | 95 | |

| Thr | Thr | Trp | Pro | Asp | Ser | His | His | Gly | Pro | Val | Ile | Ser | Tyr | Leu | Ala |
|---|---|---|---|---|---|---|---|---|---|---|---|---|---|---|---|
| | | | | 100 | | | | | 105 | | | | | 110 | |

| Asn | Cys | Gly | Ser | Ser | Cys | Glu | Thr | Val | Asp | Lys | Thr | Thr | Leu | Glu | Phe |
|---|---|---|---|---|---|---|---|---|---|---|---|---|---|---|---|
| | | | | 115 | | | | | 120 | | | | | 125 | |

| Phe | Lys | Ile | Asp | Gly | Val | Gly | Leu | Val | Asp | Glu | Ser | Asn | Pro | Pro | Gly |
|---|---|---|---|---|---|---|---|---|---|---|---|---|---|---|---|
| | 130 | | | | | 135 | | | | | 140 | | | | |

| Ile | Trp | Gly | Asp | Asp | Glu | Leu | Ile | Ala | Asn | Asn | Asn | Ser | Trp | Leu | Val |
|---|---|---|---|---|---|---|---|---|---|---|---|---|---|---|---|
| 145 | | | | | 150 | | | | | 155 | | | | | 160 |

| Glu | Ile | Pro | Ala | Ser | Ile | Ala | Pro | Gly | Tyr | Tyr | Val | Leu | Arg | His | Glu |
|---|---|---|---|---|---|---|---|---|---|---|---|---|---|---|---|
| | | | | 165 | | | | | 170 | | | | | 175 | |

| Leu | Ile | Ala | Leu | His | Gly | Ala | Gly | Ser | Glu | Asn | Gly | Ala | Gln | Asn | Tyr |
|---|---|---|---|---|---|---|---|---|---|---|---|---|---|---|---|
| | | | 180 | | | | | 185 | | | | | 190 | | |

| Met | Gln | Cys | Phe | Asn | Leu | Gln | Val | Thr | Gly | Thr | Gly | Thr | Val | Gln | Pro |
|---|---|---|---|---|---|---|---|---|---|---|---|---|---|---|---|
| | 195 | | | | | 200 | | | | | 205 | | | | |

| Ser | Gly | Val | Leu | Gly | Thr | Glu | Leu | Tyr | Lys | Pro | Thr | Asp | Ala | Gly | Ile |
|---|---|---|---|---|---|---|---|---|---|---|---|---|---|---|---|
| 210 | | | | | 215 | | | | | 220 | | | | | |

| Leu | Val | Asn | Ile | Tyr | Gln | Ser | Leu | Ser | Thr | Tyr | Val | Val | Pro | Gly | Pro |
|---|---|---|---|---|---|---|---|---|---|---|---|---|---|---|---|
| 225 | | | | | 230 | | | | | 235 | | | | | 240 |

| Thr | Leu | Ile | Pro | Gln | Ala | Val | Ser | Leu | Val | Gln | Ser | Ser | Ser | Thr | Ile |
|---|---|---|---|---|---|---|---|---|---|---|---|---|---|---|---|
| | | | | 245 | | | | | 250 | | | | | 255 | |

| Thr | Ala | Ser | Gly | Thr | Ala | Val | Thr | Thr | Thr | Ala |
|---|---|---|---|---|---|---|---|---|---|---|
| | | | 260 | | | | | 265 | | |

<210> SEQ ID NO 40
<211> LENGTH: 273
<212> TYPE: PRT
<213> ORGANISM: Aspergillus aculeatus

<400> SEQUENCE: 40

| Met | Lys | Tyr | Leu | Ala | Ile | Phe | Ala | Ala | Ala | Ala | Gly | Leu | Ala | Arg |
|---|---|---|---|---|---|---|---|---|---|---|---|---|---|---|
| 1 | | | | 5 | | | | | 10 | | | | | 15 |

| Pro | Thr | Ala | Ala | His | Tyr | Ile | Phe | Ser | Lys | Leu | Ile | Leu | Asp | Gly | Glu |
|---|---|---|---|---|---|---|---|---|---|---|---|---|---|---|---|
| | | | 20 | | | | | 25 | | | | | 30 | | |

| Val | Ser | Glu | Asp | Trp | Gln | Tyr | Ile | Arg | Lys | Thr | Thr | Arg | Glu | Thr | Cys |
|---|---|---|---|---|---|---|---|---|---|---|---|---|---|---|---|
| | | | 35 | | | | | 40 | | | | | 45 | | |

| Tyr | Leu | Pro | Thr | Lys | Phe | Thr | Asp | Thr | Phe | Asp | Asn | Leu | Thr | Pro | Asn |
|---|---|---|---|---|---|---|---|---|---|---|---|---|---|---|---|
| | | | 50 | | | | | 55 | | | | | 60 | | |

| Asp | Gln | Asp | Phe | Arg | Cys | Asn | Leu | Gly | Ser | Phe | Ser | Asn | Ala | Ala | Lys |
|---|---|---|---|---|---|---|---|---|---|---|---|---|---|---|---|
| 65 | | | | | 70 | | | | | 75 | | | | | 80 |

| Thr | Glu | Val | Ala | Glu | Val | Glu | Ala | Gly | Ser | Thr | Ile | Gly | Met | Gln | Leu |
|---|---|---|---|---|---|---|---|---|---|---|---|---|---|---|---|

```
                85                  90                  95
Phe Ala Gly Ser His Met Arg His Pro Gly Pro Ala Gln Val Phe Met
            100                 105                 110
Ser Lys Ala Pro Ser Gly Asn Val Gln Ser Tyr Glu Gly Asp Gly Ser
            115                 120                 125
Trp Phe Lys Ile Trp Glu Arg Thr Leu Cys Asp Lys Ser Gly Asp Leu
130                 135                 140
Thr Gly Asp Ala Trp Cys Thr Tyr Gly Gln Thr Glu Ile Glu Phe Gln
145                 150                 155                 160
Ile Pro Glu Ala Thr Pro Thr Gly Glu Tyr Leu Val Arg Ala Glu His
                165                 170                 175
Ile Gly Leu His Arg Ala Gln Ser Asn Gln Ala Glu Phe Tyr Tyr Ser
            180                 185                 190
Cys Ala Gln Val Lys Val Thr Gly Asn Gly Thr Gly Val Pro Ser Gln
            195                 200                 205
Thr Tyr Gln Ile Pro Gly Met Tyr Asn Asp Arg Ser Glu Leu Phe Asn
            210                 215                 220
Gly Leu Asn Leu Trp Ser Tyr Ser Val Glu Asn Val Glu Ala Ala Met
225                 230                 235                 240
Lys Asn Ser Ile Val Gly Asp Glu Ile Trp Asn Gly Ser Ser Val Pro
                245                 250                 255
Ser Glu Ser His Val Pro Lys Tyr Lys Lys Ser His Ala Cys Arg Val
            260                 265                 270
Tyr

<210> SEQ ID NO 41
<211> LENGTH: 322
<212> TYPE: PRT
<213> ORGANISM: Aurantiporus alborubescens

<400> SEQUENCE: 41

Met Arg Thr Ile Ala Thr Phe Val Thr Leu Val Ala Ser Val Leu Pro
1               5                   10                  15
Ala Val Leu Ala His Gly Gly Val Leu Ser Tyr Ser Asn Gly Gly Asn
            20                  25                  30
Trp Tyr Trp Gly Trp Lys Pro Tyr Asn Ser Pro Asp Gly Gln Thr Thr
        35                  40                  45
Ile Gln Arg Pro Trp Ala Thr Tyr Asn Pro Ile Thr Asp Ala Thr Asp
    50                  55                  60
Pro Thr Ile Ala Cys Asn Asn Asp Gly Thr Ser Gly Ala Leu Gln Leu
65                  70                  75                  80
Thr Ala Thr Val Ala Ala Gly Ser Ala Ile Thr Ala Tyr Trp Asn Gln
                85                  90                  95
Val Trp Pro His Asp Lys Gly Pro Met Thr Thr Tyr Leu Ala Gln Cys
            100                 105                 110
Pro Gly Ser Thr Cys Thr Gly Val Asn Ala Lys Thr Leu Lys Trp Phe
            115                 120                 125
Lys Ile Asp His Ala Gly Leu Leu Ser Gly Thr Val Tyr Ser Gly Ser
            130                 135                 140
Trp Ala Ser Gly Lys Met Ile Ala Gln Asn Ser Thr Trp Thr Thr Thr
145                 150                 155                 160
Ile Pro Ala Thr Val Pro Ser Gly Asn Tyr Leu Ile Arg Phe Glu Thr
                165                 170                 175
Ile Ala Leu His Ser Leu Pro Ala Gln Phe Tyr Pro Glu Cys Ala Gln
```

```
                   180                 185                 190
Ile Gln Ile Thr Gly Gly Ser Arg Ala Pro Thr Ala Ala Glu Leu
            195                 200                 205

Val Ser Phe Pro Gly Ala Tyr Ser Asn Asn Asp Pro Gly Val Asn Ile
            210                 215                 220

Asp Ile Tyr Ser Asn Ala Ala Gln Ser Ala Thr Thr Tyr Val Ile Pro
225                 230                 235                 240

Gly Pro Pro Leu Tyr Gly Gly Ala Ser Gly Ser Gly Pro Ser Ser Ala
                245                 250                 255

Pro Pro Ser Ser Thr Pro Gly Ser Ser Thr Ser His Gly Pro Thr
            260                 265                 270

Ser Val Ser Thr Ser Ser Ser Ala Ala Pro Ser Thr Thr Gly Thr Val
            275                 280                 285

Thr Gln Tyr Gly Gln Cys Gly Gly Ile Gly Trp Ala Gly Ala Thr Gly
            290                 295                 300

Cys Ile Ser Pro Phe Lys Cys Thr Val Ile Asn Asp Tyr Tyr Gln
305                 310                 315                 320

Cys Leu

<210> SEQ ID NO 42
<211> LENGTH: 234
<212> TYPE: PRT
<213> ORGANISM: Aurantiporus alborubescens

<400> SEQUENCE: 42

Met Lys Ala Ile Leu Ala Ile Phe Ser Ala Leu Ala Pro Leu Ala Ala
1               5                   10                  15

Ala His Tyr Thr Phe Pro Asp Phe Ile Val Asn Gly Thr Thr Thr Ala
            20                  25                  30

Asp Trp Val Tyr Ile Arg Glu Thr Ala Asn His Tyr Ser Asn Gly Pro
        35                  40                  45

Val Thr Asn Val Asn Asp Pro Glu Phe Arg Cys Tyr Glu Leu Asp Leu
    50                  55                  60

Gln Asn Thr Ala Ala Ser Thr Leu Thr Ala Thr Val Ser Ala Gly Ser
65                  70                  75                  80

Ser Val Gly Phe Lys Ala Asn Ser Ala Leu Tyr His Pro Gly Tyr Leu
                85                  90                  95

Asp Val Tyr Met Ser Lys Ala Thr Pro Ala Ala Asn Ser Pro Ser Ala
            100                 105                 110

Gly Thr Asp Gln Ser Trp Phe Lys Val Tyr Glu Ser Ala Pro Val Phe
        115                 120                 125

Ala Asn Gly Ala Leu Ser Phe Pro Ser Glu Asn Ile Gln Ser Phe Thr
130                 135                 140

Phe Thr Ile Pro Lys Ser Leu Pro Ser Gly Gln Tyr Leu Ile Arg Val
145                 150                 155                 160

Glu His Ile Ala Leu His Ser Ala Ser Ser Tyr Gly Gly Ala Gln Phe
                165                 170                 175

Tyr Ile Ser Cys Ala Gln Val Asn Val Val Asn Gly Gly Asn Gly Asn
            180                 185                 190

Pro Gly Pro Leu Val Lys Ile Pro Gly Val Tyr Thr Gly Asn Glu Pro
        195                 200                 205

Gly Ile Leu Ile Asn Ile Tyr Ser Phe Pro Pro Gly Phe Ser Gly Tyr
    210                 215                 220

Gln Ser Pro Gly Pro Ala Val Trp Arg Gly
                225                 230
```

<210> SEQ ID NO 43
<211> LENGTH: 233
<212> TYPE: PRT
<213> ORGANISM: Trichophaea saccata

<400> SEQUENCE: 43

Met Thr Pro Leu Lys Leu Arg Pro Leu Leu Leu Val Leu Ser Thr
1               5                   10                  15

Thr Leu Ser Leu Val His Ala His Tyr Arg Phe Tyr Glu Leu Ile Ala
            20                  25                  30

Asn Gly Ala Thr His Ala Ser Phe Glu Tyr Ile Arg Gln Trp Val Pro
        35                  40                  45

Ile Tyr Ser Asn Ser Pro Val Thr Asp Val Thr Ser Val Asn Leu Arg
    50                  55                  60

Cys Asn Val Asn Ala Thr Pro Ala Ala Glu Val Ile Thr Val Ala Ala
65                  70                  75                  80

Gly Ser Thr Val Gly Phe Val Ala Asp Thr Thr Val Thr His Pro Gly
                85                  90                  95

Ala Phe Thr Ala Tyr Met Ala Lys Ala Pro Glu Asp Ile Thr Glu Trp
            100                 105                 110

Asp Gly Asn Gly Asp Trp Phe Lys Ile Trp Glu Lys Gly Pro Thr Ser
        115                 120                 125

Ile Thr Ser Ser Gly Ile Thr Trp Asp Val Thr Asp Thr Gln Trp Thr
    130                 135                 140

Phe Thr Ile Pro Ser Ala Thr Pro Asn Gly Gln Tyr Leu Leu Arg Phe
145                 150                 155                 160

Glu His Ile Ala Leu His Ala Ala Ser Thr Val Gly Gly Ala Gln Phe
                165                 170                 175

Tyr Met Ser Cys Ala Gln Ile Gln Val Thr Asn Gly Gly Asn Gly Ser
            180                 185                 190

Pro Gly Pro Thr Ile Lys Phe Pro Gly Gly Tyr Ser Ala Thr Asp Pro
        195                 200                 205

Gly Ile Leu Ile Asn Ile Tyr Tyr Pro Ile Pro Thr Ser Tyr Thr Ile
    210                 215                 220

Pro Gly Pro Pro Val Trp Thr Gly Lys
225                 230

<210> SEQ ID NO 44
<211> LENGTH: 237
<212> TYPE: PRT
<213> ORGANISM: Trichophaea saccata

<400> SEQUENCE: 44

Met Lys Cys Leu Leu Ser Leu Leu Ala Ala Thr Ala Val Ser Ala
1               5                   10                  15

His Thr Ile Phe Gln Glu Ile Gly Ile Asn Gly Val Met Gln Ala Arg
            20                  25                  30

Tyr Asp Tyr Met Arg Leu Pro Ser Tyr Asp Gly Pro Ile Thr Asp Val
        35                  40                  45

Thr Ser Thr Tyr Met Ala Cys Asn Gly Gly Pro Asn Pro Leu Val Gln
    50                  55                  60

Ile Ser Asn Asp Val Ala Phe Val Lys Ala Gly Asp Ser Ile Thr Leu
65                  70                  75                  80

Gln Trp Ala Gln Thr Leu Thr Thr Asp Phe Asn Thr Gly Leu Ile Ile

```
                    85                  90                  95
Asp Pro Ser His Leu Gly Pro Val Met Val Tyr Met Ala Lys Val Pro
            100                 105                 110

Ser Ala Thr Gly Pro Ile Pro Asn Ser Gly Trp Phe Lys Ile Tyr Glu
            115                 120                 125

Asp Gly Tyr Asp Pro Thr Thr Lys Thr Trp Ala Val Thr Lys Leu Ile
            130                 135                 140

Asn Asn Lys Gly Lys Val Thr Val Thr Ile Pro Ser Cys Leu Pro Ala
145                 150                 155                 160

Gly Asp Tyr Leu Leu Arg Gly Glu Ile Ile Ala Leu His Ala Ala Ser
                165                 170                 175

Thr Tyr Pro Gly Ala Gln Phe Tyr Met Glu Cys Ala Gln Leu Arg Leu
            180                 185                 190

Thr Ser Gly Gly Thr Lys Met Pro Thr Thr Tyr Asn Ile Pro Gly Ile
            195                 200                 205

Tyr Ser Pro Thr Asp Pro Gly Val Thr Phe Asn Leu Tyr Asn Gly Phe
            210                 215                 220

Thr Ser Tyr Thr Ile Pro Gly Pro Arg Pro Phe Thr Cys
225                 230                 235

<210> SEQ ID NO 45
<211> LENGTH: 484
<212> TYPE: PRT
<213> ORGANISM: Penicillium thomii

<400> SEQUENCE: 45

Met Ser Leu Ser Lys Ile Ser Gly Leu Ile Leu Gly Ser Ala Ala Leu
1               5                   10                  15

Val Ala Gly His Gly Tyr Val Ser Gly Ile Val Val Asp Asp Thr Tyr
            20                  25                  30

Tyr Gly Gly Tyr Leu Val Thr Gln Tyr Pro Tyr Glu Ser Asp Ala Pro
            35                  40                  45

Glu Leu Ile Ala Trp Ser Glu Gln Glu Thr Asp Leu Gly Tyr Ile Asp
        50                  55                  60

Gly Ser Glu Tyr Ala Asn Ser Asn Ile Ile Cys His Lys Glu Ala Lys
65                  70                  75                  80

Pro Gly Ala Leu Glu Ala Pro Val Lys Ala Gly Gly Ser Val Glu Leu
                85                  90                  95

Gln Trp Thr Thr Trp Pro Thr Ser His His Gly Pro Val Ile Thr Tyr
            100                 105                 110

Met Ala Asn Cys Asn Gly Asp Cys Asp Asp Val Asp Lys Thr Thr Leu
            115                 120                 125

Gln Phe Phe Lys Ile Asp Gln Gly Gly Leu Ile Ser Asp Thr Thr Glu
            130                 135                 140

Pro Gly Thr Trp Ala Thr Asp Asn Leu Ile Ala Asn Asn Ser Arg
145                 150                 155                 160

Thr Val Thr Val Pro Ser Asp Ile Ala Asp Gly Asn Tyr Val Leu Arg
                165                 170                 175

His Glu Ile Ile Ala Leu His Ser Ala Gly Glu Thr Asn Gly Ala Gln
            180                 185                 190

Asn Tyr Pro Gln Cys Ile Asn Leu Lys Val Thr Gly Gly Ser Ala
            195                 200                 205

Thr Pro Ser Gly Thr Leu Gly Thr Ala Leu Tyr Lys Asn Thr Asp Pro
210                 215                 220
```

```
Gly Ile Leu Ile Asn Ile Tyr Thr Ser Leu Ser Thr Tyr Asp Ile Pro
225                 230                 235                 240

Gly Pro Thr Leu Tyr Thr Ala Gly Ala Ala Ala Thr Ala Ala Ser
            245                 250                 255

Thr Ala Ala Ser Ser Thr Ala Ala Val Thr Thr Ala Asp Ala Val
                260                 265                 270

Thr Thr Ala Ala Ala Val Thr Ser Ser Ala Ser Val Glu Val Val
            275                 280                 285

Pro Thr Thr Pro Ser Ser Ser Ile Val Ser Ala Phe Pro Thr Trp
            290                 295                 300

Ser Pro Ser Ser Thr Pro Pro Phe Ser Asn Ser Ser Asn Gly Trp Arg
305                 310                 315                 320

Pro Ser Phe Ser Arg Gly Pro Gly Pro Arg Phe Thr Ser Ala Pro
            325                 330                 335

Ala Pro Gln Phe Ser Ala Pro Ser Gly Ala Gln Gln Lys Gln Ser Ala
                340                 345                 350

Thr Ala Thr Pro Ile Val Ala Thr Pro Val Val Ile Thr Met Thr Glu
            355                 360                 365

Thr Ser Thr Ser Trp Val Thr Glu Met Val Thr Leu Thr Asp Lys Ser
370                 375                 380

Val Val Gln Thr Thr Ser Ala Val Pro Val Val Ala Ala Thr Thr
385                 390                 395                 400

Thr Leu Thr Glu Gly Ser Glu Pro Ala Gln Thr Ala Ser Pro Ser Val
            405                 410                 415

Val Ser Gly Ser Ser Ser Ser Gly Ser Ser Ser Ser Thr Thr Thr
            420                 425                 430

Thr Ser Lys Thr Ser Thr Gly Ser Asp Tyr Val Ser Ser Asp Trp Met
435                 440                 445

Ser Tyr Leu Ser Ser Leu Ser Ala Ala Glu Val Leu Gln Met Leu Arg
            450                 455                 460

Gln Thr Phe Arg Trp Met Val Ser Asn Asp Lys Val His Ala Arg Asp
465                 470                 475                 480

Ile Thr Ile Asn

<210> SEQ ID NO 46
<211> LENGTH: 320
<212> TYPE: PRT
<213> ORGANISM: Talaromyces stipitatus

<400> SEQUENCE: 46

Met Pro Ser Thr Lys Val Ala Ala Leu Ser Ala Val Leu Ala Leu Ala
1               5                   10                  15

Ser Thr Val Ala Gly His Gly Phe Val Gln Asn Ile Val Ile Asp Gly
            20                  25                  30

Lys Ser Tyr Thr Gly Tyr Leu Val Asn Gln Tyr Pro Tyr Gln Ser Asn
        35                  40                  45

Pro Pro Ala Val Ile Gly Trp Ser Thr Thr Ala Thr Asp Leu Gly Phe
    50                  55                  60

Val Asp Gly Ser Gly Tyr Thr Asn Pro Asp Ile Ile Cys His Lys Asn
65                  70                  75                  80

Ala Lys Pro Gly Gln Leu Ser Ala Pro Val Ala Ala Gly Gly Lys Val
                85                  90                  95

Glu Leu Glu Trp Thr Thr Trp Pro Glu Ser His His Gly Pro Val Ile
            100                 105                 110
```

```
Ser Tyr Leu Ala Asn Cys Asn Gly Asp Cys Thr Thr Val Asp Lys Thr
            115                 120                 125

Lys Leu Glu Phe Val Lys Ile Asp Gln Arg Gly Leu Ile Asp Asp Ser
130                 135                 140

Asn Pro Pro Gly Thr Trp Ala Ala Asp Gln Leu Ile Ala Ala Asn Asn
145                 150                 155                 160

Ser Trp Thr Val Thr Ile Pro Glu Ser Ile Ala Pro Gly Asn Tyr Val
                165                 170                 175

Leu Arg His Glu Ile Ile Ala Leu His Ser Ala Asn Asn Ala Thr Gly
            180                 185                 190

Ala Gln Asn Tyr Pro Gln Cys Ile Asn Leu Gln Ile Thr Gly Ser Gly
            195                 200                 205

Thr Ala Asn Pro Ser Gly Thr Pro Gly Glu Lys Leu Tyr Thr Pro Thr
            210                 215                 220

Asp Pro Gly Ile Leu Val Asn Ile Tyr Gln Ser Leu Ser Ser Tyr Val
225                 230                 235                 240

Ile Pro Gly Pro Thr Leu Trp Ser Gly Ala Ala His Val Val Ala
                245                 250                 255

Thr Ala Ala Gly Ser Ala Thr Gly Val Ala Ser Ala Thr Ala Thr Pro
            260                 265                 270

Thr Thr Leu Val Thr Ala Val Ser Ser Pro Thr Gly Ala Pro Ser Val
            275                 280                 285

Val Thr Pro Glu Ala Pro Ser Val Thr Ser Phe Ala Pro Val Val Thr
            290                 295                 300

Val Thr Asp Val Val Thr Val Thr Thr Val Ile Thr Thr Thr Ile Ser
305                 310                 315                 320

<210> SEQ ID NO 47
<211> LENGTH: 330
<212> TYPE: PRT
<213> ORGANISM: Neurospora crassa

<400> SEQUENCE: 47

Met Arg Ser Thr Leu Val Thr Gly Leu Ile Ala Gly Leu Leu Ser Gln
1               5                   10                  15

Gln Ala Ala Ala His Ala Thr Phe Gln Ala Leu Trp Val Asp Gly Ala
            20                  25                  30

Asp Tyr Gly Ser Gln Cys Ala Arg Val Pro Pro Ser Asn Ser Pro Val
        35                  40                  45

Thr Asp Val Thr Ser Asn Ala Met Arg Cys Asn Thr Gly Thr Ser Pro
50                  55                  60

Val Ala Lys Lys Cys Pro Val Lys Ala Gly Ser Thr Val Thr Val Glu
65                  70                  75                  80

Met His Gln Gln Ala Asn Asp Arg Ser Cys Ser Ser Glu Ala Ile Gly
                85                  90                  95

Gly Ala His Tyr Gly Pro Val Leu Val Tyr Met Ser Lys Val Ser Asp
            100                 105                 110

Ala Ala Ser Ala Asp Gly Ser Ser Gly Trp Phe Lys Ile Phe Glu Asp
            115                 120                 125

Thr Trp Ala Lys Lys Pro Ser Ser Ser Gly Asp Asp Phe Trp
            130                 135                 140

Gly Val Lys Asp Leu Asn Ser Cys Cys Gly Lys Met Gln Val Lys Ile
145                 150                 155                 160

Pro Ser Asp Ile Pro Ala Gly Asp Tyr Leu Leu Arg Ala Glu Val Ile
                165                 170                 175
```

```
Ala Leu His Thr Ala Ala Ser Ala Gly Gly Ala Gln Leu Tyr Met Thr
            180             185             190

Cys Tyr Gln Ile Ser Val Thr Gly Gly Gly Ser Ala Thr Pro Ala Thr
            195             200             205

Val Ser Phe Pro Gly Ala Tyr Lys Ser Ser Asp Pro Gly Ile Leu Val
    210             215             220

Asp Ile His Ser Ala Met Ser Thr Tyr Val Ala Pro Gly Pro Ala Val
225             230             235             240

Tyr Ser Gly Gly Ser Ser Lys Lys Ala Gly Ser Gly Cys Val Gly Cys
                245             250             255

Glu Ser Thr Cys Lys Val Gly Ser Gly Pro Thr Gly Thr Ala Ser Ala
            260             265             270

Val Pro Val Ala Ser Thr Ser Ala Ala Ala Gly Gly Gly Gly Gly Gly
            275             280             285

Gly Ser Gly Gly Cys Ser Val Ala Lys Tyr Gln Gln Cys Gly Gly Thr
    290             295             300

Gly Tyr Thr Gly Cys Thr Cys Ala Ser Gly Ser Thr Cys Ser Ala
305             310             315             320

Val Ser Pro Pro Tyr Tyr Ser Gln Cys Val
            325             330
```